US012728163B2

(12) United States Patent
Loughhead et al.

(10) Patent No.: US 12,728,163 B2
(45) Date of Patent: *Sep. 8, 2026

(54) INTRACELLULAR DELIVERY OF BIOMOLECULES TO MODIFY IMMUNE RESPONSE

(71) Applicant: STEMCELL TECHNOLOGIES CANADA INC., Vancouver (CA)

(72) Inventors: Scott Loughhead, Durham, NC (US); LeeAnn Talarico, Milton, MA (US); Alfonso Vicente-Suarez, Brookline, MA (US); Matt Booty, Watertown, MA (US); Howard Bernstein, Cambridge, MA (US); Katarina Blagovic, Cambridge, MA (US); Armon R. Sharei, Somerville, MA (US); Kelan Hlavaty, Belmont, MA (US)

(73) Assignee: STEMCELL TECHNOLOGIES CANADA INC., Vancouver (CA)

( * ) Notice: Subject to any disclaimer, the term of this patent is extended or adjusted under 35 U.S.C. 154(b) by 1226 days.

This patent is subject to a terminal disclaimer.

(21) Appl. No.: 16/980,339

(22) PCT Filed: Mar. 11, 2019

(86) PCT No.: PCT/US2019/021705

§ 371 (c)(1),
(2) Date: Sep. 11, 2020

(87) PCT Pub. No.: WO2019/178006

PCT Pub. Date: Sep. 19, 2019

(65) Prior Publication Data

US 2021/0113628 A1 Apr. 22, 2021
US 2024/0374654 A2 Nov. 14, 2024

Related U.S. Application Data

(60) Provisional application No. 62/794,516, filed on Jan. 18, 2019, provisional application No. 62/738,941, filed on Sep. 28, 2018, provisional application No. 62/641,987, filed on Mar. 12, 2018.

(51) Int. Cl.

| | |
|---|---|
| ***A61P 35/00*** | (2006.01) |
| ***A61K 35/74*** | (2015.01) |
| ***A61K 39/02*** | (2006.01) |
| ***A61K 39/395*** | (2006.01) |
| ***A61K 40/11*** | (2025.01) |
| ***A61K 40/24*** | (2025.01) |
| ***A61K 40/46*** | (2025.01) |
| ***A61K 45/06*** | (2006.01) |
| ***C07K 16/28*** | (2006.01) |

(Continued)

(52) U.S. Cl.

CPC .............. *A61K 40/24* (2025.01); *A61K 35/74* (2013.01); *A61K 39/0208* (2013.01); *A61K 39/39541* (2013.01); *A61K 40/11* (2025.01); *A61K 40/46* (2025.01); *A61K 45/06* (2013.01); *A61P 35/00* (2018.01); *C07K 16/2818* (2013.01); *C07K 16/2827* (2013.01); *A61K 2039/505* (2013.01); *A61K 2039/585* (2013.01); *A61K 2039/804* (2018.08); *A61K 2039/812* (2018.08); *A61K 2039/82* (2018.08); *A61K 2039/844* (2018.08); *A61K 2039/852* (2018.08); *A61K 2039/86* (2018.08); *A61K 2039/868* (2018.08); *A61K 2039/876* (2018.08); *A61K 2039/884* (2018.08); *A61K 2239/31* (2023.05); *A61K 2239/38* (2023.05); *A61K 2239/55* (2023.05); *C12N 5/0636* (2013.01)

(58) Field of Classification Search

CPC ................ A61K 35/74; A61K 2039/86; A61K 2039/82; A61K 2039/852; A61K 2039/868; A61K 2039/812; A61K 2039/844; A61K 2039/876; A61K 2039/884; A61K 2039/804; A61K 39/0208; A61K 39/39541; A61K 45/06; A61K 2039/505; A61K 2039/585; A61P 35/00; C07K 16/2818; C07K 16/2827

See application file for complete search history.

(56) References Cited

U.S. PATENT DOCUMENTS

| | | | |
|---|---|---|---|
| 4,055,799 | A | 10/1977 | Coster |
| 4,376,634 | A | 3/1983 | Prior et al. |
| 4,835,457 | A | 5/1989 | Hanss |

(Continued)

FOREIGN PATENT DOCUMENTS

| | | | |
|---|---|---|---|
| CN | 101031641 | A | 9/2007 |
| CN | 103987836 | A | 8/2014 |

(Continued)

OTHER PUBLICATIONS

Kaka et al (Genetic Modification of T Cells with IL-21 Enhances Antigen Presentation and Generation of Central Memory Tumor-Specific Cytotoxic T Lymphocytes, JImmunother, 32(7): 726-736, 2009) (Year: 2009).*

(Continued)

*Primary Examiner* — Nelson B Moseley, II
*Assistant Examiner* — Dennis J Sullivan
(74) *Attorney, Agent, or Firm* — Smart & Biggar LP; Micheline Gravelle

(57) ABSTRACT

The present application provides T cells comprising an antigen and an adjuvant, methods of manufacturing such T cells, and methods of using such T cells, such as for modulating an immune response in an individual.

7 Claims, 35 Drawing Sheets

Specification includes a Sequence Listing.

(51) Int. Cl.

| | |
|---|---|
| *A61K 39/00* | (2006.01) |
| *C12N 5/0783* | (2010.01) |

(56) References Cited

U.S. PATENT DOCUMENTS

| | | | |
|---|---|---|---|
| 5,023,054 | A | 6/1991 | Sato |
| 8,147,867 | B2 | 4/2012 | Hong |
| 9,364,504 | B2 | 6/2016 | Godfrin |
| 9,950,049 | B2 | 4/2018 | Godfrin |
| 10,124,336 | B2 | 11/2018 | Sharei |
| 10,526,573 | B2 | 1/2020 | Ding |
| 10,696,944 | B2 | 6/2020 | Sharei |
| 10,780,151 | B2 | 9/2020 | Godfrin |
| 10,870,112 | B2 | 12/2020 | Sharei |
| 2004/0197898 | A1 | 10/2004 | Nakatani |
| 2006/0134067 | A1 | 6/2006 | Liu |
| 2006/0134772 | A1 | 6/2006 | Miles |
| 2007/0243523 | A1 | 10/2007 | Ionescu-zanetti |
| 2007/0249038 | A1 | 10/2007 | Adamo |
| 2008/0026465 | A1 | 1/2008 | Nakata |
| 2008/0241844 | A1 | 10/2008 | Kellogg |
| 2008/0311140 | A1 | 12/2008 | Lee |
| 2009/0280518 | A1 | 11/2009 | Adamo |
| 2010/0203068 | A1 | 8/2010 | Betz |
| 2010/0249621 | A1 | 9/2010 | Ichitani |
| 2011/0030808 | A1 | 2/2011 | Chiou |
| 2011/0300205 | A1 | 12/2011 | Geall |
| 2012/0009140 | A1 | 1/2012 | Godfrin |
| 2012/0207745 | A1 | 8/2012 | Godfrin |
| 2014/0287509 | A1 | 9/2014 | Sharei |
| 2016/0193605 | A1 | 7/2016 | Sharei |
| 2016/0324946 | A1 | 11/2016 | Godfrin |
| 2018/0003696 | A1 | 1/2018 | Sharei |
| 2018/0016539 | A1 | 1/2018 | Ding |
| 2018/0142198 | A1 | 5/2018 | Sharei |
| 2018/0201889 | A1 | 7/2018 | Sharei |
| 2018/0245089 | A1 | 8/2018 | Sharei |
| 2018/0344822 | A1 | 12/2018 | Godfrin |
| 2019/0017072 | A1 | 1/2019 | Ditommaso |
| 2019/0030536 | A1 | 1/2019 | Sharei |
| 2019/0093073 | A1 | 3/2019 | Sharei |
| 2019/0111082 | A1 | 4/2019 | Gilbert |
| 2019/0382796 | A1 | 12/2019 | Gilbert |
| 2020/0277566 | A1 | 9/2020 | Sharei |
| 2020/0316604 | A1 | 10/2020 | Dadgar |
| 2020/0318066 | A1 | 10/2020 | Sharei |
| 2020/0332243 | A1 | 10/2020 | Dadgar et al. |
| 2021/0038709 | A1 | 2/2021 | Loughhead |
| 2021/0077602 | A1 | 3/2021 | Godfrin et al. |
| 2021/0138050 | A1 | 5/2021 | Loughhead et al. |

FOREIGN PATENT DOCUMENTS

| | | | | |
|---|---|---|---|---|
| CN | 107109362 | A | 8/2017 | |
| JP | H01196566 | A | 8/1989 | |
| JP | H03257366 | A | 11/1991 | |
| JP | 2010025852 | A | 2/2010 | |
| JP | 2010-530362 | A | 9/2010 | |
| JP | 2012-526853 | A | 11/2012 | |
| JP | 2017-533702 | A | 11/2017 | |
| RU | 2424792 | C2 | 7/2011 | |
| RU | 2539989 | C1 | 1/2015 | |
| WO | 2002067863 | A2 | 9/2002 | |
| WO | 2003020039 | A1 | 3/2003 | |
| WO | 2005060993 | A1 | 7/2005 | |
| WO | 2006105251 | A2 | 10/2006 | |
| WO | 2007001677 | A2 | 1/2007 | |
| WO | 2007067032 | A1 | 6/2007 | |
| WO | 2007001677 | A3 | 7/2007 | |
| WO | 2007001677 | A9 | 8/2007 | |
| WO | 2008021465 | A2 | 2/2008 | |
| WO | WO-2009002159 | A2 * | 12/2008 | ............ A61K 39/12 |
| WO | 2009019317 | A1 | 2/2009 | |
| WO | 2009039125 | A | 3/2009 | |
| WO | 2010016800 | A1 | 2/2010 | |
| WO | 2011051346 | A1 | 5/2011 | |
| WO | 2011079217 | A1 | 6/2011 | |
| WO | 2011119492 | A2 | 9/2011 | |
| WO | 2012069568 | A2 | 5/2012 | |
| WO | 2013059343 | A1 | 4/2013 | |
| WO | 2013185032 | A1 | 12/2013 | |
| WO | 2014165707 | A2 | 10/2014 | |
| WO | 2015023982 | A1 | 2/2015 | |
| WO | WO-2015114506 | A2 * | 8/2015 | ....... G01N 33/54346 |
| WO | 2016070136 | A1 | 5/2016 | |
| WO | 2016077761 | A1 | 5/2016 | |
| WO | 2016115179 | A1 | 7/2016 | |
| WO | 2017008063 | A1 | 1/2017 | |
| WO | 2017041050 | A1 | 3/2017 | |
| WO | 2017041051 | A1 | 3/2017 | |
| WO | 2017117418 | A1 | 7/2017 | |
| WO | 2017123663 | A1 | 7/2017 | |
| WO | 2017192785 | A1 | 11/2017 | |
| WO | 2017192786 | A1 | 11/2017 | |
| WO | 2018106849 | A1 | 6/2018 | |
| WO | 2019113125 | A1 | 6/2019 | |
| WO | 2019126212 | A1 | 6/2019 | |
| WO | 2019178005 | A2 | 9/2019 | |
| WO | 2019178005 | A3 | 10/2019 | |
| WO | 2020072833 | A1 | 4/2020 | |
| WO | 2020154696 | A1 | 7/2020 | |
| WO | 2020176789 | A1 | 9/2020 | |
| WO | 2020210162 | A1 | 10/2020 | |

OTHER PUBLICATIONS

Xin et al (A Critical Role of IL-21-Induced BATF in Sustaining CD8-T-Cell-Mediated Chronic Viral Control, Cell Reports 13, pp. 1118-1124, 2015) (Year: 2015).*

Adamo, A. et al. (Aug. 7, 2012, e-pub. Jul. 10, 2012). "Microfluidics-Based Assessment of Cell Deformability," Anal Chem 84(15):6438-6443, 13 pages.

Bolhassani, A. et al. (Feb. 1, 2014, e-pub. Oct. 15, 2013). "Polymeric Nanoparticles, Potent Vectors for Vaccine Delivery Targeting Cancer and Infectious Diseases," Hum Vaccin & Immunother 10(2):321-332.

Chen, C. et al. (2009, e-pub. May 14, 2009). "Patch Clamping on Plane Glass-Fabrication of Hourglass Aperture and High Yield Ion Channel Recording," Lab Chip 9:2370-2380.

Chen, Xian-Zhen et al. (2010, e-pub. Jul. 4, 2009). "Toll Like Receptor Agonists Augment HPV 11 E7-Specific T Cell Responses By Modulating Monocyte-Derived Dendritic Cells," Arch Dermatol Res. 302(1):57-65.

Ding, X. et al. (Mar. 9, 2017). "High-Throughput Nuclear Delivery and Rapid Expression of DNA Via Mechanical and Electrical Cell-Membrane Disruption," Nature Biomedical Engineering 1(3):39, 15 pages.

Hallow, D.M. et al. (Mar. 1, 2008, e-pub. Sep. 18, 2007). "Shear-Induced Intracellular Loading of Cells With Molecules by Controlled Microfluidics," Biotechnology and Bioengineering 99(4):846-854.

Hillerdal, V. et al. (Jan. 18, 2014). "Systemic Treatment With CAR-engineered T Cells Against PSCA Delays Subcutaneous Tumor Growth And Prolongs Survival Of Mice," BMC Cancer 14(30):1-9.

Hosokawa, M.. et al. (Aug. 1, 2010). "Size-Selective Microcavity Array for Rapid and Efficient Detection of Circulating Tumor Cells," Analytical Chemistry 82(15):6629-6635.

Howarth, M. et al. (May 2008). "Monovalent, Reduced-Size Quantum Dots For Imaging Receptors On Living Cells," Nature Methods 5(5):397-399, 7 pages.

Indrova, M. et al. (Jan. 1, 2004). "Immunogenicity of Dendritic Cell-Based HPV16 E6/E7 Peptide Vaccines: CTL Activation and Protective Effects", Folia Biologica 50:184-193.

International Preliminary Report on Patentability issued Mar. 23, 2021, for Patent Application No. PCT/US2019/054586, filed Oct. 3, 2019, 17 pages.

International Preliminary Report on Patentability mailed Nov. 15, 2018, for Patent Application No. PCT/US2017/030933, filed May 3, 2017, 13 pages.

(56) References Cited

OTHER PUBLICATIONS

International Preliminary Report on Patentability mailed on Jun. 18, 2020, for International Patent Application No. PCT/US2018/063931, filed Dec. 4, 2018, 9 pages.
International Preliminary Report on Patentability, issued Sep. 15, 2020, for Patent Application No. PCT/US2019/021703, filed Mar. 11, 2019, 10 pages.
International Search Report and Written Opinion of the International Searching Authority mailed Apr. 16, 2020, for International Patent Application No. PCT/US2020/020194, filed Feb. 27, 2020, 16 pages.
International Search Report and Written Opinion of the International Searching Authority mailed Feb. 25, 2013, for International Patent Application No. PCT/US12/060646, filed Oct. 17, 2012, 10 pages.
International Search Report and Written Opinion of the International Searching Authority mailed Mar. 19, 2019, for International Patent Application No. PCT/US2018/063931, filed Dec. 14, 2018, 14 pages.
International Search Report and Written Opinion of the International Searching Authority mailed Oct. 16, 2019 for International Patent Application No. PCT/US2019/021705, filed Mar. 11, 2019, 25 pages.
International Search Report and Written Opinion of the International Searching Authority mailed on Mar. 11, 2016, for International Patent Application No. PCT/US2015/058489, filed Oct. 30, 2015, 18 pages.
International Search Report and Written Opinion of the International Searching Authority mailed Sep. 18, 2019, for International Patent Application No. PCT/US2019/021703, filed Mar. 11, 2019, 19 pages.
International Search Report and Written Opinion of the Searching Authority mailed on Feb. 12, 2020, for International Patent Application No. PCT/US2019/054586, filed Oct. 3, 2019, 27 pages.
International Search Report mailed Jul. 21, 2017, for International Patent Application No. PCT/2017030933 filed May 3, 2017, 4 pages.
Invitation to Pay Additional Fees mailed Dec. 19, 2019, for International Patent Application No. PCT/US2019/054586, filed Oct. 3, 2019, 8 pages.
Invitation to Pay Additional Fees mailed Jul. 24, 2019, for International Patent Application No. PCT/US2019/021703, filed Mar. 11, 2019, 14 pages.
Invitation to Pay Additional Fees mailed Jun. 28, 2019, for International Patent Application No. PCT/US2019/021705, filed Mar. 11, 2019, 17 pages.
Kada, G. et al. (Mar. 14, 1999). "Rapid Estimation of Avidin and Streptavidin by Fluorescence Quenching or Fluorescence Polarization," Biochim. Biophys. Acta. 1427(1):44-48.
Kaka, A. S. et al. (Sep. 1, 2009). "Genetic Modification of T Cells With IL-21 Enhances Antigen Presentation and Generation of Central Memory Tumor-specific Cytotoxic T-lymphocytes," Journal of Immunology 32(7):726-736.
Kenter, G. G. et al. (Nov. 5, 2009). "Vaccination against HPV-16 Oncoproteins for Vulvar Intraepithelial Neoplasia," The New England Journal Of Medicine 361(19):1838-1847, 14 pages. (Including Supplemental Material).
Kim, D. et al. (2009, e-pub. Apr. 13, 2009). "Microengineered Platforms for Cell Mechanobiology," Annual Review of Biomedical Engineering 11:203-233.
Lee, L. et al. (Nov. 16, 2012, e-pub. Dec. 12, 2012). "Non-Endocytic Delivery of Functional Engineered Nanoparticles into the Cytoplasm of Live Cells Using a Novel, High-Throughput Microfluidic Device," Nano Letters 12 (12):6322-6327, 34 pages. (Including Supplemental Material).
Li, J. et al. (Jun. 30, 2016, e-pub. May 19, 2016). "The Combination Of Pleurotus Ferulaewater Extract And CpG-ODN Enhances The Immune Responses And Antitumor Efficacy Of HPV Peptides Pulsed Dendritic Cell-Based Vaccine," Vaccine 34(31):3568-3575.
Li, J. et al. (Oct. 31, 2017). "Microfluidic-Enabled Intracellular Delivery of Membrane Impermeable Inhibitors to Study Target Engagement in Human Primary Cells," ACS Chemical Biology 12(12):2970-2974.
Liang, X. et al. (Aug. 20, 2015, e-pub. May 21, 2015). "Rapid and Highly Efficient Mammalian Cell Engineering via Cas9 Protein Transfection," J. Biotech 208:44-53.
Lin, B.K. et al. (Jun. 26, 2013). "Highly Selective Biomechanical Separation of Cancer Cells From Leukocytes Using 1-19 Microfluidic Ratchets and Hydrodynamic Concentrator," Biomicrofluidics 7(3):1-11.
Liu, W. et al. (Jan. 20, 2010). "Compact Biocompatible Quantum Dots Via RAFT-Mediated Synthesis of Imidazole-Based Random Copolymer Ligand," JACS 132(2):472-483, 27 pages.
Liu, Y. et al. (Sep. 19, 2012, e-pub. Jul. 13, 2012). "Spatially Selective Reagent Delivery Into Cancer Cells Using A Two-Layer Microfluidic Culture System," Anal Chim Acta 743(1):125-130, 16 pages.
Liu, Z. et al. (Jul. 28, 2014). "Molecular Imaging in Tracking Tumor Specific Cytotoxic T Lymphocytes (CTLs)," Theranostics 4(10):990-1001.
Loughhead, S.M. et al. (Dec. 1, 2018). "SQZing Cells To Rapidly Generate Antigen Presenting Cells (APC) For Solid Tumor Immune Therapies With Efficient, Scalable Manufacturing," Abstract, Annals Of Oncology 29(Suppl No. 10):1 page, (Abstract No. 38P).
Maratou, E. et al. (Apr. 2007). "Glucose Transporter Expression On The Plasma Membrane Of Resting And Activated White Blood Cells," Eur J Clin Invest 37(4):282-290.
Matthews, B.D. et al. (2006). "Cellular Adaptation to Mechanical Stress: Role of Integrins, Rho, Cytoskeletal Tension And Mechanosensitive lon Channels," Journal of Cell Science 119:508-518.
Moser, B. et al. (Jul. 2011, e-pub. May 15, 2011). "gamma delta T-APCs: A Novel Tool For Immunotherapy?," Cellular And Molecular Life Sciences 68(14):2443-2452.
Murphy, J.S. et al. (Sep. 1, 1956, e-pub May 2004). "Measurement of Wall Shearing Stress in the Boundary Layer by Means of an Evaporating Liquid Film," Journal of Applied Physics 27(9):1097-1103, 9 pages.
Papaioannou, N.E. et al. (2016). "Harnessing the Immune System to Improve Cancer Therapy," Annals of Translational Medicine 4(14):261, 15 pages.
Patel, K.K. et al. (Dec. 1, 2016). "Combination Immunotherapy with NY-ESO-1-Specific CAR+ T Cells with T-Cell Vaccine Improves Anti-Myeloma Effect," Blood Journal 128(22):3366, 1 page (Poster).
Plummer, E. et al. (Mar.-Apr. 2011, e-pub. Sep. 24, 2010). "Viral Nanoparticles and Virus-Like Particles: Platforms for Contemporary Vaccine Design," Wiley Interdiscip Rev Nanomed Nanobiotechnol. 3(2):174-196.
Rughetti, A. et al. (Sep. 2000). "Transfected Human Dendritic Cells to Induce Antitumor Immunity," Gene Therapy 7(17):1458-1466.
Rutella, S. et al. (Sep. 1, 2006). "Tolerogenic Dendritic Cells: Cytokine Modulation Comes of Age," Blood 180(5):1435-1440.
Sercombe, L. et al. (2015, e-pub. Dec. 1, 2015). "Advances and Challenges of Liposome Assisted Drug Delivery," Front Pharmacol. 6:286, 13 pages.
Sharei, A. et al. (2015, e-pub. Apr. 13, 2015). "Ex Vivo Cytosolic Delivery of Functional Macromolecules to Immune Cells," PLOS ONE 10(4):e0118803, 12 pages.
Sharei, A. et al. (Feb. 5, 2013, e-pub. Jan. 22, 2013). "A Vector-Free Mircrofuidic platform for Intracellular Delivery," Proc Natl Acad Sci U.S.A. 110(6):2082-2087.
Sharei, A. et al. (Nov. 7, 2013). "Cell Squeezing as a Robust, Microfluidic Intracellular Delivery Platform," Journal of Visualized Experiments (81):e50980, 9 pages.
Sharei, A. et al. (Oct. 31, 2012). "(483d) Microfluidic Cell Deformation As a Robust, Vector-Free Method for Cytosolic Delivery of Macromolecules," 12AlChE Proceedings Annual Meeting (https://www.aiche.org/conferences/aiche-annual-meeting/2012/proceeding/paper/483d-microfluidic-cell-deformation-robust-vector-free-method-cytosolic-delivery-macromolecules) last visited on Feb. 4, 2021, 8 pages.
Sharei, A.R. (Jun. 26, 2013). "Cell Squeezing: A Vector-Free Microfluidic Platform for Intracellular Delivery of Macromol-

(56) References Cited

OTHER PUBLICATIONS ecules," MIT Thesis (Public, located here: https://dspace.mit.edu/bitstream/handle/1721.1/81688/860804208-MIT.pdf?sequence=2) 165 pages.
Shelby, J.P. et al. (Dec. 9, 2003). "A Microfluidic Model for Single-Cell Capillary Obstruction by Plasmodium Falciparum-Infected Erythrocytes," PNAS 100(25):14618-14622.
Song, A.Y. et al. (2006). "Scientific Basis for the Use of Hypotonic Solutions with Ultrasonic Liposuction," Aesth. Plast. Surg. 30:233-238, 3 pages.
Steinman, R.M. et al. (Apr. 1, 2003). "Tolerogenic Dendritic Cells," Annu. Rev. Immunol. 21:685-711.
Stewart, M.P. et al. (Oct. 12, 2016). "In Vitro and Ex Vitro Strategies for Intracellular Delivery," Nature 538 (7624):183-192, 23 pages.
Suresh, T. et al. (2017). "The Emerging Role of Immunotherapy in Head and Neck Squamous Cell Cancer," in The American Journal of Hematology/Oncology 13(6):20-27, 8 pages.
Szeto, G.L. et al. (May 22, 2015). "Microfluidic Squeezing for Intracellular Antigen Loading in Polyclonal B-Cells as Cellular Vaccines," Scientific Reports 5:10276, 13 pages.
Talarico, L. et al. (Nov. 2017). "Engineered Antigen Presenting T Cells for the Treatment of Solid Tumor Cancers," EMBASE, 32nd Annual Meeting and Pre-Conference Programs of the Society for Immunotherapy of Cancer, SITC 2017, Journal for Immuno Therapy of Cancer 5(Suppl. 2):EMB-619371158, 1 page. (Abstract).
Tsaoir, C. et al. (Jun. 2016). "Scalable Antibody Production from CHO Cell Line of Choice Using Flow Electroporation," Poster, Cell Line Development Jun. 2016, © 2016 MaxCyte, Inc., located at: https://www.maxcyte.com/wp-content/uploads/2017/10/scalable-ab-production-from-cho-cells.pdf, last retrieved on Apr. 2, 2019, 1 page. (Poster).
U.S. Appl. No. 16/769,993, filed Dec. 4, 2018, by Sharei et al. (Copy not submitted herewith pursuant to the waiver of 37 C.F.R. § 1.98(a)(2)(iii) issued by the Office on Sep. 21, 2004.).
U.S. Appl. No. 17/075,116, filed Oct. 20, 2020, by Sharei et al. (Copy not submitted herewith pursuant to the waiver of 37 C.F.R. § 1.98(a)(2)(iii) issued by the Office on Sep. 21, 2004.).
U.S. Appl. No. 17/169,357, filed Feb. 5, 2021, by Godfrini et al. (Copy not submitted herewith pursuant to the waiver of 37 C.F.R. § 1.98(a)(2)(iii) issued by the Office on Sep. 21, 2004.).
U.S. Appl. No. 62/812,225, filed Feb. 28, 2019, by Sharei et al. (Copy not submitted herewith pursuant to the waiver of 37 C.F.R. § 1.98(a)(2)(iii) issued by the Office on Sep. 21, 2004.).
Verma, R. R. et al. (Nov. 2013, e-pub. Sep. 6, 2013). "E6 Protein of Human Papilloma Virus 16 (HPV16) Expressed in *Escherichia coli* Sans a Stretch of Hydrophobic Amino Acids, Enables Purification of GST-[Delta]E6 in the Soluble Form and Retains the Binding Ability to p53," Protein Expression And Purification 92(1):41-47.
Wang, H.L. et al. (Jan. 2014, e-pub. Aug. 3, 2013). "In Vitro And In Vivo Evaluations Of Human Papillomavirus Type 16 (HPV16)-Derived Peptide-Loaded Dendritic Cells (DCs) With A CpG oligodeoxynucleotide (CpG-ODN) Adjuvant As Tumor Vaccines For Immunotherapy Of Cervical Cancer," Gynecologic Oncology 289(1):155-162.
Williams, A.R. et al. (Nov. 5, 1999). "Filtroporation: A Simple, Reliable Technique For Transfection and Macromolecular Loading of Cells in Suspension," Biotechnology and Bioengineering 65(3):341-346.
Written Opinion of the International Searching Authority mailed Jul. 21, 2017, for Patent Application No. PCT/US2017/030933, filed May 3, 2017, 11 pages.
Zarnitsyn, V.G. et al. (2008, e-pub. Nov. 10, 2007). "Electrosonic Ejector Microarray For Drug And Gene Delivery," Biomed Microdevices 10:299-308.
GG Kenter et al., "Supplementary to Vaccination against HPV-16 oncoproteins for vulvar intraepithelial neoplasia", Nov. 5, 2009 (Nov. 5, 2009), p. 1-4, Retrieved from the Internet: URL:https://www.nejm.org/doi/suppl/10.1056/NEJMoa0810097/suppl_file/nejm_kenter_1838sa1.pdf, XP055629060, [retrieved on Oct. 4, 2019].
Leeann Talarico et al, "Engineered antigen presenting T cells for treatment of solid tumor cancers", Proceedings of the AACR Special Conference on Tumor Immunology and Immuotherapy, Sep. 1, 2018 (Sep. 1, 2018).

* cited by examiner

| Groups | TUMOR DOSE | TREATMENT | | | | | | MICE |
|---|---|---|---|---|---|---|---|---|
| | | Vaccination regime | SQZ'd T cells | Dose/mouse | Frequency | Co-injection | Dose/mouse | |
| A | 50K TC-1 | N/A | Untreated | N/A | | | | 10 |
| B | | THERAPEUTIC | E7+CpG SQZ'd | PRIME (5M) BOOST (5M) | Day +4, +7 | None | | |
| C | | | | PRIME (2.5M) BOOST (2.5M) | | | | |
| D | | | | PRIME (5M) BOOST (1M) | | | | |
| E | | | | PRIME (2.5M) BOOST (1M) | | | | |

| groups | | mice | treatment | output |
|---|---|---|---|---|
| A | Untreated | 3 | 5M cells/mouse | **Day +7** Tetramer staining (splenocytes) ICS (splenocytes) |
| B | Endo E7 43-77(Serine) | 5 | Adjuvant for all groups CpG 200 ug (Endo or SQZ'd) | |
| C | SQZ'd E7 43-77(Serine) | 5 | | |
| D | Endo E7 43-77(Cysteine ) | 5 | Antigen for all groups 10 uM E7 SLP +10uM MSA SQZ'd | |
| E | SQZ'd E7 43-77(Cysteine) | 5 | | |

| GROUPS | | # MICE | DOSE |
|---|---|---|---|
| A | Untreated | 3 | Prime 5M cells/mouse |
| B | **LMW** poly I:C+OVA **SQZ'd** | 5 | |
| C | **LMW** poly I:C+OVA **Endo** | 5 | |
| D | **HMW** poly I:C+OVA **SQZ'd** | 5 | |
| E | **HMW** poly I:C+OVA **Endo** | 5 | |
| F | CpG + OVA SQZ'd | 5 | |

| | groups | mice | treatment |
|---|---|---|---|
| A | Untreated | 3 | Prime 5M cells/mouse |
| B | Endo OVA+CpG (200ug/mL) | 5 | |
| C | SQZ'd OVA+CpG (200ug/mL) | 5 | |
| D | Endo OVA+CpG (100ug/mL) | 5 | |
| E | SQZ'd OVA+CpG (100ug/mL) | 5 | |
| F | Endo OVA+CpG (50ug/mL) | 5 | |
| G | SQZ'd OVA+CpG (50ug/mL) | 5 | |

| groups | | mice | treatment |
|---|---|---|---|
| A | Untreated | 3 | 5M cells/mouse |
| B | **Endo** OVA (Day 0) + injection CpG (Day 0) | 5 | |
| C | **SQZ'd** OVA+CpG (Day 0) + injection CpG (Day 0) | 5 | |
| D | **Endo** OVA (Day 0) + injection CpG (Day 1) | 5 | CpG 25 ug/mouse |
| E | **SQZ'd** OVA+CpG (Day 0) + injection CpG (Day 1) | 5 | |
| F | **Endo** OVA (Day 0) + injection CpG (Day 2) | 5 | OVA SQZ'd (400 ug/mL) |
| G | **SQZ'd** OVA+CpG (Day 0) + injection CpG (Day 2) | 5 | |
| H | OVA+CpG SQZ'd (Day 0) | 3 | |

| Groups | Treatment | | | | Mice |
|---|---|---|---|---|---|
| | SQZ'd T cells | Dose/mouse | Co-injection | Dose/mouse | |
| A | Untreated | 5M | N/A | N/A | 10 |
| B | E7 SQZ'd | | CpG | 25 ug | |
| C | | | IFNα | 10K IU | |
| D | E7+CpG SQZ'd | | None | | |
| E | | | CpG | 25 ug | |
| F | | | IFNα | 10K IU | |

| Groups | Treatment | # cells X$10^6$ (T) | TC-1 cells X$10^5$ | # Mice | Treatment |
|---|---|---|---|---|---|
| A | Untreated | 0 | 0.5 | 10 | Day -7 and -14 |
| B | E7+CpG SQZ'd T cells | 5 | | 10 | |
| C | E7+CpG Endo T cells | 5 | | 5 | |
| D | E7 SQZ'd T cells | 5 | | 5 | |
| E | CpG SQZ'd T cells | 5 | | 5 | |
| F | E7+E6+CpG SQZ'd T cells | 5 | | 10 | |
| G | E6+CpG SQZ'd T | 5 | | 9 | |

| Group | # of Mice | T cell Dose | Antigen (SLP) | CpG During SQZ | MSA | Co-Injected CpG |
|---|---|---|---|---|---|---|
| A: No Ag | 10 | n/a | n/a | n/a | n/a | n/a |
| B: CpG Injected | 10 | n/a | n/a | n/a | n/a | 25ug/mouse |
| C: SQZ (SLP Only) | 10 | 5M | 20uM E7 | n/a | 20uM | 25ug/mouse |
| D: SQZ (SLP + CpG) | 8 | 5M | 20uM E7 | 200ug/ml | 20uM | n/a |

| Groups | TUMOR DOSE | TREATMENT | | | | | | MICE |
|---|---|---|---|---|---|---|---|---|
| | | Vaccination regime | SQZ'd T cells | Dose/mouse | Frequency | Co-injection | Dose/mouse | |
| A | 50K TC-1 | N/A | Untreated | N/A | | | | 10 |
| B | | THERAPEUTIC | E7+CpG SQZ'd | 5M | Day +4, +7, +11 | None | | |
| C | | | | | Day +7, +14, +21 | | | |
| D | | | | | Day +7, +14, | | | |

SEQUENCE LISTING

<160> NUMBER OF SEQ ID NOS: 52

<210> SEQ ID NO 1
<211> LENGTH: 10
<212> TYPE: PRT
<213> ORGANISM: Unknown
<220> FEATURE:
<223> OTHER INFORMATION: Human papilloma virus

<400> SEQUENCE: 1

```
Thr Ile His Asp Ile Ile Leu Glu Cys Val
1               5                   10
```

<210> SEQ ID NO 2
<211> LENGTH: 10
<212> TYPE: PRT
<213> ORGANISM: Unknown
<220> FEATURE:
<223> OTHER INFORMATION: Human papilloma virus

<400> SEQUENCE: 2

```
Glu Val Tyr Asp Phe Ala Phe Arg Asp Leu
1               5                   10
```

<210> SEQ ID NO 3
<211> LENGTH: 10
<212> TYPE: PRT
<213> ORGANISM: Unknown
<220> FEATURE:
<223> OTHER INFORMATION: Human papilloma virus

<400> SEQUENCE: 3

```
Tyr Met Leu Asp Leu Gln Pro Glu Thr Thr
1               5                   10
```

<210> SEQ ID NO 4
<211> LENGTH: 9
<212> TYPE: PRT
<213> ORGANISM: Unknown
<220> FEATURE:
<223> OTHER INFORMATION: Human papilloma virus

<400> SEQUENCE: 4

```
Arg Ala His Tyr Asn Ile Val Thr Phe
1               5
```

<210> SEQ ID NO 5
<211> LENGTH: 10
<212> TYPE: PRT
<213> ORGANISM: Artificial Sequence
<220> FEATURE:
<223> OTHER INFORMATION: Synthetic Construct

<400> SEQUENCE: 5

```
Leu Pro Gln Leu Ser Thr Glu Leu Gln Thr
1               5                   10
```

<210> SEQ ID NO 6
<211> LENGTH: 8
<212> TYPE: PRT
<213> ORGANISM: Unknown
<220> FEATURE:
<223> OTHER INFORMATION: Human papilloma virus

<400> SEQUENCE: 6

```
Gln Leu Cys Thr Glu Leu Gln Thr
1               5
```

<210> SEQ ID NO 7
<211> LENGTH: 7
<212> TYPE: PRT
<213> ORGANISM: Unknown
<220> FEATURE:
<223> OTHER INFORMATION: Human papilloma virus

<400> SEQUENCE: 7

Lys Gln Gln Leu Leu Arg Arg
1               5

<210> SEQ ID NO 8
<211> LENGTH: 10
<212> TYPE: PRT
<213> ORGANISM: Artificial Sequence
<220> FEATURE:
<223> OTHER INFORMATION: Synthetic Construct

<400> SEQUENCE: 8

Val Tyr Ser Lys Gln Gln Leu Leu Arg Arg
1               5                   10

<210> SEQ ID NO 9
<211> LENGTH: 10
<212> TYPE: PRT
<213> ORGANISM: Unknown
<220> FEATURE:
<223> OTHER INFORMATION: Human papilloma virus

<400> SEQUENCE: 9

Met His Gly Asp Thr Pro Thr Leu His Glu
1               5                   10

<210> SEQ ID NO 10
<211> LENGTH: 6
<212> TYPE: PRT
<213> ORGANISM: Unknown
<220> FEATURE:
<223> OTHER INFORMATION: Human papilloma virus

<400> SEQUENCE: 10

Gly Gln Ala Glu Pro Asp
1               5

<210> SEQ ID NO 11
<211> LENGTH: 16
<212> TYPE: PRT
<213> ORGANISM: Artificial Sequence
<220> FEATURE:
<223> OTHER INFORMATION: Synthetic Construct

<400> SEQUENCE: 11

Tyr Ser Lys Gln Gln Leu Leu Arg Arg Glu Val Tyr Asp Phe Ala Phe
1               5                   10                  15

<210> SEQ ID NO 12
<211> LENGTH: 7
<212> TYPE: PRT
<213> ORGANISM: Unknown
<220> FEATURE:
<223> OTHER INFORMATION: Human papilloma virus

<400> SEQUENCE: 12

Tyr Cys Lys Gln Gln Leu Leu
1               5

```
<210> SEQ ID NO 13
<211> LENGTH: 8
<212> TYPE: PRT
<213> ORGANISM: Unknown
<220> FEATURE:
<223> OTHER INFORMATION: Human papilloma virus

<400> SEQUENCE: 13

Cys Ile Val Tyr Arg Asp Gly Asn
1               5


<210> SEQ ID NO 14
<211> LENGTH: 15
<212> TYPE: PRT
<213> ORGANISM: Artificial Sequence
<220> FEATURE:
<223> OTHER INFORMATION: Synthetic Construct

<400> SEQUENCE: 14

Ser Ile Val Tyr Arg Asp Gly Asn Pro Tyr Ala Val Ser Asp Lys
1               5                   10                  15


<210> SEQ ID NO 15
<211> LENGTH: 15
<212> TYPE: PRT
<213> ORGANISM: Unknown
<220> FEATURE:
<223> OTHER INFORMATION: Human papilloma virus

<400> SEQUENCE: 15

Asp Leu Tyr Cys Tyr Glu Gln Leu Asn Asp Ser Ser Glu Glu Glu
1               5                   10                  15


<210> SEQ ID NO 16
<211> LENGTH: 20
<212> TYPE: PRT
<213> ORGANISM: Unknown
<220> FEATURE:
<223> OTHER INFORMATION: Human papilloma virus

<400> SEQUENCE: 16

Cys Cys Lys Cys Asp Ser Thr Leu Arg Leu Cys Val Gln Ser Thr His
1               5                   10                  15

Val Asp Ile Arg
            20


<210> SEQ ID NO 17
<211> LENGTH: 20
<212> TYPE: PRT
<213> ORGANISM: Artificial Sequence
<220> FEATURE:
<223> OTHER INFORMATION: Synthetic Construct

<400> SEQUENCE: 17

Ser Ser Lys Ser Asp Ser Thr Leu Arg Leu Ser Val Gln Ser Thr His
1               5                   10                  15

Val Asp Ile Arg
            20


<210> SEQ ID NO 18
<211> LENGTH: 36
<212> TYPE: PRT
<213> ORGANISM: Artificial Sequence
<220> FEATURE:
<223> OTHER INFORMATION: Synthetic Construct
```

```
<400> SEQUENCE: 18

Leu Pro Gln Leu Ser Thr Glu Leu Gln Thr Thr Ile His Asp Ile Ile
1               5                   10                  15

Leu Glu Cys Val Tyr Ser Lys Gln Gln Leu Leu Arg Arg Glu Val Tyr
            20                  25                  30

Asp Phe Ala Phe
        35


<210> SEQ ID NO 19
<211> LENGTH: 25
<212> TYPE: PRT
<213> ORGANISM: Artificial Sequence
<220> FEATURE:
<223> OTHER INFORMATION: Synthetic Construct

<400> SEQUENCE: 19

Gln Leu Cys Thr Glu Leu Gln Thr Thr Ile His Asp Ile Ile Leu Glu
1               5                   10                  15

Cys Val Tyr Cys Lys Gln Gln Leu Leu
            20                  25


<210> SEQ ID NO 20
<211> LENGTH: 25
<212> TYPE: PRT
<213> ORGANISM: Artificial Sequence
<220> FEATURE:
<223> OTHER INFORMATION: Synthetic Construct

<400> SEQUENCE: 20

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25


<210> SEQ ID NO 21
<211> LENGTH: 35
<212> TYPE: PRT
<213> ORGANISM: Artificial Sequence
<220> FEATURE:
<223> OTHER INFORMATION: Synthetic Construct

<400> SEQUENCE: 21

Val Tyr Ser Lys Gln Gln Leu Leu Arg Arg Glu Val Tyr Asp Phe Ala
1               5                   10                  15

Phe Arg Asp Leu Ser Ile Val Tyr Arg Asp Gly Asn Pro Tyr Ala Val
            20                  25                  30

Ser Asp Lys
        35


<210> SEQ ID NO 22
<211> LENGTH: 35
<212> TYPE: PRT
<213> ORGANISM: Artificial Sequence
<220> FEATURE:
<223> OTHER INFORMATION: Synthetic Construct

<400> SEQUENCE: 22

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
```

35

<210> SEQ ID NO 23
<211> LENGTH: 25
<212> TYPE: PRT
<213> ORGANISM: Artificial Sequence
<220> FEATURE:
<223> OTHER INFORMATION: Synthetic Construct

<400> SEQUENCE: 23

Gln Leu Cys Thr Glu Leu Gln Thr Tyr Met Leu Asp Leu Gln Pro Glu
1 5 10 15

Thr Thr Tyr Cys Lys Gln Gln Leu Leu
20 25

<210> SEQ ID NO 24
<211> LENGTH: 35
<212> TYPE: PRT
<213> ORGANISM: Artificial Sequence
<220> FEATURE:
<223> OTHER INFORMATION: Synthetic Construct

<400> SEQUENCE: 24

Gly Gln Ala Glu Pro Asp Arg Ala His Tyr Asn Ile Val Thr Phe Cys
1 5 10 15

Cys Lys Cys Asp Ser Thr Leu Arg Leu Cys Val Gln Ser Thr His Val
20 25 30

Asp Ile Arg
35

<210> SEQ ID NO 25
<211> LENGTH: 35
<212> TYPE: PRT
<213> ORGANISM: Artificial Sequence
<220> FEATURE:
<223> OTHER INFORMATION: Synthetic Construct

<400> SEQUENCE: 25

Gly Gln Ala Glu Pro Asp Arg Ala His Tyr Asn Ile Val Thr Phe Ser
1 5 10 15

Ser Lys Ser Asp Ser Thr Leu Arg Leu Ser Val Gln Ser Thr His Val
20 25 30

Asp Ile Arg
35

<210> SEQ ID NO 26
<211> LENGTH: 20
<212> TYPE: DNA
<213> ORGANISM: Artificial Sequence
<220> FEATURE:
<223> OTHER INFORMATION: Synthetic Construct

<400> SEQUENCE: 26
ggggtcaacg ttgagggggg 20

<210> SEQ ID NO 27
<211> LENGTH: 20
<212> TYPE: DNA
<213> ORGANISM: Artificial Sequence
<220> FEATURE:
<223> OTHER INFORMATION: Synthetic Construct

<400> SEQUENCE: 27
gggggacgat cgtcgggggg 20

<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
ggggacgacg tcgtgggggg g 21

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
tccatgacgt tcctgatgct 20

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
tccatgacgt tcctgacgtt 20

<210> SEQ ID NO 31
<211> LENGTH: 24
<212> TYPE: DNA
<213> ORGANISM: Artificial Sequence
<220> FEATURE:
<223> OTHER INFORMATION: Synthetic Construct

<400> SEQUENCE: 31
tcgtcgtttt gtcgttttgt cgtt 24

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
tcgtcgttgt cgttttgtcg tt 22

<210> SEQ ID NO 33
<211> LENGTH: 23
<212> TYPE: DNA
<213> ORGANISM: Artificial Sequence
<220> FEATURE:
<223> OTHER INFORMATION: Synthetic Construct

<400> SEQUENCE: 33
tcgacgttcg tcgttcgtcg ttc 23

<210> SEQ ID NO 34
<211> LENGTH: 26
<212> TYPE: DNA
<213> ORGANISM: Artificial Sequence
<220> FEATURE:

<223> OTHER INFORMATION: Synthetic Construct

<400> SEQUENCE: 34
tcgcgacgtt cgcccgacgt tcggta 26

<210> SEQ ID NO 35
<211> LENGTH: 22
<212> TYPE: DNA
<213> ORGANISM: Artificial Sequence
<220> FEATURE:
<223> OTHER INFORMATION: Synthetic Construct

<400> SEQUENCE: 35
tcgtcgtttt cggcgcgcgc cg 22

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
tcgtcgtcgt tcgaacgacg ttgat 25

<210> SEQ ID NO 37
<211> LENGTH: 29
<212> TYPE: DNA
<213> ORGANISM: Artificial Sequence
<220> FEATURE:
<223> OTHER INFORMATION: Synthetic Construct

<400> SEQUENCE: 37
tcgcgaacgt tcgccgcgtt cgaacgcgg 29

<210> SEQ ID NO 38
<211> LENGTH: 35
<212> TYPE: PRT
<213> ORGANISM: Artificial Sequence
<220> FEATURE:
<223> OTHER INFORMATION: Synthetic Construct

<400> SEQUENCE: 38

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30

Glu Glu Glu
        35
```

<210> SEQ ID NO 39
<211> LENGTH: 35
<212> TYPE: PRT
<213> ORGANISM: Artificial Sequence
<220> FEATURE:
<223> OTHER INFORMATION: Synthetic Construct

<400> SEQUENCE: 39

```
Leu Tyr Cys Tyr Glu Gln Leu Asn Asp Ser Ser Glu Glu Glu Asp Glu
1               5                   10                  15

Ile Asp Gly Pro Ala Gly Gln Ala Glu Pro Asp Arg Ala His Tyr Asn
            20                  25                  30

Ile Val Thr
        35
```

<210> SEQ ID NO 40
<211> LENGTH: 35
<212> TYPE: PRT
<213> ORGANISM: Artificial Sequence
<220> FEATURE:
<223> OTHER INFORMATION: Synthetic Construct

<400> SEQUENCE: 40

```
Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35
```

<210> SEQ ID NO 41
<211> LENGTH: 35
<212> TYPE: PRT
<213> ORGANISM: Artificial Sequence
<220> FEATURE:
<223> OTHER INFORMATION: Synthetic Construct

<400> SEQUENCE: 41

```
Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
            20                  25                  30

Gln Lys Pro
        35
```

<210> SEQ ID NO 42
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

```
Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30
```

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct

<400> SEQUENCE: 43

```
Leu Pro Gln Leu Cys Thr Glu Leu Gln Thr Thr Ile His Asp Ile Ile
1               5                   10                  15

Leu Glu Cys Val Tyr Cys Lys Gln Gln Leu Leu Arg Arg Glu Val Tyr
            20                  25                  30
```

<210> SEQ ID NO 44
<211> LENGTH: 25
<212> TYPE: PRT
<213> ORGANISM: Artificial Sequence
<220> FEATURE:
<223> OTHER INFORMATION: Synthetic Construct

<400> SEQUENCE: 44

```
Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25
```

<210> SEQ ID NO 45
<211> LENGTH: 26
<212> TYPE: PRT
<213> ORGANISM: Artificial Sequence
<220> FEATURE:
<223> OTHER INFORMATION: Synthetic Construct

<400> SEQUENCE: 45

```
Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile
            20                  25
```

<210> SEQ ID NO 46
<211> LENGTH: 25
<212> TYPE: PRT
<213> ORGANISM: Artificial Sequence
<220> FEATURE:
<223> OTHER INFORMATION: Synthetic Construct

<400> SEQUENCE: 46

```
Asp Lys Cys Leu Lys Phe Tyr Ser Lys Ile Ser Glu Tyr Arg His Tyr
1               5                   10                  15

Cys Tyr Ser Leu Tyr Gly Thr Thr Leu
            20                  25
```

<210> SEQ ID NO 47
<211> LENGTH: 25
<212> TYPE: PRT
<213> ORGANISM: Artificial Sequence
<220> FEATURE:
<223> OTHER INFORMATION: Synthetic Construct

<400> SEQUENCE: 47

```
His Tyr Cys Tyr Ser Leu Tyr Gly Thr Thr Leu Glu Gln Gln Tyr Asn
1               5                   10                  15

Lys Pro Leu Cys Asp Leu Leu Ile Arg
            20                  25
```

<210> SEQ ID NO 48
<211> LENGTH: 32
<212> TYPE: PRT
<213> ORGANISM: Artificial Sequence
<220> FEATURE:
<223> OTHER INFORMATION: Synthetic Construct

<400> SEQUENCE: 48

```
Tyr Gly Thr Thr Leu Glu Gln Gln Tyr Asn Lys Pro Leu Cys Asp Leu
1               5                   10                  15

Leu Ile Arg Cys Ile Asn Cys Gln Lys Pro Leu Cys Pro Glu Glu Lys
            20                  25                  30
```

<210> SEQ ID NO 49
<211> LENGTH: 32
<212> TYPE: PRT
<213> ORGANISM: Artificial Sequence
<220> FEATURE:
<223> OTHER INFORMATION: Synthetic Construct -continued

```
<400> SEQUENCE: 49

Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30


<210> SEQ ID NO 50
<211> LENGTH: 32
<212> TYPE: PRT
<213> ORGANISM: Artificial Sequence
<220> FEATURE:
<223> OTHER INFORMATION: Synthetic Construct

<400> SEQUENCE: 50

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30


<210> SEQ ID NO 51
<211> LENGTH: 24
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 9, 10, 11, 12, 13, 14, 15, 16, 17
<223> OTHER INFORMATION: Xaa = Any Amino Acid

<400> SEQUENCE: 51

Gln Leu Cys Thr Glu Leu Gln Thr Xaa Xaa Xaa Xaa Xaa Xaa Xaa Xaa
1               5                   10                  15

Xaa Tyr Cys Lys Gln Gln Leu Leu
            20


<210> SEQ ID NO 52
<211> LENGTH: 8
<212> TYPE: PRT
<213> ORGANISM: Artificial Sequence
<220> FEATURE:
<223> OTHER INFORMATION: Synthetic Construct

<400> SEQUENCE: 52

Ser Ile Ile Asn Phe Glu Lys Leu
1               5
```

INTRACELLULAR DELIVERY OF BIOMOLECULES TO MODIFY IMMUNE RESPONSE

CROSS REFERENCE TO RELATED APPLICATIONS

This application is a national stage application under 35 U.S.C. S 371 of International Application No. PCT/US2019/021705, filed internationally on Mar. 11, 2019, which claims priority to U.S. Provisional Application No. 62/641,987, filed Mar. 12, 2018, U.S. Provisional Application No. 62/738,941, Sep. 28, 2018, U.S. Provisional Application No. 62/794,516, filed Jan. 18, 2019, which are hereby incorporated by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750322001500SEQLIST.TXT, date recorded: Sep. 10, 2020, size: 14 KB).

FIELD OF THE INVENTION

The present disclosure relates generally to T cells comprising an antigen and/or an adjuvant, methods of manufacturing such T cells, and methods of using such T cells, such as for modulating an immune response in an individual.

BACKGROUND OF THE INVENTION

Immunotherapy can be divided into two main types of interventions, either passive or active. Passive protocols include administration of pre-activated and/or engineered cells, disease-specific therapeutic antibodies, and/or cytokines. Active immunotherapy strategies are directed at stimulating immune system effector functions in vivo. Several current active protocols include vaccination strategies with disease-associated peptides, lysates, or allogeneic whole cells, infusion of autologous DCs as vehicles for tumor antigen delivery, and infusion of immune checkpoint modulators. See Papaioannou, Nikos E., et al. *Annals of translational medicine* 4.14 (2016).

$CD8^+$ cytotoxic T lymphocytes (CTL) and $CD4^+$ helper T (Th) cells stimulated by disease-associated antigens have the potential to target and destroy diseased cells, however, current methods for inducing endogenous T cell responses have faced challenges.

All references cited herein, including patent applications and publications, are incorporated by reference in their entirety.

BRIEF SUMMARY OF THE INVENTION

In some aspects, the invention provides a modified T cell comprising an antigen and an adjuvant, wherein the antigen is exogenous to the modified T cell and comprises an immunogenic epitope, and wherein the adjuvant is present intracellularly. In some embodiments, the invention provides a modified T cell comprising an antigen comprising the amino acid sequence of any one of SEQ ID NOs: 18-25.

In some aspects, the invention provides a modified T cell comprising an antigen and an adjuvant, wherein the antigen comprises an immunogenic epitope, prepared by a process comprising the steps of: a) passing a cell suspension comprising an input T cell through a cell-deforming constriction, wherein a diameter of the constriction is a function of a diameter of the input T cell in the suspension, thereby causing perturbations of the input T cell large enough for the antigen and the adjuvant to pass through to form a perturbed input T cell; and b) incubating the perturbed input T cell with the antigen and the adjuvant for a sufficient time to allow the antigen and the adjuvant to enter the perturbed input T cell; thereby generating the modified T cell comprising the antigen and adjuvant. In some embodiments, the concentration of the antigen incubated with the perturbed input T cell is between about 0.1 μM and about 1 mM and/or the concentration of the adjuvant incubated with the perturbed input T cell is between about 0.1 μM and about 1 mM. In some embodiments, the ratio of the antigen to the adjuvant incubated with the perturbed input T cell is between about 10000:1 to about 1:10000.

In some aspects, the invention provides a modified T cell comprising an antigen and an adjuvant, wherein the antigen comprises an immunogenic epitope, prepared by a process comprising the steps of: a) passing a cell suspension comprising an input T cell comprising the adjuvant through a cell-deforming constriction, wherein a diameter of the constriction is a function of a diameter of the input T cell in the suspension, thereby causing perturbations of the input T cell large enough for the antigen to pass through to form a perturbed input T cell; and b) incubating the perturbed input T cell with the antigen for a sufficient time to allow the antigen to enter the perturbed input T cell, thereby generating the modified T cell comprising the antigen and the adjuvant. In some embodiments, the concentration of the antigen incubated with the perturbed input T cell is between about 0.1 μM and about 1 mM.

In some aspects, the invention provides a modified T cell comprising an antigen and an adjuvant, wherein the antigen comprises an immunogenic epitope, prepared by a process comprising the steps of: a) passing a cell suspension comprising an input T cell comprising the antigen through a cell-deforming constriction, wherein a diameter of the constriction is a function of a diameter of the input T cell in the suspension, thereby causing perturbations of the input T cell large enough for the adjuvant to pass through to form a perturbed input T cell; and b) incubating the perturbed input T cell with the adjuvant for a sufficient time to allow the adjuvant to enter the perturbed input T cell, thereby generating the modified T cell comprising the antigen and the adjuvant. In some embodiments, the concentration of the adjuvant incubated with the perturbed input T cell is between about 0.1 μM and about 1 mM.

In some embodiments, a deforming force is applied to the input T cell as it passes through the constriction, thereby causing the perturbations of the input T cell. In some embodiments, the process further comprises a step of incubating the input T cell and/or the modified T cell with an agent that enhances the viability and/or function of the modified T cell as compared to a corresponding modified T cell prepared without the further incubation step. In some embodiments, the agent is a compound that enhances endocytosis, or acts as a stabilizing agent or a co-factor. In some embodiments, the diameter of the constriction is less than the diameter of the input T cell. In some embodiments, the diameter of the constriction is about 20% to about 99% of the diameter of the input T cell. In some embodiments, the diameter of the constriction is about 20% to about 60% of the diameter of the input T cell.

In some embodiments, the antigen and/or adjuvant are present in the cytosol and/or a vesicle of the modified T cell. In some embodiments, the vesicle is an endosome. In some embodiments, the antigen and/or the adjuvant are present in multiple compartments of the modified T cell. In some embodiments, the antigen or immunogenic epitope is bound to the surface of the modified T cell.

In some embodiments, the adjuvant is a CpG oligodeoxynucleotide (ODN), IFN-α, STING agonists, RIG-I agonists, or poly I:C. In some embodiments, the adjuvant is a CpG ODN. In some embodiments, the CpG ODN is a Class A CpG ODN, a Class B CpG ODN, or a Class C CpG ODN.

In some embodiments, the immunogenic epitope is derived from a disease-associated antigen. In some embodiments, the immunogenic epitope is derived from peptides or mRNA isolated from a diseased cell. In some embodiments, the immunogenic epitope is derived from a non-self antigen. In some embodiments, wherein the immunogenic epitope is derived from a tumor antigen, viral antigen, bacterial antigen, or fungal antigen. In some embodiments, the immunogenic epitope is derived from a human papillomavirus (HPV) antigen. In some embodiments, the HPV is HPV-16 or HPV-18. In some embodiments, the antigen comprises an HLA-A2-restricted peptide derived from HPV E6 and/or E7. In some embodiments, the HLA-A2-restricted peptide comprises the amino acid sequence of any one of SEQ ID NOs: 1-4. In some embodiments, the antigen comprises the amino acid sequence of any one of SEQ ID NOs: 18-25. In some embodiments, the modified T cell comprises a plurality of antigens that comprise a plurality of immunogenic epitopes. In some embodiments, following administration to an individual of the modified T cell comprising the plurality of antigens that comprise the plurality of immunogenic epitopes, none of the plurality of immunogenic epitopes decreases an immune response in the individual to any of the other immunogenic epitopes. In some embodiments, the antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the antigen is a polypeptide comprising an immunogenic peptide epitope and one or more heterologous peptide sequences. In some embodiments, the antigen is a polypeptide comprising an immunogenic peptide epitope that is flanked on the N-terminus and/or the C-terminus by heterologous peptide sequences. In some embodiments, the flanking heterologous peptide sequences are derived from a disease-associated immunogenic peptides. In some embodiments, the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17. In some embodiments, the antigen is capable of being processed into an MHC class I-restricted peptide and/or an MHC class II-restricted peptide.

In some embodiments, the modified T cell comprises the adjuvant at a concentration between about 0.1 μM and about 1 mM. In some embodiments, the modified T cell comprises the antigen at a concentration between about 0.1 μM and about 1 mM. In some embodiments, the ratio of the antigen to the adjuvant is between about 10000:1 to about 1:10000. In some embodiments, the modified T cell comprises a complex comprising: a) the antigen, b) the antigen and at least one other antigen, and/or c) the antigen and the adjuvant.

In some embodiments, the modified T cell further comprises an agent that enhances the viability and/or function of the modified T cell as compared to a corresponding modified T cell that does not comprise the agent. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is a divalent metal cation, glucose, ATP, potassium, glycerol, trehalose, D-sucrose, PEG1500, L-arginine, L-glutamine, or EDTA. In some embodiments, the agent comprises mouse serum albumin (MSA).

In some embodiments, the cells are further modified to increase expression of one or more of co-stimulatory molecules. In some embodiments, the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112. In some embodiments, the cell comprises a nucleic acid that results in increased expression of the one or more co-stimulatory molecules. In some embodiments, the modified T cell comprises a further modification to modulate MHC class I expression. In some embodiments, the modified T cell comprises a further modification to modulate MHC class II expression.

In some embodiments, an innate immune response mounted in an individual in response to administration, in an allogeneic context, of the modified T cells is reduced compared to an innate immune response mounted in an individual in response to administration, in an allogeneic context, of corresponding modified T cells that do not comprise the further modification. In some embodiments, the circulating half-life of the modified T cells in an individual to which they were administered is increased compared to the circulating half-life of corresponding modified T cells that do not comprise the further modification in an individual to which they were administered.

In some embodiments, the modified T cell includes one or more of helper T cells, cytotoxic T cells, memory T cells, or natural killer T cells. In some embodiments, the modified T cell includes one or more of CD3+ T cells, CD4+ T cells, CD8+ T cells, CD45RA+ T cells, CD45RO+ T cells, or γδ-T cells.

In some aspects, the invention provides a composition comprising any of the modified T cells described herein. In some aspects, the invention provides a pharmaceutical composition comprising the modified T cell as described herein and a pharmaceutically acceptable carrier.

In some aspects, the invention provides a method for modulating an immune response in an individual, comprising administering to the individual the modified T cell as described herein, a composition as described herein, or a pharmaceutical composition as described herein.

In some aspects, the invention provides a method for modulating an immune response in an individual, comprising: a) administering a modified T cell comprising an antigen comprising the amino acid sequence of any one of SEQ ID NOs: 18-25 to the individual; and b) administering an adjuvant to the individual.

In some aspects, the invention provides a method for modulating an immune response in an individual, comprising: a) passing a cell suspension comprising an input T cell through a cell-deforming constriction, wherein a diameter of the constriction is a function of a diameter of the input T cell in the suspension, thereby causing perturbations of the input T cell large enough for an antigen and an adjuvant to pass through to form a perturbed input T cell, wherein the antigen comprises an immunogenic epitope; b) incubating the perturbed input T cell with the antigen and the adjuvant for a sufficient time to allow the antigen and the adjuvant to enter the perturbed input T cell, thereby generating a modified T cell comprising the antigen and adjuvant; and c) administering the modified T cell to the individual. In some embodiments, the concentration of the antigen incubated with the perturbed input T cell is between about 0.1 μM and about 1 mM and/or the concentration of the adjuvant incubated with the perturbed input T cell is between about 0.1 μM and about 1 mM. In some embodiments, the ratio of the antigen to the adjuvant incubated with the perturbed input T cell is between about 10000:1 to about 1:10000.

In some aspects, the invention provides a method for modulating an immune response in an individual, comprising: a) passing a cell suspension comprising an input T cell comprising an adjuvant through a cell-deforming constriction, wherein a diameter of the constriction is a function of a diameter of the input T cell in the suspension, thereby causing perturbations of the input T cell large enough for an antigen to pass through to form a perturbed input T cell, wherein the antigen comprises an immunogenic epitope; b) incubating the perturbed input T cell with the antigen for a sufficient time to allow the antigen to enter the perturbed input T cell, thereby generating a modified T cell comprising the antigen and the adjuvant; and c) administering the modified T cell to the individual. In some embodiments, the concentration of the antigen incubated with the perturbed input T cell is between about 0.1 μM and about 1 mM.

In some aspects, the invention provides a method for modulating an immune response in an individual, comprising: a) passing a cell suspension comprising an input T cell comprising an antigen through a cell-deforming constriction, wherein the antigen comprises an immunogenic epitope, wherein a diameter of the constriction is a function of a diameter of the input T cell in the suspension, thereby causing perturbations of the input T cell large enough for an adjuvant to pass through to form a perturbed input T cell; b) incubating the perturbed input T cell with the adjuvant for a sufficient time to allow the adjuvant to enter the perturbed input T cell, thereby generating a modified T cell comprising the antigen and the adjuvant; and c) administering the modified T cell to the individual. In some embodiments, the concentration of the adjuvant incubated with the perturbed input T cell is between about 0.1 μM and about 1 mM. In some embodiments, the modified T cell comprises the antigen at a concentration between about 0.1 μM and about 1 mM. In some embodiments, the modified T cell comprises the adjuvant at a concentration between about 0.1 μM and about 1 mM. In some embodiments, the ratio of the antigen to the adjuvant in the modified T cell is between about 10000:1 and about 1:10000.

In some embodiments, the modified T cell comprises a complex comprising: a) the antigen, b) the antigen and at least one other antigen, and/or c) the antigen and the adjuvant.

In some aspects, the invention provides a method for modulating an immune response in an individual, comprising: a) passing a cell suspension comprising an input T cell through a cell-deforming constriction, wherein a diameter of the constriction is a function of a diameter of the input T cell in the suspension, thereby causing perturbations of the input T cell large enough for an antigen to pass through to form a perturbed input T cell, wherein the antigen comprises an immunogenic epitope; b) incubating the perturbed input T cell with the antigen for a sufficient time to allow the antigen to enter the perturbed input T cell, thereby generating a modified T cell comprising the antigen; c) administering the modified T cell to the individual; and d) administering an adjuvant to the individual. In some embodiments, the concentration of the antigen incubated with the perturbed input T cell is between about 0.1 μM and about 1 mM.

In some embodiments, a deforming force is applied to the input T cell as it passes through the constriction, thereby causing the perturbations of the input T cell. In some embodiments, the method further comprising a step of incubating the input T cell and/or modified T cell with an agent that enhances the viability and/or function of the modified T cell as compared to a corresponding modified T cell prepared without the further incubation step. In some embodiments, the agent is a compound that enhances endocytosis, a stabilizing agent, or a co-factor. In some embodiments of the methods, the immune response is enhanced. In some embodiments, the enhanced immune response is directed towards the antigen. In some embodiments, the diameter of the constriction is less than the diameter of the input T cell. In some embodiments, the diameter of the constriction is about 20% to about 99% of the diameter of the input T cell. In some embodiments, the diameter of the constriction is about 20% to about 60% of the diameter of the input T cell.

In some embodiments, the antigen and/or adjuvant are present in the cytosol and/or a vesicle of the modified T cell. In some embodiments, the vesicle is an endosome. In some embodiments, the antigen and/or the adjuvant are present in multiple compartments of the modified T cell. In some embodiments, the antigen or immunogenic epitope is bound to the surface of the modified T cell.

In some embodiments, the adjuvant is a CpG ODN, IFN-α, STING agonists, RIG-I agonists, or poly I:C. In some embodiments, the adjuvant is a CpG ODN. In some embodiments, the CpG ODN is a Class A CpG ODN, a Class B CpG ODN, or a Class C CpG ODN.

In some embodiments, the immunogenic epitope is derived from a disease-associated antigen. In some embodiments, the immunogenic epitope is derived from peptides or mRNA isolated from a diseased cell. In some embodiments, the immunogenic epitope is derived from a non-self antigen. In some embodiments, the immunogenic epitope is derived from a tumor antigen, viral antigen, bacterial antigen, or fungal antigen. In some embodiments, the immunogenic epitope is derived from a human papillomavirus (HPV) antigen. In some embodiments, the HPV is HPV-16 or HPV-18. In some embodiments, the antigen comprises an HLA-A2-restricted peptide derived from HPV E6 and/or E7. In some embodiments, the HLA-A2-restricted peptide comprises the amino acid sequence of any one of SEQ ID NOs: 1-4. In some embodiments, the antigen comprises the amino acid sequence of any one of SEQ ID NOs: 18-25. In some embodiments, the modified T cell comprises a plurality of antigens that comprise a plurality of immunogenic epitopes. In some embodiments, none of the plurality of immunogenic epitopes decreases an immune response in the individual to any of the other immunogenic epitopes. In some embodiments, the antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the immunogenic peptide epitope fused to the N-terminal flanking polypeptide and/or the C-terminal flanking polypeptide is a non-naturally occurring sequence. In some embodiments, the N-terminal and/or C-terminal flanking polypeptides are derived from an immunogenic synthetic long peptide (SLP). In some embodiments, the N-terminal and/or C-terminal flanking polypeptides are derived from a disease-associated immunogenic SLP. In some embodiments, the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17. In some embodiments, the antigen is capable of being processed into an MHC class I-restricted peptide and/or an MHC class II-restricted peptide.

In some embodiments, the modified T cell further comprises an agent that enhances the viability and/or function of the modified T cell as compared to a corresponding modified T cell that does not comprise the agent. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is a divalent metal cation, glucose, ATP, potassium, glycerol, trehalose, D-sucrose, PEG1500, L-arginine, L-glutamine, or EDTA. In some embodiments, the modified T cell comprises a further modification to modulate MHC class I expression. In some embodiments, the modified T cell comprises a further modification to modulate MHC class II expression.

In some embodiments, an innate immune response mounted in the individual in response to administration, in an allogeneic context, of the modified T cells is reduced compared to an innate immune response mounted in an individual in response to administration, in an allogeneic context, of corresponding modified T cells that do not comprise the further modification. In some embodiments, the circulating half-life of the modified T cells in an individual to which they were administered is increased compared to the circulating half-life of corresponding modified T cells that do not comprise the further modification in an individual to which they were administered.

In some embodiments, the modified T cell includes one or more of helper T cells, cytotoxic T cells, memory T cells, or natural killer T cells. In some embodiments, the modified T cell includes one or more of CD3+ T cells, CD4+ T cells, CD8+ T cells, CD45RA+ T cells, CD45RO+ T cells, or γδ-T cells. In some embodiments, the modified T cell is allogeneic to the individual. In some embodiments, the modified T cell is autologous to the individual. In some embodiments, the individual is pre-conditioned to modulate inflammation and/or an immune response.

In some embodiments, the method further comprises administering to the individual a second adjuvant. In some embodiments, the second adjuvant is IFN-α or a CpG ODN. In some embodiments, the modified T cell and the second adjuvant are administered concurrently or simultaneously. In some embodiments, the modified T cell and the second adjuvant are administered sequentially. In some embodiments, the modified T cell is administered prior to administering the second adjuvant. In some embodiments, the modified T cell is administered following administration of the second adjuvant.

In some embodiments, the modified T cell is administered prior to, concurrently with, or following administration of an immune checkpoint inhibitor. In some embodiments, the immune checkpoint inhibitor is targeted to any one of PD-1, PD-L1, CTLA-4, and TIM-3. In some embodiments, administration of the modified T cell to the individual results in activation and/or expansion of cytotoxic T lymphocytes (CTLs) specific for the antigen. In some embodiments, administration of the modified T cell to the individual results in activation and/or expansion of helper T (Th) cells specific for the antigen. In some embodiments, the amount of the modified T cell administered to the individual is between about $1\times10^6$ and about $1\times10^{12}$ cells.

In some embodiments, the method comprises multiple administrations of the modified T cell. In some embodiments, the time interval between two successive administrations of the modified T cell is between about 1 day and about 30 days.

In some aspects, the invention provides a method for modulating an immune response in an individual, comprising: administering to the individual a modified T cell associated with an antigen, wherein the modified T cell is prepared by a process comprising the steps of:

a) incubating an input T cell with an antigen and/or an adjuvant for a sufficient time to allow the antigen to associate with the cell surface of the input T cell, wherein the antigen comprises an immunogenic epitope, thereby generating a modified T cell associated with the antigen; and b) administering the modified T cell to the individual. In some embodiments, the HPV antigen comprises an amino acid sequence with at least 90% similarity to any one of SEQ ID NOs:18-25. In some embodiments, the HPV antigen comprises the amino acid sequence of SEQ ID NO:23. In some embodiments, the adjuvant is CpG ODN. In some embodiments, the CpG ODN is CpG ODN 1018, CpG ODN 1826 or CpG ODN 2006.

DETAILED DESCRIPTION OF THE INVENTION

Figure 1A:
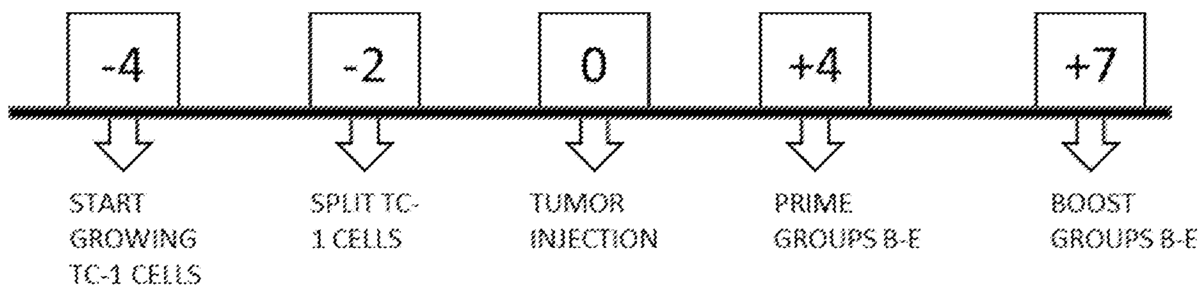
FIG. 1A shows a representative schematic of the treatment groups and schedule.

Antigen presenting cells (APCs) play a key role in inducing endogenous activation of CTLs. In this work, the implementation of the CellSqueeze® platform to engineer T cell APCs ($T_{APC}$) for use in modulating an immune response to various indications, including cancer and infectious disease, is described. By enabling efficient cytosolic delivery of target antigens and/or adjuvant to T cells, this platform has demonstrated the ability to induce effective MHC-I presentation of target antigens and stimulation of CTLs in vivo.

The present application in some aspects provides modified T cells comprising an antigen and an adjuvant, wherein the antigen comprises an immunogenic epitope, and wherein the adjuvant is present intracellularly. In some embodiments, the modified T cells are prepared by a) passing an input T cell through a cell-deforming constriction, wherein a diameter of the constriction is a function of a diameter of the input T cell, thereby causing perturbations of the input T cell large enough for the antigen and the adjuvant to pass through to form a perturbed input T cell; and b) incubating the perturbed input T cell with the antigen and the adjuvant for a sufficient time to allow the antigen and the adjuvant to enter the perturbed input T cell; thereby generating the modified T cell comprising the antigen and adjuvant. Also provided are methods of using the modified T cells for modulating an immune response in an individual, for example, for enhancing an immune response in the individual. In some embodiments, the enhanced immune response is directed towards the antigen. In some embodiments, the cell-deforming constriction is contained in a microfluidic channel, such as any of the microfluidic channels described herein.

In other aspects, there is provided a method of modulating an immune response in an individual comprising administering to the individual a) a modified T cell comprising an antigen, wherein the antigen comprises an immunogenic epitope; and b) an adjuvant. In some embodiments, the modified T cell is prepared by a) passing an input T cell through a cell-deforming constriction, wherein a diameter of the constriction is a function of a diameter of the input T cell, thereby causing perturbations of the input T cell large enough for the antigen to pass through to form a perturbed input T cell; and b) incubating the perturbed input T cell with the antigen for a sufficient time to allow the antigen to enter the perturbed input T cell; thereby generating the modified T cell comprising the antigen. In some embodiments, the immune response is enhanced. In some embodiments, the enhanced immune response is directed towards the antigen. In some embodiments, the cell-deforming constriction is contained in a microfluidic channel, such as any of the microfluidic channels described herein.

General Techniques

The techniques and procedures described or referenced herein are generally well understood and commonly employed using conventional methodology by those skilled in the art, such as, for example, the widely utilized methodologies described in *Molecular Cloning: A Laboratory Manual* (Sambrook et al., $4^{th}$ ed., Cold Spring Harbor Laboratory Press, Cold Spring Harbor, N.Y., 2012); *Current Protocols in Molecular Biology* (F. M. Ausubel, et al. eds., 2003); the series *Methods in Enzymology* (Academic Press, Inc.); *PCR 2: A Practical Approach* (M. J. MacPherson, B. D. Hames and G. R. Taylor eds., 1995); *Antibodies, A Laboratory Manual* (Harlow and Lane, eds., 1988); *Culture of Animal Cells: A Manual of Basic Technique and Specialized Applications* (R. I. Freshney, $6^{th}$ ed., J. Wiley and Sons, 2010); *Oligonucleotide Synthesis* (M. J. Gait, ed., 1984); *Methods in Molecular Biology*, Humana Press; *Cell Biology: A Laboratory Notebook* (J. E. Cellis, ed., Academic Press, 1998); *Introduction to Cell and Tissue Culture* (J. P. Mather and P. E. Roberts, Plenum Press, 1998); *Cell and Tissue Culture: Laboratory Procedures* (A. Doyle, J. B. Griffiths, and D. G. Newell, eds., J. Wiley and Sons, 1993-8); *Handbook of Experimental Immunology* (D. M. Weir and C. C. Blackwell, eds., 1996); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Ausubel et al., eds., J. Wiley and Sons, 2002); *Immunobiology* (C. A. Janeway et al., 2004); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane, Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 2011).

Definitions

For purposes of interpreting this specification, the following definitions will apply and whenever appropriate, terms used in the singular will also include the plural and vice versa. In the event that any definition set forth below conflicts with any document incorporated herein by reference, the definition set forth shall control.

As used herein, the singular form "a", "an", and "the" includes plural references unless indicated otherwise.

It is understood that aspects and embodiments of the invention described herein include "comprising," "consisting," and "consisting essentially of" aspects and embodiments.

The term "about" as used herein refers to the usual error range for the respective value readily known to the skilled person in this technical field. Reference to "about" a value or parameter herein includes (and describes) embodiments that are directed to that value or parameter per se.

The term "pore" as used herein refers to an opening, including without limitation, a hole, tear, cavity, aperture, break, gap, or perforation within a material. In some examples, (where indicated) the term refers to a pore within a surface of the present disclosure. In other examples, (where indicated) a pore can refer to a pore in a cell membrane.

The term "membrane" as used herein refers to a selective barrier or sheet containing pores. The term includes a pliable sheetlike structure that acts as a boundary or lining. In some examples, the term refers to a surface or filter containing pores. This term is distinct from the term "cell membrane".

The term "filter" as used herein refers to a porous article that allows selective passage through the pores. In some examples the term refers to a surface or membrane containing pores.

The term "heterogeneous" as used herein refers to something which is mixed or not uniform in structure or composition. In some examples the term refers to pores having varied sizes, shapes or distributions within a given surface.

The term "homogeneous" as used herein refers to something which is consistent or uniform in structure or composition throughout. In some examples the term refers to pores having consistent sizes, shapes, or distribution within a given surface.

The term "heterologous" as it relates to nucleic acid sequences such as coding sequences and control sequences, denotes sequences that are not normally joined together, and/or are not normally associated with a particular cell. Thus, a "heterologous" region of a nucleic acid construct or a vector is a segment of nucleic acid within or attached to another nucleic acid molecule that is not found in association with the other molecule in nature. For example, a heterologous region of a nucleic acid construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a cell transformed with a construct which is not normally present in the cell would be considered heterologous for purposes of this invention. Allelic variation or naturally occurring mutational events do not give rise to heterologous DNA, as used herein.

The term "heterologous" as it relates to amino acid sequences such as peptide sequences and polypeptide sequences, denotes sequences that are not normally joined together, and/or are not normally associated with a particular cell. Thus, a "heterologous" region of a peptide sequence is a segment of amino acids within or attached to another amino acid molecule that is not found in association with the other molecule in nature. For example, a heterologous region of a peptide construct could include the amino acid sequence of the peptide flanked by sequences not found in association with the amino acid sequence of the peptide in nature. Another example of a heterologous peptide sequence is a construct where the peptide sequence itself is not found in nature (e.g., synthetic sequences having amino acids different as coded from the native gene). Similarly, a cell transformed with a vector that expresses an amino acid construct which is not normally present in the cell would be considered heterologous for purposes of this invention. Allelic variation or naturally occurring mutational events do not give rise to heterologous peptides, as used herein.

The term "exogenous" when used in reference to an agent, such as an antigen or an adjuvant, with relation to a cell refers to an agent delivered from outside the cell (that is, from outside the cell). The cell may or may not have the agent already present, and may or may not produce the agent after the exogenous agent has been delivered.

As used herein, the term "inhibit" may refer to the act of blocking, reducing, eliminating, or otherwise antagonizing the presence, or an activity of, a particular target. Inhibition may refer to partial inhibition or complete inhibition. For example, inhibiting an immune response may refer to any act leading to a blockade, reduction, elimination, or any other antagonism of an immune response. In other examples, inhibition of the expression of a nucleic acid may include, but not limited to reduction in the transcription of a nucleic acid, reduction of mRNA abundance (e.g., silencing mRNA transcription), degradation of mRNA, inhibition of mRNA translation, and so forth.

As used herein, the term "suppress" may refer to the act of decreasing, reducing, prohibiting, limiting, lessening, or otherwise diminishing the presence, or an activity of, a particular target. Suppression may refer to partial suppression or complete suppression. For example, suppressing an immune response may refer to any act leading to decreasing, reducing, prohibiting, limiting, lessening, or otherwise diminishing an immune response. In other examples, suppression of the expression of a nucleic acid may include, but not limited to reduction in the transcription of a nucleic acid, reduction of mRNA abundance (e.g., silencing mRNA transcription), degradation of mRNA, inhibition of mRNA translation, and so forth.

As used herein, the term "enhance" may refer to the act of improving, boosting, heightening, or otherwise increasing the presence, or an activity of, a particular target. For example, enhancing an immune response may refer to any act leading to improving, boosting, heightening, or otherwise increasing an immune response. In one exemplary example, enhancing an immune response may refer to employing an antigen and/or adjuvant to improve, boost, heighten, or otherwise increase an immune response. In other examples, enhancing the expression of a nucleic acid may include, but not limited to increase in the transcription of a nucleic acid, increase in mRNA abundance (e.g., increasing mRNA transcription), decrease in degradation of mRNA, increase in mRNA translation, and so forth.

As used herein, the term "modulate" may refer to the act of changing, altering, varying, or otherwise modifying the presence, or an activity of, a particular target. For example, modulating an immune response may refer to any act leading to changing, altering, varying, or otherwise modifying an immune response. In other examples, modulating the expression of a nucleic acid may include, but not limited to a change in the transcription of a nucleic acid, a change in mRNA abundance (e.g., increasing mRNA transcription), a corresponding change in degradation of mRNA, a change in mRNA translation, and so forth.

As used herein, the term "induce" may refer to the act of initiating, prompting, stimulating, establishing, or otherwise producing a result. For example, inducing an immune response may refer to any act leading to initiating, prompting, stimulating, establishing, or otherwise producing a desired immune response. In other examples, inducing the expression of a nucleic acid may include, but not limited to initiation of the transcription of a nucleic acid, initiation of mRNA translation, and so forth.

The term "homologous" as used herein refers to a molecule which is derived from the same organism. In some examples the term refers to a nucleic acid or protein which is normally found or expressed within the given organism.

The term "polynucleotide" or "nucleic acid" as used herein refers to a polymeric form of nucleotides of any length, either ribonucleotides or deoxyribonucleotides. Thus, this term includes, but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and phosphorothioates, and thus can be an oligodeoxynucleoside phosphoramidate (P—NH2) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present invention, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

As used herein, the term "adjuvant" refers to a substance which directly or indirectly modulates and/or engenders an immune response. Generally, the adjuvant is administered in conjunction with an antigen to effect enhancement of an immune response to the antigen as compared to antigen alone. Various adjuvants are described herein.

The terms "CpG oligodeoxynucleotide" and "CpG ODN" refer to DNA molecules containing a dinucleotide of cytosine and guanine separated by a phosphate (also referred to herein as a "CpG" dinucleotide, or "CpG"). The CpG ODNs of the present disclosure contain at least one unmethylated CpG dinucleotide. That is, the cytosine in the CpG dinucleotide is not methylated (i.e., is not 5-methylcytosine). CpG ODNs may have a partial or complete phosphorothioate (PS) backbone.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

For any of the structural and functional characteristics described herein, methods of determining these characteristics are known in the art.

Modified T Cells

In certain aspects, there is provided a modified T cell comprising an antigen and an adjuvant, wherein the antigen is exogenous to the modified T cell and comprises an immunogenic epitope, and wherein the adjuvant is present intracellularly. Exogenous antigens are one or more antigens from a source outside the T cell introduced into a T cell to be modified, and include antigens that may be present in the T cell (that is, are endogenous), either before or after introduction of the exogenous antigen, and as such can thus be produced by the T cell (e.g., encoded by the genome of the T cell). For example, in some embodiments, the modified T cell comprises two pools of an antigen, a first pool comprising an endogenous source of the antigen, and a second pool comprising an exogenous source of the antigen produced outside of and introduced into the T cell to be modified. In some embodiments, the antigen is ectopically expressed or overexpressed in a disease cell in an individual, and the modified T cell is derived from the individual and comprises an exogenous source of the antigen, or an immunogenic epitope contained therein, produced outside of and introduced into the T cell to be modified. In some embodiments, the antigen is a neoantigen (e.g., an altered-self protein or portion thereof) comprising a neoepitope, and the modified T cell comprises an exogenous source of the antigen, or a fragment thereof comprising the neoepitope, produced outside of and introduced into the T cell to be modified. In some embodiments, the adjuvant is exogenous to the modified T cell. In some embodiments, the antigen and/or the adjuvant are present in multiple compartments of the modified T cell. In some embodiments, the antigen and/or adjuvant are present in the cytosol and/or a vesicle of the modified T cell. In some embodiments, the vesicle is an endosome. In some embodiments, the antigen or immunogenic epitope is bound to the surface of the modified T cell.

In some embodiments, the modified T cell includes one or more of helper T cells, cytotoxic T cells, memory T cells, or natural killer T cells. In some embodiments, the modified T cell includes one or more of CD3+ T cells, CD4+ T cells, CD8+ T cells, CD45RA+ T cells, CD45RO+ T cells, or γδ-T cells.

In certain aspects, there is provided a modified T cell comprising an antigen comprising the amino acid sequence of any one of SEQ ID NOs: 18-25. In some embodiments, the antigen is present in multiple compartments of the modified T cell. In some embodiments, the antigen is present in the cytosol and/or a vesicle of the modified T cell. In some embodiments, the vesicle is an endosome. In some embodiments, the antigen or an immunogenic epitope contained therein is bound to the surface of the modified T cell. In some embodiments, the modified T cell includes one or more of helper T cells, cytotoxic T cells, memory T cells, and natural killer T cells. In some embodiments, the modified T cell includes one or more of CD3+ T cells, CD4+ T cells, CD8+ T cells, CD45RA+ T cells, CD45RO+ T cells, and γδ-T cells. In some embodiments, the modified T cell further comprises an adjuvant.

In some embodiments, according to any of the modified T cells described herein, the modified T cell comprises an adjuvant. In some embodiments, the adjuvant is a CpG oligodeoxynucleotide (ODN), IFN-α, STING agonists, RIG-I agonists, or poly I:C. In some embodiments, the adjuvant is a CpG ODN. In some embodiments, the CpG ODN is no greater than about 50 (such as no greater than about any of 45, 40, 35, 30, 25, 20, or fewer) nucleotides in length. In some embodiments, the CpG ODN is a Class A CpG ODN, a Class B CpG ODN, or a Class C CpG ODN. In some embodiments, the CpG ODN comprises the nucleotide sequence of any one of SEQ ID NOs: 26-37. In some embodiments, the CpG ODN comprises the nucleotide sequence of SEQ ID NO: 30. In some embodiments, the CpG ODN comprises the nucleotide sequence of SEQ ID NO: 31. In some embodiments, the modified T cell comprises a plurality of different CpG ODNs. For example, in some embodiments, the modified T cell comprises a plurality of different CpG ODNs selected from among Class A, Class B, and Class C CpG ODNs.

In some embodiments, the adjuvant is CpG ODN, LPS, IFN-α, STING agonists, RIG-I agonists, poly I:C, R837, R848, a TLR3 agonist, a TLR4 agonist or a TLR 9 agonist. In particular embodiments, the adjuvant is a CpG ODN. In some embodiments, the adjuvant is a CpG ODN. In some embodiments, the CpG ODN is a Class A CpG ODN, a Class B CpG ODN, or a Class C CpG ODN. In some embodiments, the CpG ODN adjuvant comprise of a selection from the group of CpG ODN 1018, CpG ODN 1585, CpG ODN 2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03. In some embodiments, the CpG ODN adjuvant is CpG ODN 1826 (TCCATGACGTTCCTGACGTT SEQ ID NO:30) or CpG ODN 2006 (also known as CpG ODN 7909) (TCGTCGTTTTGTCGTTTTGTCGTT; SEQ ID NO:31) oligonucleotide. In some embodiments, the adjuvant is CpG ODN 7909. In some embodiments, the RIG-I agonist comprises polyinosinic:polycytidylic acid (polyI:C). Multiple adjuvants can also be used in conjunction with antigens to enhance the elicitation of immune response. In some embodiments, the modified T cell comprises more than one adjuvant. Multiple adjuvants can also be used in conjunction with antigens to enhance the elicitation of immune response. In some embodiments, the modified T cell comprises more than one adjuvant. In some embodiments, the modified T cell comprises any combination of the adjuvants CpG ODN, LPS, IFN-α, STING agonists, RIG-I agonists, poly I:C, R837, R848, a TLR3 agonist, a TLR4 agonist or a TLR 9 agonist.

In some embodiments, according to any of the modified T cells described herein, the modified T cell comprises an antigen comprising an immunogenic epitope. In some embodiments, the immunogenic epitope is derived from a disease-associated antigen. In some embodiments, the immunogenic epitope is derived from peptides or mRNA isolated from a diseased cell. In some embodiments, the immunogenic epitope is derived from a protein ectopically expressed or overexpressed in a diseased cell. In some embodiments, the immunogenic epitope is derived from a neoantigen, e.g., a cancer-associated neoantigen. In some embodiments, the immunogenic epitope comprises a neoepitope, e.g., a cancer-associated neoepitope. In some embodiments, the immunogenic epitope is derived from a non-self antigen. In some embodiments, the immunogenic epitope is derived from a mutated or otherwise altered self antigen. In some embodiments, the immunogenic epitope is derived from a tumor antigen, viral antigen, bacterial antigen, or fungal antigen. In some embodiments, the antigen comprises an immunogenic epitope fused to heterologous peptide sequences. In some embodiments, the antigen comprises a plurality of immunogenic epitopes. In some embodiments, some of the plurality of immunogenic epitopes are derived from the same source. For example, in some embodiments, some of the plurality of immunogenic epitopes are derived from the same viral antigen. In some embodiments, all of the plurality of immunogenic epitopes are derived from the same source. In some embodiments, none of the plurality of immunogenic epitopes are derived from the same source. In some embodiments, the modified T cell comprises a plurality of different antigens.

In some embodiments, according to any of the antigens comprising an immunogenic epitope described herein, the antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the immunogenic peptide epitope fused to the N-terminal flanking polypeptide and/or the C-terminal flanking polypeptide is a non-naturally occurring sequence. In some embodiments, the N-terminal and/or C-terminal flanking polypeptides are derived from an immunogenic synthetic long peptide (SLP). In some embodiments, the N-terminal and/or C-terminal flanking polypeptides are derived from a disease-associated immunogenic SLP. In some embodiments, the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17.

In some embodiments, according to any of the antigens comprising an immunogenic epitope described herein, the antigen or immunogenic epitope contained therein is derived from a human papillomavirus (HPV) antigen. In some embodiments, the antigen or immunogenic epitope contained therein is derived from any of HPV-16, 18, 26, 31, 33, 35, 39, 45, 51, 52, 53, 56, 58, 59, 66, 68, 73, and 82. In some embodiments, the antigen or immunogenic epitope contained therein is derived from an HPV-16 antigen or an HPV-18 antigen. In further embodiments, the antigen or immunogenic epitope contained therein is derived from an HPV E6 antigen (e.g., an HPV-16 or HPV-18 E6 antigen) or an HPV E7 antigen (e.g., an HPV-16 or HPV-18 E7 antigen). In some embodiments, the antigen comprises an HLA-A2-restricted peptide derived from HPV E6 and/or E7. In some embodiments, the antigen comprises a fragment of an HPV-16 E6 protein between residues 29 and 38 (i.e., HPV-16 $E6_{29-38}$). In some embodiments, the antigen comprises a fragment of an HPV-16 E6 protein between residues 48 and 57 (i.e., HPV-16 $E6_{48-57}$). In some embodiments, the antigen comprises a fragment of an HPV-16 E7 protein between residues 11 and 20 (i.e., HPV-16 $E7_{11-20}$). In some embodiments, the antigen comprises a fragment of an HPV-16 E7 protein between residues 49 and 57 (i.e., HPV-16 $E7_{4957}$). In some embodiments, the antigen comprises the amino acid sequence of any one of SEQ ID NOs: 1-4. In some embodiments, the antigen comprises the amino acid sequence of any one of SEQ ID NOs: 1-4 flanked with an N-terminal polypeptide comprising the amino acid sequence of any one of SEQ ID NOs: 5-10 and a C-terminal polypeptide comprising the amino acid sequence of any one of SEQ ID NOs: 11-17. In some embodiments, the antigen comprises the amino acid sequence of any one of SEQ ID NOs: 18-25.

In some embodiments, according to any of the antigens comprising an immunogenic epitope described herein, the antigen or immunogenic epitope contained therein is derived from a human cytomegalovirus (HCMV) antigen. In some embodiments, the antigen or immunogenic epitope contained therein is derived from any of strains Merlin, Toledo, Davis, Esp, Kerr, Smith, TB40E, TB40F, AD169 or Towne HCMV. In some embodiments, the antigen or immunogenic epitope contained therein is derived from a strain AD169 HCMV antigen or a strain Merlin HCMV antigen. In further embodiments, the antigen or immunogenic epitope contained therein is derived from pUL48, pUL47, pUL32, pUL82, pUL83, and pUL99, pUL69, pUL25, pUL56, pUL94, pUL97, pUL144 or pUL128. In some embodiments, the antigen comprises an HLA-A2-restricted peptide derived from HCMV pUL83.

In some embodiments, according to any of the antigens comprising an immunogenic epitope described herein, the antigen is capable of being processed into an MHC class I-restricted peptide and/or an MHC class II-restricted peptide. In some embodiments, the antigen is capable of being processed into an MHC class I-restricted peptide. In some embodiments, the antigen is capable of being processed into an MHC class II-restricted peptide. In some embodiments, the antigen comprises a plurality of immunogenic epitopes, and is capable of being processed into an MHC class I-restricted peptide and an MHC class II-restricted peptide. In some embodiments, some of the plurality of immunogenic epitopes are derived from the same source. In some embodiments, all of the plurality of immunogenic epitopes are derived from the same source. In some embodiments, none of the plurality of immunogenic epitopes are derived from the same source.

In some embodiments, according to any of the modified T cells described herein, the modified T cell comprises a plurality of antigens that comprise a plurality of immunogenic epitopes. In some embodiments, following administration to an individual of the modified T cell comprising the plurality of antigens that comprise the plurality of immunogenic epitopes, none of the plurality of immunogenic epitopes decreases an immune response in the individual to any of the other immunogenic epitopes.

In some embodiments, according to any of the modified T cells described herein, the modified T cell comprises an antigen and an adjuvant. In some embodiments, the modified T cell comprises the adjuvant at a concentration between about 1 pM and about 10 mM. In some embodiments, the modified T cell comprises the adjuvant at a concentration between about 0.1 μM and about 10 mM. For example, in some embodiments, the concentration of adjuvant in the modified T cell is any of less than about 1 pM, about 10 pM, about 100 pM, about 1 nM, about 10 nM, about 100 nM, about 1 μM, about 10 μM, about 100 μM, about 1 mM or about 10 mM. In some embodiments, the concentration of adjuvant in the modified T cell is greater than about 10 mM. In some embodiments, the concentration of the antigen in the modified T cell is any of between about 1 pM and about 10 pM, between about 10 pM and about 100 pM, between about 100 pM and about 1 nM, between about 1 nM and about 10 nM, between about 10 nM and about 100 nM, between about 100 nM and about 1 μM, between about 1 μM and about 10 μM, between about 10 μM and about 100 μM, between about 100 μM and about 1 mM, or between 1 mM and about 10 mM. In some embodiments, the molar ratio of antigen to adjuvant in the modified T cell is any of between about 10000:1 to about 1:10000. For example, in some embodiments, the molar ratio of the antigen to adjuvant in the modified T cell is about any of 10000:1, about 1000:1, about 200:1, about 100:1, about 10:1, about 1:1, about 1:10, about 1:100, about 1:1000, or about 1:10000. In some embodiments, the molar ratio of the antigen to adjuvant in the modified T cell is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000. In some embodiments, the modified T cell comprises a complex comprising: a) the antigen, b) the antigen and at least one other antigen, and/or c) the antigen and the adjuvant.

In some embodiments, according to any of the modified T cells described herein, the modified T cell further comprises an agent that enhances the viability and/or function of the modified T cell as compared to a corresponding modified T cell that does not comprise the agent. In some embodiments, the agent is a stabilizing agent or a co-factor. In some embodiments, the agent is albumin. In some embodiments, the albumin is mouse, bovine, or human albumin. In some embodiments, the agent is a divalent metal cation, glucose, ATP, potassium, glycerol, trehalose, D-sucrose, PEG1500, L-arginine, L-glutamine, or EDTA.

In some embodiments according to any one of the methods or compositions described herein, the modified T cell further comprises an agent that enhances the viability and/or function of the modified T cell as compared to a corresponding plurality of the modified T cell that does not comprise the agent. In some embodiments, the modified T cell further comprises an agent that enhances the viability and/or function of the modified T cell upon freeze-thaw cycle as compared to a corresponding the modified T cell that does not comprise the agent. In some embodiments, the agent is a cyropreservation agent and/or a hypothermic preservation agent. In some embodiments, neither the cyropreservation agent nor the hypothermic preservation agent cause more than 10% or 20% of cell death in the modified T cell comprising the agent compared to a corresponding modified T cell that does not comprise the agent before any freeze-thaw cycles. In some embodiments, at least about 70%, about 80%, or about 90% of the modified T cells are viable after up to 1, 2, 3, 4, 5 freeze-thaw cycles. In some embodiments, the agent is a compound that enhances endocytosis, a stabilizing agent or a co-factor. In some embodiments, the agent is albumin. In some embodiments, the albumin is mouse, bovine, or human albumin. In some embodiments, the agent is human albumin. In some embodiments, the agent is one or more of: a divalent metal cation, glucose, ATP, potassium, glycerol, trehalose, D-sucrose, PEG1500, L-arginine, L-glutamine, or EDTA. In some embodiments, the divalent metal cation is one more of $Mg^{2+}$, $Zn^{2+}$ or $Ca^{2+}$. In some embodiments, the agent is one or more of: sodium pyruvate, adenine, trehalose, dextrose, mannose, sucrose, human serum albumin (HSA), DMSO, HEPES, glycerol, glutathione, inosine, dibasic sodium phosphate, monobasic sodium phosphate, sodium metal ions, potassium metal ions, magnesium metal ions, chloride, acetate, gluoconate, sucrose, potassium hydroxide, or sodium hydroxide. In some embodiments, the agent is one or more of: Sodium pyruvate, adenine, Rejuvesol®, trehalose, dextrose, mannose, sucrose, human serum albumin (HSA), PlasmaLyte®, DMSO, Cryostor® CS2, Cryostor® CS5, Cryostor® CS10, Cryostor® CS15, HEPES, glycerol, glutathione, HypoTherosol®.

In some embodiments, according to any of the modified T cells described herein, the modified T cell comprises a further modification. In some embodiments, the modified T cell comprises a further modification to modulate MHC class I expression. In some embodiments, the modified T cell comprises a further modification to decrease MHC class I expression. In some embodiments, the modified T cell comprises a further modification to increase MHC class I expression. In some embodiments, the modified T cell comprises a further modification to modulate MHC class II expression. In some embodiments, the modified T cell comprises a further modification to decrease MHC class II expression. In some embodiments, the modified T cell comprises a further modification to increase MHC class II expression. In some embodiments, an innate immune response mounted in an individual in response to administration, in an allogeneic context, of the modified T cells is reduced compared to an innate immune response mounted in an individual in response to administration, in an allogeneic context, of corresponding modified T cells that do not comprise the further modification. In some embodiments, the circulating half-life of the modified T cells in an individual to which they were administered is increased compared to the circulating half-life of corresponding modified T cells that do not comprise the further modification in an individual to which they were administered.

In certain aspects, there is provided a modified T cell comprising an antigen comprising the amino acid sequence of any one of SEQ ID NOs: 18-25. In some embodiments, the antigen is present in multiple compartments of the modified T cell. In some embodiments, the antigen is present in the cytosol and/or a vesicle of the modified T cell. In some embodiments, the vesicle is an endosome. In some embodiments, the antigen or an immunogenic epitope contained therein is bound to the surface of the modified T cell. In some embodiments, the modified T cell includes one or more of helper T cells, cytotoxic T cells, memory T cells, or natural killer T cells. In some embodiments, the modified T cell includes one or more of CD3+ T cells, CD4+ T cells, CD8+ T cells, CD45RA+ T cells, CD45RO+ T cells, or γδ-T cells. In some embodiments, the modified T cell further comprises an adjuvant. In some embodiments, the modified T cell is prepared by a process comprising the steps of: a) passing a cell suspension comprising an input T cell through a cell-deforming constriction, wherein a diameter of the constriction is a function of a diameter of the input T cell in the suspension, thereby causing perturbations of the input T cell large enough for the antigen to pass through to form a perturbed input T cell; and b) incubating the perturbed input T cell with the antigen for a sufficient time to allow the antigen to enter the perturbed input T cell; thereby generating the modified T cell comprising the antigen. In some embodiments, the concentration of the antigen incubated with the perturbed input T cell is between about 1 pM-10 mM. In some embodiments, the modified T cell further comprises an adjuvant, such as any of the adjuvants described herein.

In certain aspects, there is provided a modified T cell comprising an antigen and an adjuvant, wherein the antigen comprises an immunogenic epitope, prepared by a process comprising the steps of: a) passing a cell suspension comprising an input T cell through a cell-deforming constriction, wherein a diameter of the constriction is a function of a diameter of the input T cell in the suspension, thereby causing perturbations of the input T cell large enough for the antigen and the adjuvant to pass through to form a perturbed input T cell; and b) incubating the perturbed input T cell with the antigen and the adjuvant for a sufficient time to allow the antigen and the adjuvant to enter the perturbed input T cell; thereby generating the modified T cell comprising the antigen and adjuvant. In some embodiments, the concentration of the antigen incubated with the perturbed input T cell is between about 1 pM-10 mM and/or the concentration of the adjuvant incubated with the perturbed input T cell is between about 1 pM-10 mM. In some embodiments, the concentration of the antigen incubated with the perturbed input T cell is between about 0.1 μM-10 mM and/or the concentration of the adjuvant incubated with the perturbed input T cell is between about 0.1 μM-10 mM. In some embodiments, the ratio of the antigen to the adjuvant incubated with the perturbed input T cell is between about 10000:1 to about 1:10000.

In certain aspects, there is provided a modified T cell comprising an antigen and an adjuvant, wherein the antigen comprises an immunogenic epitope, prepared by a process comprising the steps of: a) passing a cell suspension comprising an input T cell comprising the adjuvant through a cell-deforming constriction, wherein a diameter of the constriction is a function of a diameter of the input T cell in the suspension, thereby causing perturbations of the input T cell large enough for the antigen to pass through to form a perturbed input T cell; and b) incubating the perturbed input T cell with the antigen for a sufficient time to allow the antigen to enter the perturbed input T cell, thereby generating the modified T cell comprising the antigen and the adjuvant. In some embodiments, the concentration of the antigen incubated with the perturbed input T cell is between about 1 pM-10 mM.

In certain aspects, there is provided a modified T cell comprising an antigen and an adjuvant, wherein the antigen comprises an immunogenic epitope, prepared by a process comprising the steps of: a) passing a cell suspension comprising an input T cell comprising the antigen through a cell-deforming constriction, wherein a diameter of the constriction is a function of a diameter of the input T cell in the suspension, thereby causing perturbations of the input T cell large enough for the adjuvant to pass through to form a perturbed input T cell; and b) incubating the perturbed input T cell with the adjuvant for a sufficient time to allow the adjuvant to enter the perturbed input T cell, thereby generating the modified T cell comprising the antigen and the adjuvant. In some embodiments, the concentration of the adjuvant incubated with the perturbed input T cell is between about 1 pM-10 mM.

The modified T cells described herein in some embodiments are prepared by a process employing a cell-deforming constriction through which an input T cell is passed. In some embodiments, the diameter of the constriction is less than the diameter of the input T cell. In some embodiments, the diameter of the constriction is about 20% to about 99% of the diameter of the input T cell. In some embodiments, the diameter of the constriction is about 20% to about 60% of the diameter of the input T cell. In some embodiments, the cell-deforming constriction is contained in a microfluidic channel, such as any of the microfluidic channels described herein. The microfluidic channel may be contained in any of the microfluidic devices described herein, such as described in the section titled Microfluidic Devices below. Thus, in some embodiments, according to any of the modified T cells described herein prepared by a process employing a microfluidic channel including a cell-deforming constriction through which an input T cell is passed, the process comprises passing the input T cell through a microfluidic channel including a cell-deforming constriction contained in any of the microfluidic systems described herein. In some embodiments, a deforming force is applied to the input T cell as it passes through the constriction, thereby causing the perturbations of the input T cell.

Input T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments of the present invention, any number of T cell lines available in the art may be used. In some embodiments of the present invention, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as $Ca^{2+}$-free, $Mg^{2+}$-free PBS, PlasmaLyte A, or other saline solutions with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, $CD45RO^+$ T cells, and γδ-T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In some embodiments, the time period ranges from 30 minutes to 36 hours or longer and all integer values there between. In some embodiments, the time period is at least one, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such as in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In some embodiments, it may be desirable to perform the selection procedure and use the "unselected" cells in the activation and expansion process (negative selection). "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD 14, CD20, CD11b, CD 16, HLA-DR, and CD8. In some embodiments, it may be desirable to enrich for or positively select for regulatory T cells which typically express $CD4^+$, $CD25^+$, CD62Lhi, $GITR^+$, and $FoxP3^+$. Alternatively, in some embodiments, T regulatory cells are depleted by anti-CD25 conjugated beads or other similar methods of selection.

For isolation of a desired population of cells by positive or negative selection, the concentration of cells and surface (e.g., particles such as beads) can be varied. In some embodiments, it may be desirable to significantly decrease the volume in which beads and cells are mixed together (i.e., increase the concentration of cells), to ensure maximum contact of cells and beads. For example, in some embodiments, a concentration of about 2 billion cells/mL is used. In some embodiments, a concentration of about 1 billion cells/mL is used. In some embodiments, greater than about 100 million cells/mL is used. In some embodiments, a concentration of cells of about any of 10, 15, 20, 25, 30, 35, 40, 45, or 50 million cells/mL is used. In some embodiments, a concentration of cells of about any of 75, 80, 85, 90, 95, or 100 million cells/mL is used. In some embodiments, a concentration of about 125 or about 150 million cells/mL is used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

Compositions

In certain aspects, there is provided a composition (e.g., a pharmaceutical composition) comprising a modified T cell comprising an antigen and an adjuvant according to any of the embodiments described herein. In some embodiments, the composition is a pharmaceutical composition comprising the modified T cell and a pharmaceutically acceptable carrier.

Methods for Modulating an Immune Response

In certain aspects, there is provided a method for modulating an immune response in an individual, comprising administering to the individual a modified T cell according to any of the embodiments described herein, a composition according to any of the embodiments described herein, or a pharmaceutical composition according to any of the embodiments described herein.

In certain aspects, there is provided a method for modulating an immune response in an individual, comprising: a) passing a cell suspension comprising an input T cell through a cell-deforming constriction, wherein a diameter of the constriction is a function of a diameter of the input T cell in the suspension, thereby causing perturbations of the input T cell large enough for an antigen and an adjuvant to pass through to form a perturbed input T cell, wherein the antigen comprises an immunogenic epitope; b) incubating the perturbed input T cell with the antigen and the adjuvant for a sufficient time to allow the antigen and the adjuvant to enter the perturbed input T cell, thereby generating a modified T cell comprising the antigen and adjuvant; and c) administering the modified T cell to the individual. In some embodiments, the concentration of the antigen incubated with the perturbed input T cell is between about 1 pM-10 mM and/or the concentration of the adjuvant incubated with the perturbed input T cell is between about 1 pM-10 mM. In some embodiments, the ratio of the antigen to the adjuvant incubated with the perturbed input T cell is between about 10000:1 to about 1:10000. In some embodiments, the concentration of the adjuvant incubated with the perturbed input T cell is between about 0.1 μM and about 10 mM. For example, in some embodiments, the concentration of adjuvant incubated with the perturbed T cell is any of less than about 1 pM, about 10 pM, about 100 pM, about 1 nM, about 10 nM, about 100 nM, about 1 μM, about 10 μM, about 100 μM, about 1 mM or about 10 mM. In some embodiments, the concentration of adjuvant incubated with the perturbed T cell is greater than about 10 mM. In some embodiments, the concentration of the antigen incubated with the perturbed T cell is any of between about 1 pM and about 10 pM, between about 10 pM and about 100 pM, between about 100 pM and about 1 nM, between about 1 nM and about 10 nM, between about 10 nM and about 100 nM, between about 100 nM and about 1 μM, between about 1 μM and about 10 μM, between about 10 μM and about 100 μM, between about 100 μM and about 1 mM, or between 1 mM and about 10 mM. In some embodiments, the molar ratio of antigen to adjuvant incubated with the perturbed T cell is any of between about 10000:1 to about 1:10000. For example, in some embodiments, the molar ratio of the antigen to adjuvant incubated with the perturbed T cell is about any of 10000:1, about 1000:1, about 100:1, about 10:1, about 1:1, about 1:10, about 1:100, about 1:1000, or about 1:10000. In some embodiments, the molar ratio of the antigen to adjuvant incubated with the perturbed T cell is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000. In some embodiments, the antigen and/or adjuvant is encapsulated in a nanoparticle.

In certain aspects, there is provided a method for modulating an immune response in an individual, comprising: a) passing a cell suspension comprising an input T cell comprising an adjuvant through a cell-deforming constriction, wherein a diameter of the constriction is a function of a diameter of the input T cell in the suspension, thereby causing perturbations of the input T cell large enough for an antigen to pass through to form a perturbed input T cell, wherein the antigen comprises an immunogenic epitope; b) incubating the perturbed input T cell with the antigen for a sufficient time to allow the antigen to enter the perturbed input T cell, thereby generating a modified T cell comprising the antigen and the adjuvant; and c) administering the modified T cell to the individual. In some embodiments, the concentration of the antigen incubated with the perturbed input T cell is between about 1 pM-10 mM. In some embodiments, the antigen is encapsulated in a nanoparticle.

In certain aspects, there is provided a method for modulating an immune response in an individual, comprising: a) passing a cell suspension comprising an input T cell comprising an antigen through a cell-deforming constriction, wherein the antigen comprises an immunogenic epitope, wherein a diameter of the constriction is a function of a diameter of the input T cell in the suspension, thereby causing perturbations of the input T cell large enough for an adjuvant to pass through to form a perturbed input T cell; b) incubating the perturbed input T cell with the adjuvant for a sufficient time to allow the adjuvant to enter the perturbed input T cell, thereby generating a modified T cell comprising the antigen and the adjuvant; and c) administering the modified T cell to the individual. In some embodiments, the concentration of the adjuvant incubated with the perturbed input T cell is between about 1 pM-10 mM. In some embodiments, the adjuvant is encapsulated in a nanoparticle.

In some embodiments, according to any of the methods for modulating an immune response employing a modified T cell, the modified T cell comprises an antigen and an adjuvant. In some embodiments, the modified T cell comprises the antigen at a concentration between about 1 pM and about 10 mM. In some embodiments, the modified T cell comprises the adjuvant at a concentration between about 1 pM and about 10 mM. In some embodiments, the ratio of the antigen to the adjuvant in the modified T cell is between about 10000:1 and about 1:10000. In some embodiments, the modified T cell comprises a complex comprising: a) the antigen, b) the antigen and at least one other antigen, and/or c) the antigen and the adjuvant.

In certain aspects, there is provided a method for modulating an immune response in an individual, comprising: a) administering a modified T cell comprising an antigen comprising the amino acid sequence of any one of SEQ ID NOs: 18-25 to the individual; and b) administering an adjuvant to the individual. In some embodiments, the adjuvant is administered concurrently or simultaneously with the modified T cell. In some embodiments, the adjuvant and the modified T cell are administered sequentially. In some embodiments, the adjuvant is administered prior to administration of the modified T cell. In some embodiments, the adjuvant is administered following administration of the modified T cell. In some embodiments, the adjuvant is administered systemically, e.g., intravenously. In some embodiments, the adjuvant is administered locally, e.g., intratumorally. In some embodiments, the adjuvant is not contained in a cell, e.g., the adjuvant is free in solution. In some embodiments, the adjuvant is contained in a cell, such as a T cell. In some embodiments, the adjuvant is delivered into the T cell according to any of the methods of intracellular delivery described herein. In some embodiments, the modified T cell comprising the antigen is prepared by a process comprising the steps of c) passing a cell suspension comprising an input T cell through a cell-deforming constriction, wherein a diameter of the constriction is a function of a diameter of the input T cell in the suspension, thereby causing perturbations of the input T cell large enough for the antigen to pass through to form a perturbed input T cell; and d) incubating the perturbed input T cell with the antigen for a sufficient time to allow the antigen to enter the perturbed input T cell, thereby generating the modified T cell comprising the antigen In some embodiments, the concentration of the antigen incubated with the perturbed input T cell is between about 1 pM-10 mM. In some embodiments, the antigen is encapsulated in a nanoparticle. In some embodiments, the modified T cell further comprises an adjuvant. In some embodiments, the adjuvant contained in the modified T cell and the adjuvant of step b) are the same compound. In some embodiments, the adjuvant contained in the modified T cell and the adjuvant of step b) are different compounds.

In certain aspects, there is provided a method for modulating an immune response in an individual, comprising: a) passing a cell suspension comprising an input T cell through a cell-deforming constriction, wherein a diameter of the constriction is a function of a diameter of the input T cell in the suspension, thereby causing perturbations of the input T cell large enough for an antigen to pass through to form a perturbed input T cell, wherein the antigen comprises an immunogenic epitope; b) incubating the perturbed input T cell with the antigen for a sufficient time to allow the antigen to enter the perturbed input T cell, thereby generating a modified T cell comprising the antigen; c) administering the modified T cell to the individual; and d) administering an adjuvant to the individual. In some embodiments, the adjuvant is administered concurrently or simultaneously with the modified T cell. In some embodiments, the adjuvant and the modified T cell are administered sequentially. In some embodiments, the adjuvant is administered prior to administration of the modified T cell. In some embodiments, the adjuvant is administered following administration of the modified T cell. In some embodiments, the adjuvant is administered systemically, e.g., intravenously. In some embodiments, the adjuvant is administered locally, e.g., intratumorally. In some embodiments, the adjuvant is not contained in a cell, e.g., the adjuvant is free in solution. In some embodiments, the adjuvant is contained in a cell, such as a T cell. In some embodiments, the adjuvant is delivered into the T cell according to any of the methods of intracellular delivery described herein. In some embodiments, the concentration of the antigen incubated with the perturbed input T cell is between about 1 pM-10 mM. In some embodiments, the antigen is encapsulated in a nanoparticle.

In some embodiments, according to any of the methods for modulating an immune response in an individual described herein, the immune response is enhanced. In some embodiments, the enhanced immune response is directed towards the antigen.

In some embodiments, according to any of the methods for modulating an immune response in an individual described herein, the method employs a cell-deforming constriction through which an input T cell is passed. In some embodiments, the diameter of the constriction is less than the diameter of the input T cell. In some embodiments, the diameter of the constriction is about 20% to about 99% of the diameter of the input T cell. In some embodiments, the diameter of the constriction is about 20% to about 60% of the diameter of the input T cell. In some embodiments, the cell-deforming constriction is contained in a microfluidic channel, such as any of the microfluidic channels described herein. The microfluidic channel may be contained in any of the microfluidic devices described herein, such as described in the section titled Microfluidic Devices below. Thus, in some embodiments, according to any of the methods for modulating an immune response in an individual described herein employing a microfluidic channel including a cell-deforming constriction through which an input T cell is passed, the method comprises passing the input T cell through a microfluidic channel including a cell-deforming constriction contained in any of the microfluidic systems described herein. In some embodiments, a deforming force is applied to the input T cell as it passes through the constriction, thereby causing the perturbations of the input T cell.

In some embodiments, according to any of the methods for modulating an immune response in an individual described herein, the method employs a modified T cell comprising an antigen and an adjuvant. In some embodiments, the antigen and/or adjuvant are present in the cytosol and/or a vesicle of the modified T cell. In some embodiments, the vesicle is an endosome. In some embodiments, the antigen and/or the adjuvant are present in multiple compartments of the modified T cell. In some embodiments, the antigen or immunogenic epitope is bound to the surface of the modified T cell. In some embodiments, the modified T cell includes one or more of helper T cells, cytotoxic T cells, memory T cells, or natural killer T cells. In some embodiments, the modified T cell includes one or more of CD3+ T cells, CD4+ T cells, CD8+ T cells, CD45RA+ T cells, CD45RO+ T cells, or γδ-T cells.

In some embodiments, according to any of the methods for modulating an immune response in an individual described herein, the method employs a modified T cell comprising an adjuvant. In some embodiments, the adjuvant is a CpG oligodeoxynucleotide (ODN), IFN-α, STING agonists, RIG-I agonists, or poly I:C. In some embodiments, the adjuvant is a CpG ODN. In some embodiments, the adjuvant is a CpG ODN. In some embodiments, the CpG ODN is no greater than about 50 (such as no greater than about any of 45, 40, 35, 30, 25, 20, or fewer) nucleotides in length. In some embodiments, the CpG ODN is a Class A CpG ODN, a Class B CpG ODN, or a Class C CpG ODN. In some embodiments, the CpG ODN comprises the nucleotide sequence of any one of SEQ ID NOs: 26-37. In some embodiments, the CpG ODN comprises the nucleotide sequence of SEQ ID NO: 30. In some embodiments, the CpG ODN comprises the nucleotide sequence of SEQ ID NO: 31. In some embodiments, the modified T cell comprises a plurality of different CpG ODNs. For example, in some embodiments, the modified T cell comprises a plurality of different CpG ODNs selected from among Class A, Class B, and Class C CpG ODNs.

Exemplary adjuvants include, without limitation, stimulator of interferon genes (STING) agonists, retinoic acid-inducible gene I (RIG-I) agonists, and agonists for TLR3, TLR4, TLR7, TLR8 and/or TLR9. Exemplary adjuvants include, without limitation, CpG ODN, interferon-α (IFN-α), polyinosinic:polycytidylic acid (polyI:C), imiquimod (R837), resiquimod (R848), or lipopolysaccharide (LPS). In some embodiments, the adjuvant is CpG ODN, LPS, IFN-α, STING agonists, RIG-I agonists, poly I:C, R837, R848, a TLR3 agonist, a TLR4 agonist or a TLR 9 agonist. In particular embodiments, the adjuvant is a CpG ODN. In some embodiments, the adjuvant is a CpG ODN. In some embodiments, the CpG ODN is a Class A CpG ODN, a Class B CpG ODN, or a Class C CpG ODN. In some embodiments, the CpG ODN adjuvant comprise of a selection from the group of CpG ODN 1018, CpG ODN 1585, CpG ODN 2216, CpG ODN 2336, CpG ODN 1668, CpG ODN 1826, CPG ODN 2006, CpG ODN 2007, CpG ODN BW006, CpG ODN D-SL01, CpG ODN 2395, CpG ODN M362, CpG ODN D-SL03. In some embodiments, the CpG ODN adjuvant is CpG ODN 1826 (TCCATGACGTTCCTGACGTT; SEQ ID NO: 30) or CpG ODN 2006 (also known as CpG ODN 7909) (TCGTCGTTTTGTCGTTTTGTCGTT; SEQ ID NO:30) oligonucleotide. In some embodiments, the adjuvant is CpG ODN 7909. In some embodiments, the RIG-I agonist comprises polyinosinic:polycytidylic acid (polyI:C). Multiple adjuvants can also be used in conjunction with antigens to enhance the elicitation of immune response. In some embodiments, the modified PBMCs comprise more than one adjuvant. Multiple adjuvants can also be used in conjunction with antigens to enhance the elicitation of immune response. In some embodiments, the modified PBMCs comprise more than one adjuvant. In some embodiments, the modified PBMCs comprise any combination of the adjuvants CpG ODN, LPS, IFN-α, STING agonists, RIG-I agonists, poly I:C, R837, R848, a TLR3 agonist, a TLR4 agonist or a TLR 9 agonist.

In any of the embodiments described herein, unless otherwise indicated, the adjuvant may refer to (a) an adjuvant that is incubated with and passes through a perturbed input T cell, or (b) an adjuvant co-administered with modified T cells to an individual.

In some embodiments, according to any of the methods for modulating an immune response in an individual described herein, the method employs a modified T cell comprising an antigen comprising an immunogenic epitope. In some embodiments, the immunogenic epitope is derived from a disease-associated antigen. In some embodiments, the immunogenic epitope is derived from peptides or mRNA isolated from a diseased cell. In some embodiments, the immunogenic epitope is derived from a protein ectopically expressed or overexpressed in a disease cell. In some embodiments, the immunogenic epitope is derived from a neoantigen, e.g., a cancer-associated neoantigen. In some embodiments, the immunogenic epitope comprises a neoepitope, e.g., a cancer-associated neoepitope. In some embodiments, the immunogenic epitope is derived from a non-self antigen. In some embodiments, the immunogenic epitope is derived from a mutated or otherwise altered self antigen. In some embodiments, the immunogenic epitope is derived from a tumor antigen, viral antigen, bacterial antigen, or fungal antigen. In some embodiments, the antigen comprises a plurality of immunogenic epitopes. In some embodiments, some of the plurality of immunogenic epitopes are derived from the same source. For example, in some embodiments, some of the plurality of immunogenic epitopes are derived from the same viral antigen. In some embodiments, all of the plurality of immunogenic epitopes are derived from the same source. In some embodiments, none of the plurality of immunogenic epitopes are derived from the same source. In some embodiments, the modified T cell comprises a plurality of different antigens.

In some embodiments, according to any of the methods for modulating an immune response in an individual described herein employing a modified T cell comprising an antigen comprising an immunogenic epitope, the antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the immunogenic peptide epitope fused to the N-terminal flanking polypeptide and/or the C-terminal flanking polypeptide is a non-naturally occurring sequence. In some embodiments, the N-terminal and/or C-terminal flanking polypeptides are derived from an immunogenic synthetic long peptide (SLP). In some embodiments, the N-terminal and/or C-terminal flanking polypeptides are derived from a disease-associated immunogenic SLP. In some embodiments, the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17.

In some embodiments, according to any of the methods for modulating an immune response in an individual described herein employing a modified T cell comprising an antigen comprising an immunogenic epitope, the antigen or immunogenic epitope contained therein is derived from a human papillomavirus (HPV) antigen. In some embodiments, the antigen or immunogenic epitope contained therein is derived from any of HPV-16, 18, 26, 31, 33, 35, 39, 45, 51, 52, 53, 56, 58, 59, 66, 68, 73, and 82. In some embodiments, the antigen or immunogenic epitope contained therein is derived from an HPV-16 antigen or an HPV-18 antigen. In further embodiments, the antigen or immunogenic epitope contained therein is derived from an HPV E6 antigen (e.g., an HPV-16 or HPV-18 E6 antigen) or an HPV E7 antigen (e.g., an HPV-16 or HPV-18 E7 antigen). In some embodiments, the antigen comprises an HLA-A2-restricted peptide derived from HPV E6 and/or E7. In some embodiments, the antigen comprises a fragment of an HPV-16 E6 protein between residues 29 and 38 (i.e., HPV-16 $E6_{29-38}$). In some embodiments, the antigen comprises a fragment of an HPV-16 E6 protein between residues 48 and 57 (i.e., HPV-16 $E6_{48-57}$). In some embodiments, the antigen comprises a fragment of an HPV-16 E7 protein between residues 11 and 20 (i.e., HPV-16 $E7_{11-20}$). In some embodiments, the antigen comprises a fragment of an HPV-16 E7 protein between residues 49 and 57 (i.e., HPV-16 $E7_{49-57}$). In some embodiments, the antigen comprises the amino acid sequence of any one of SEQ ID NOs: 1-4. In some embodiments, the antigen comprises the amino acid sequence of any one of SEQ ID NOs: 1-4 flanked with an N-terminal polypeptide comprising the amino acid sequence of any one of SEQ ID NOs: 5-10 and a C-terminal polypeptide comprising the amino acid sequence of any one of SEQ ID NOs: 11-17. In some embodiments, the antigen comprises the amino acid sequence of any one of SEQ ID NOs: 18-25.

In some embodiments, according to any of the methods for modulating an immune response in an individual described herein employing a modified T cell comprising an antigen comprising an immunogenic epitope, the antigen or immunogenic epitope contained therein is derived from a human cytomegalovirus (HCMV) antigen. In some embodiments, the HCMV is strain AD169 or strain Merlin HCMV. In some embodiments, the antigen comprises an HLA-A2-restricted peptide derived from HCMV pUL83. In some embodiments, the modified T cell comprises a plurality of antigens that comprise a plurality of immunogenic epitopes. In some embodiments, following administration to an individual of the modified T cell comprising the plurality of antigens that comprise the plurality of immunogenic epitopes, none of the plurality of immunogenic epitopes decreases an immune response in the individual to any of the other immunogenic epitopes. In some embodiments, the antigen is a polypeptide and the immunogenic epitope is an immunogenic peptide epitope. In some embodiments, the immunogenic peptide epitope is fused to an N-terminal flanking polypeptide and/or a C-terminal flanking polypeptide. In some embodiments, the antigen is a polypeptide comprising an immunogenic peptide epitope and one or more heterologous peptide sequences. In some embodiments, the antigen is a polypeptide comprising an immunogenic peptide epitope that is flanked on the N-terminus and/or the C-terminus by heterologous peptide sequences. In some embodiments, the flanking heterologous peptide sequences are derived from disease-associated immunogenic peptides.

In some embodiments, according to any of the methods for modulating an immune response in an individual described herein employing a modified T cell comprising an antigen comprising an immunogenic epitope, the antigen is capable of being processed into an MHC class I-restricted peptide and/or an MHC class II-restricted peptide. In some embodiments, the antigen is capable of being processed into an MHC class I-restricted peptide. In some embodiments, the antigen is capable of being processed into an MHC class II-restricted peptide. In some embodiments, the antigen comprises a plurality of immunogenic epitopes, and is capable of being processed into an MHC class I-restricted peptide and an MHC class II-restricted peptide. In some embodiments, some of the plurality of immunogenic epitopes are derived from the same source. In some embodiments, all of the plurality of immunogenic epitopes are derived from the same source. In some embodiments, none of the plurality of immunogenic epitopes are derived from the same source.

In some embodiments, according to any of the methods for modulating an immune response in an individual described herein employing a modified T cell, the modified T cell comprises a plurality of antigens that comprise a plurality of immunogenic epitopes. In some embodiments, none of the plurality of immunogenic epitopes decreases an immune response in the individual to any of the other immunogenic epitopes.

In some embodiments, according to any of the methods for modulating an immune response in an individual described herein employing a modified T cell, the modified T cell comprises an antigen and an adjuvant. In some embodiments, the modified T cell comprises the adjuvant at a concentration between about 1 pM and about 10 mM. For example, in some embodiments, the concentration of adjuvant in the modified T cell is any of less than about 1 pM, about 10 pM, about 100 pM, about 1 nM, about 10 nM, about 100 nM, about 1 μM, about 10 μM, about 100 μM, about 1 mM or about 10 mM. In some embodiments, the concentration of adjuvant in the modified T cell is greater than about 10 mM. In some embodiments, the concentration of the antigen in the modified T cell is any of between about 1 pM and about 10 pM, between about 10 pM and about 100 pM, between about 100 pM and about 1 nM, between about 1 nM and about 10 nM, between about 10 nM and about 100 nM, between about 100 nM and about 1 μM, between about 1 μM and about 10 μM, between about 10 μM and about 100 μM, between about 100 μM and about 1 mM, or between 1 mM and about 10 mM. In some embodiments, the molar ratio of antigen to adjuvant in the modified T cell is any of between about 10000:1 to about 1:10000. For example, in some embodiments, the molar ratio of the antigen to adjuvant in the modified T cell is about any of 10000:1, about 1000:1, about 100:1, about 10:1, about 1:1, about 1:10, about 1:100, about 1:1000, or about 1:10000. In some embodiments, the molar ratio of the antigen to adjuvant in the modified T cell is any of between about 10000:1 and about 1000:1, between about 1000:1 and about 100:1, between about 100:1 and about 10:1, between about 10:1 and about 1:1, between about 1:1 and about 1:10, between about 1:10 and about 1:100, between about 1:100 and about 1:1000, between about 1:1000 and about 1:10000. In some embodiments, the modified T cell comprises a complex comprising: a) the antigen, b) the antigen and at least one other antigen, and/or c) the antigen and the adjuvant.

In some embodiments, according to any of the methods for modulating an immune response in an individual described herein employing a modified T cell, the modified T cell further comprises an agent that enhances the viability and/or function of the modified T cell as compared to a corresponding modified T cell that does not comprise the agent. In some embodiments, the agent is a stabilizing agent or a co-factor. In some embodiments, the agent is albumin. In some embodiments, the albumin is mouse, bovine, or human albumin. In some embodiments, the agent is a divalent metal cation, glucose, ATP, potassium, glycerol, trehalose, D-sucrose, PEG1500, L-arginine, L-glutamine, or EDTA.

In some embodiments, according to any of the methods for modulating an immune response in an individual described herein employing a modified T cell, the modified T cell comprises a further modification. In some embodiments, the modified T cell comprises a further modification to modulate MHC class I expression. In some embodiments, the modified T cell comprises a further modification to decrease MHC class I expression. In some embodiments, the modified T cell comprises a further modification to increase MHC class I expression. In some embodiments, the modified T cell comprises a further modification to modulate MHC class II expression. In some embodiments, the modified T cell comprises a further modification to decrease MHC class II expression. In some embodiments, the modified T cell comprises a further modification to increase MHC class II expression. In some embodiments, an innate immune response mounted in an individual in response to administration, in an allogeneic context, of the modified T cells is reduced compared to an innate immune response mounted in an individual in response to administration, in an allogeneic context, of corresponding modified T cells that do not comprise the further modification. In some embodiments, the circulating half-life of the modified T cells in an individual to which they were administered is increased compared to the circulating half-life of corresponding modified T cells that do not comprise the further modification in an individual to which they were administered.

In some embodiments, according to any of the methods for modulating an immune response in an individual employing a modified T cell described herein, the method comprises administering the modified T cell to the individual. In some embodiments, the modified T cell is allogeneic to the individual. In some embodiments, the modified T cell is autologous to the individual. In some embodiments, the individual is pre-conditioned to modulate inflammation and/or an immune response. In some embodiments, the individual is pre-conditioned to decrease inflammation and/or an immune response. In some embodiments, the individual is pre-conditioned to increase inflammation and/or an immune response. In some embodiments, administration of the modified T cell to the individual results in activation and/or expansion of cytotoxic T lymphocytes (CTLs) specific for the antigen. In some embodiments, administration of the modified T cell to the individual results in activation and/or expansion of helper T (Th) cells specific for the antigen. In some embodiments, the amount of the modified T cell administered to the individual is between about $1\times10^6$ and about $1\times10^2$ cells. In some embodiments, the amount of the modified T cell administered to the individual is less than about any of $1\times10^6$, $1\times10^7$, $1\times10^8$, $1\times10^9$, $1\times10^{10}$, $1\times10^{11}$ and about $1\times10^{12}$ cells. In some embodiments, the amount of the modified T cell administered to the individual is between about any of $1\times10^6$ and $1\times10^7$, $1\times10^7$ and $1\times10^8$, $1\times10^8$ and $1\times10^9$, $1\times10^9$ and $1\times10^{10}$, $1\times10^{10}$ and $1\times10^{11}$ and $1\times10^{11}$ and $1\times10^{12}$ cells. In some embodiments, the method comprises multiple administrations of the modified T cell. In some embodiments, the method comprises any of about 2, 3, 4, 5, 6, 7, 8, 9, 10, or more than about 10 administrations. In some embodiments, the time interval between two successive administrations of the modified T cell is between about 1 day and about 1 month. In some embodiments, the administration is daily, every 2 days, every 3 days, every 4 days, every 5 days, every 6 days, weekly, biweekly, or monthly. In some embodiments, successive administrations are given for up to one year or more.

In some embodiments, according to any of the methods for modulating an immune response in an individual employing a modified T cell described herein, the method further comprises administering to the individual a second adjuvant. In some embodiments, the second adjuvant is administered systemically, e.g., intravenously. In some embodiments, the second adjuvant is administered locally, e.g., intratumorally. In some embodiments, the second adjuvant is not contained in a cell, e.g., the second adjuvant is free in solution. In some embodiments, the second adjuvant is IFN-α or a CpG ODN. In some embodiments, the adjuvant contained in the modified T cell and the second adjuvant are the same compound. For example, in the embodiments, the modified T cell comprises a CpG ODN, and the second adjuvant is also the CpG ODN. In some embodiments, the adjuvant contained in the modified T cell and the second adjuvant are different compounds. For example, in some embodiments, the modified T cell comprises a CpG ODN, and the second adjuvant is IFN-α. In some embodiments, the modified T cell and the second adjuvant are administered concurrently or simultaneously. In some embodiments, the modified T cell and the second adjuvant are administered sequentially. In some embodiments, the modified T cell is administered prior to administering the second adjuvant. In some embodiments, the modified T cell is administered following administration of the second adjuvant.

In some embodiments, according to any of the methods for modulating an immune response in an individual employing a modified T cell described herein, the method further comprises administering an immune checkpoint inhibitor to the individual. In some embodiments, the modified T cell and the immune checkpoint inhibitor are administered to the individual concurrently. In some embodiments, the modified T cell and the immune checkpoint inhibitor are administered to the individual simultaneously. In some embodiments, the modified T cell and the immune checkpoint inhibitor are administered to the individual sequentially. In some embodiments, the modified T cell is administered to the individual following administration of the immune checkpoint inhibitor to the individual. In some embodiments, the modified T cell is administered to the individual prior to administration of the immune checkpoint inhibitor to the individual. In some embodiments, the immune checkpoint inhibitor is targeted to any one of PD-1, PD-L1, CTLA-4, and TIM-3. Exemplary immune checkpoint inhibitor is targeted to, without limitation, PD-1, PD-L1, CTLA-4, LAG3 or TIM-3. In some embodiments, the immune checkpoint inhibitor is targeted to one or more of PD-1, PD-L1, CTLA-4, LAG3 or TIM-3. In some embodiments, the immune checkpoint inhibitor is one or more of: an antibody that binds to PD-1, an antibody that binds PD-L1, an antibody that binds CTLA-4, an antibody that binds LAG3, or an antibody that binds TIM-3. In further embodiments, the antibody can be a full length antibody or any variants, for example but not limited to, an antibody fragment, a single chain variable fragment (ScFv), or a fragment antigen-binding (Fab). In further embodiments, the antibody can be bispecific, trispecific or multispecific. In some embodiments, the immune checkpoint inhibitor is one or more chemical compounds that binds to and/or inhibits one or more of PD-1, PD-L1, CTLA-4, LAG3 or TIM-3. In some embodiments, the immune checkpoint inhibitor is one or more peptides that binds to and/or inhibits one or more of PD-1, PD-L1, CTLA-4, LAG3 or TIM-3.

Other exemplary immune checkpoint inhibitor is targeted to, without limitation, TIGIT, VISTA, TIM1, B7-H4 (VTCN1) or BTLA. In some embodiments, the immune checkpoint inhibitor is targeted to one or more of TIGIT, VISTA, TIM1, B7-H4 (VTCN1) or BTLA. In some embodiments, the immune checkpoint inhibitor is one or more of: an antibody that binds to TIGIT, an antibody that binds VISTA, an antibody that binds TIM1, an antibody that binds B7-H4 (VTCN1) or an antibody that binds BTLA. In further embodiments, the antibody can be a full length antibody or any variants, for example but not limited to, an antibody fragment, a single chain variable fragment (ScFv), or a fragment antigen-binding (Fab). In further embodiments, the antibody can be bispecific, trispecific or multispecific. In some embodiments, the immune checkpoint inhibitor is one or more chemical compounds that binds to and/or inhibits one or more of PD-1, PD-L1, CTLA-4, LAG3, TIM-3, TIGIT, VISTA, TIM1, B7-H4 (VTCN1) or BTLA. In some embodiments, the immune checkpoint inhibitor is one or more peptides that binds to and/or inhibits one or more of PD-1, PD-L1, CTLA-4, LAG3, TIM-3, TIGIT, VISTA, TIM1, B7-H4 (VTCN1) or BTLA.

Chemotherapy can be used in combination with any one of the modified T cells described herein to achieve additive or synergistic effects against cancers, for example, HPV-associated cancers. In some embodiments, the composition comprising the modified T cells is administered in combination with administration of a chemotherapy. In some embodiments, the composition comprising the modified T cells and the chemotherapy are administered simultaneously. In some embodiments, the composition comprising the modified T cells and the chemotherapy are administered sequentially. In some embodiments, the composition comprising the modified T cells is administered in combination with administration of a chemotherapy and in combination with an immune checkpoint inhibitor.

In some embodiments, the composition comprising the modified T cells is administered prior to administration of the chemotherapy. In some embodiments, the composition comprising the modified T cells is administered following administration of the chemotherapy. For example, the composition comprising the modified T cells is administered from about 1 hour to about 1 week prior to administration of the chemotherapy. For example, in some embodiments, the composition comprising the modified T cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the chemotherapy. In some embodiments, the composition comprising the modified T cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the chemotherapy.

In some embodiments, the composition comprising the modified T cells is administered following administration of the chemotherapy. For example, the composition comprising the modified T cells is administered from about 1 hour to about 1 week following administration of the chemotherapy. For example, in some embodiments, the composition comprising the modified T cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the chemotherapy. In some embodiments, the composition comprising the modified T cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the chemotherapy.

In some embodiments, the method comprises multiple administration of the composition comprising the modified T cells and/or multiple administration of the chemotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the modified T cells and/or the chemotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the modified T cells and/or the chemotherapy.

Exemplary chemotherapy can be cell cycle dependent or cell cycle independent. In some embodiments, the chemotherapy comprises one or more chemotherapeutic agents. In some embodiments, a chemotherapeutic agent can target one or more of cell division, DNA, or metabolism in cancer. In some embodiments, the chemotherapeutic agent is a platinum-based agent, such as but not limited to cisplatin, oxaliplatin or carboplatin. In some embodiments, the chemotherapeutic agent is a taxane (such as docetaxel or paclitaxel). In some embodiments, the chemotherapeutic agent is 5-fluorouracil, doxorubicin, or irinotecan. In some embodiments, the chemotherapeutic agent is one or more of: an alkylating agent, an antimetabolite, an antitumor antibiotic, a topoisomerase inhibitor or a mitotic inhibitor. In some embodiments, the chemotherapy comprises cisplatin.

Radiotherapy can be used in combination with any one of the modified T cells described herein to achieve additive or synergistic effects against cancers, for example, HPV-associated cancers. In some embodiments, the composition comprising the modified T cells is administered in combination with administration of a radiotherapy. In some embodiments, the composition comprising the modified T cells and the radiotherapy are administered simultaneously. In some embodiments, the composition comprising the modified T cells and the radiotherapy are administered sequentially. In some embodiments, the composition comprising the modified T cells is administered in combination with administration of a radiotherapy, in combination with a chemotherapy, and/or in combination with an immune checkpoint inhibitor.

In some embodiments, the composition comprising the modified T cells is administered prior to administration of the radiotherapy. In some embodiments, the composition comprising the modified T cells is administered following administration of the radiotherapy. For example, the composition comprising the modified T cells is administered from about 1 hour to about 1 week prior to administration of the radiotherapy. For example, in some embodiments, the composition comprising the modified T cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days prior to administration of the radiotherapy. In some embodiments, the composition comprising the modified T cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days prior to administration of the radiotherapy.

In some embodiments, the composition comprising the modified T cells is administered following administration of the radiotherapy. For example, the composition comprising the modified T cells is administered from about 1 hour to about 1 week following administration of the radiotherapy. For example, in some embodiments, the composition comprising the modified T cells is administered about 1 hour, about 2 hours, about 3 hours, about 4 hours, about 6 hours, about 8 hours, about 10 hours, about 12 hours, about 14 hours, about 16 hours, about 18 hours, about 20 hours, about 24 hours, about 30 hours, about 36 hours, about 42 hours, about 48 hours, about 60 hours, about 3 days, about 4 days, about 5 days, about 6 days, or about 7 days following administration of the radiotherapy. In some embodiments, the composition comprising the modified T cells is administered from between about 1 hour and about 2 hours, from between about 2 hours and about 3 hours, from between about 3 hours and about 4 hours, from between about 4 hours and about 6 hours, from between about 6 hours and about 8 hours, from between about 8 hours and about 10 hours, from between about 10 hours and about 12 hours, from between about 12 hours and about 14 hours, from between about 14 hours and about 16 hours, from between about 16 hours and about 18 hours, from between about 18 hours and about 20 hours, from between about 20 hours and about 24 hours, from between about 24 hours and about 30 hours, from between about 30 hours and about 36 hours, from between about 36 hours and about 42 hours, from between about 42 hours and about 48 hours, from between about 48 hours and about 60 hours, from between about 60 hours and about 3 days, from between about 3 days and about 4 days, from between about 4 days and about 5 days, from between about 5 days and about 6 days, from between about 6 days and about 7 days following administration of the radiotherapy.

In some embodiments, the method comprises multiple administration of the composition comprising the modified T cells and/or multiple administration of the radiotherapy. For example, in some embodiments, the method comprises two administrations, three administrations, four administrations, five administrations, six administrations, seven administrations, eight administrations, nine administrations, ten administrations, eleven administrations, twelve administrations, thirteen administrations, fourteen administrations, or fifteen administrations of the composition comprising the modified T cells and/or the radiotherapy. For example, in some embodiments, the method comprises less than five administrations, less than ten administrations, less than fifteen administrations, less than twenty administrations, less than twenty-five administrations, less than thirty administrations, less than fifty administrations, less than seventy-five administrations, less than one hundred, or less than two hundred administrations of the composition comprising the modified T cells and/or the radiotherapy.

In certain aspects, there is provided a method for modulating an immune response in an individual, comprising: administering to the individual a modified T cell associated with an antigen, wherein the modified T cell is prepared by a process comprising the steps of a) incubating an input T cell with i) an antigen, or ii) and antigen and an adjuvant, for a sufficient time to allow the antigen to associate with the cell surface of the input T cell, wherein the antigen comprises an immunogenic epitope, thereby generating a modified T cell associated with the antigen; and b) administering the modified T cell to the individual.

In certain aspects, there is provided a modified T cell for use in a method of medical treatment, said method comprising: a) passing a cell suspension comprising an input T cell comprising an antigen through a cell-deforming constriction, wherein the antigen comprises an immunogenic epitope, wherein a diameter of the constriction is a function of a diameter of the input T cell in the suspension, thereby causing perturbations of the input T cell large enough for an adjuvant to pass through to form a perturbed input T cell; b) incubating the perturbed input T cell with the adjuvant for a sufficient time to allow the adjuvant to enter the perturbed input T cell, thereby generating a modified T cell comprising the antigen and the adjuvant; and c) administering the modified T cell to the individual. In some embodiments, the concentration of the adjuvant incubated with the perturbed input T cell is between about 1 pM-10 mM. In some embodiments, the adjuvant is encapsulated in a nanoparticle.

In certain aspects, there is provided a modified T cell for use in treating cancer, an infectious disease or a viral-related disease in an individual, said method comprising: a) passing a cell suspension comprising an input T cell comprising an antigen through a cell-deforming constriction, wherein the antigen comprises an immunogenic epitope, wherein a diameter of the constriction is a function of a diameter of the input T cell in the suspension, thereby causing perturbations of the input T cell large enough for an adjuvant to pass through to form a perturbed input T cell; b) incubating the perturbed input T cell with the adjuvant for a sufficient time to allow the adjuvant to enter the perturbed input T cell, thereby generating a modified T cell comprising the antigen and the adjuvant; and c) administering the modified T cell to the individual. In some embodiments, the antigen is associated with a cancer, an infectious disease or a viral related disease. In some embodiments, the concentration of the adjuvant incubated with the perturbed input T cell is between about 1 pM-10 mM. In some embodiments, the adjuvant is encapsulated in a nanoparticle.

In some embodiments, the modified T cells of the invention do not induce tolerance in an individual. In some embodiments, the modified T cells do not suppress an immune response in an individual. In some embodiments, the modified T cells do not comprise a tolerogenic factor. In some embodiments, the modified T cells are not administered in combination with a tolerogenic factor. In some embodiments, the modified T cells are not administered before, simultaneous with, or after administration of a tolerogenic factor.

Antigens

In some embodiments the invention employs delivery of antigens to modulate an immune response, wherein the antigen is delivered to a T cell by any of the methods described herein. In some embodiments, the antigen is a single antigen. In some embodiments, the antigen is a mixture of antigens. An antigen is a substance that stimulates a specific immune response, such as a cell or antibody-mediated immune response. Antigens bind to receptors expressed by immune cells, such as T cell receptors (TCRs), which are specific to a particular antigen. Antigen-receptor binding subsequently triggers intracellular signaling pathways that lead to downstream immune effector pathways, such as cell activation, cytokine production, cell migration, cytotoxic factor secretion, and antibody production.

In some embodiments, the antigen is a polypeptide antigen. In some embodiments, the antigen is a disease-associated antigen. In some embodiments, antigens are derived from foreign sources, such as bacteria, fungi, viruses, or allergens. In some embodiments, antigens are derived from internal sources, such as self-proteins (i.e. self-antigens) or a portion of a self-protein. In some embodiments, the antigen is a mutated or otherwise altered self-antigen. In some embodiments, the antigen is a tumor antigen. In some embodiments, the antigen is in a cell lysate. Self-antigens are antigens present on or in an organism's own cells. Self-antigens do not normally stimulate an immune response, but may in the context of autoimmune diseases, such as Type I Diabetes or Rheumatoid Arthritis, or when overexpressed or expressed aberrantly/ectopically.

In some embodiments, the antigen is associated with a virus. In some embodiments, the antigen is a viral antigen. Exemplary viral antigens include HPV antigens, HCMV antigens, SARS-CoV antigens, and influenza antigens.

In some embodiments, the antigen is associated with a microorganism; for example, a bacterium. In some embodiments, the modulated immune response comprises an increased pathogenic immune response to the microorganism; for example, a bacterium.

In certain aspects, the invention employs methods for delivering an antigen into a T cell, the method comprising passing a cell suspension comprising the T cell through a constriction, wherein said constriction deforms the T cell, thereby causing a perturbation of the cell such that the antigen enters the cell, wherein said cell suspension is contacted with the antigen. In some embodiments, the antigen is delivered to the T cell in vitro, ex vivo, or in vivo.

In some embodiments, the antigen to deliver is purified. In some embodiments, the antigen is at least about 60% by weight (dry weight) the antigen of interest. In some embodiments, the purified antigen is at least about 75%, 90%, or 99% the antigen of interest. In some embodiments, the purified antigen is at least about 90%, 91%, 92%, 93%, 94%, 95%, 98%, 99%, or 100% (w/w) the antigen of interest. Purity is determined by any known methods, including, without limitation, column chromatography, thin layer chromatography (TLC), high-performance liquid chromatography (HPLC), nuclear magnetic resonance (NMR) spectroscopy, mass spectrometry, or SDS-PAGE gel electrophoresis. Purified DNA or RNA is defined as DNA or RNA that is free of exogenous nucleic acids, carbohydrates, and lipids.

Adjuvants

Adjuvants can be used to boost an immune cell response (e.g. T cell response), such as an immune response to an antigen. Multiple adjuvants can also be used to enhance an immune response, and can be used in conjunction with antigens, for example to enhance an immune response to the antigens as compared to an immune response to the antigens alone. In some embodiments, the invention employs delivery of adjuvants to enhance an immune response, wherein the adjuvant is delivered to a T cell by any of the methods described herein. In some embodiments, the adjuvant enhances an immune response to an antigen. For example, the adjuvant may promote immunogenic presentation of the antigen by an antigen-presenting cell. In some embodiments, the adjuvant is introduced simultaneously with the antigen. In some embodiments, the adjuvant and antigen are introduced sequentially. In some embodiments, the adjuvant is introduced prior to introduction of the antigen. In some embodiments, the adjuvant is introduced following introduction of the antigen. In some embodiments, the adjuvant alters T cell homing (e.g., T cell homing to a target tissue, such as a tumor) as compared to T cell homing in the absence of the adjuvant. In some embodiments, the adjuvant increases T cell proliferation as compared to T cell proliferation in the absence of the adjuvant.

In certain aspects, the invention employs methods for generating an immunogenic antigen-presenting T cell comprising an antigen from an input T cell, wherein the input T cell is passed through a constriction, wherein said constriction deforms the input T cell thereby causing a perturbation of the cell such that an antigen enters the input T cell, thereby generating the immunogenic antigen-presenting T cell comprising the antigen.

In certain aspects, the invention employs methods for delivering an adjuvant into a T cell, the method comprising passing a cell suspension comprising the T cell through a constriction, wherein said constriction deforms the T cell, thereby causing a perturbation of the T cell such that the adjuvant enters the cell, wherein said cell suspension is contacted with the adjuvant. In some embodiments, the adjuvant is delivered into the T cell in vitro, ex vivo, or in vivo.

Microfluidic Systems and Components Thereof

Microfluidic Channels to Provide Cell-Deforming Constrictions

In some embodiments, the invention provides methods for modulating an immune response by passing a cell suspension comprising a T cell through a constriction, wherein the constriction deforms the T cell thereby causing a perturbation of the T cell such that an antigen and/or adjuvant enters the T cell, wherein the constriction is contained within a microfluidic channel. In some embodiments, multiple constrictions can be placed in parallel and/or in series within the microfluidic channel. Exemplary microfluidic channels containing cell-deforming constrictions for use in the methods disclosed herein are described in WO2013059343. Exemplary surfaces having pores for use in the methods disclosed herein are described in WO2017041050.

In some embodiments, the microfluidic channel includes a lumen and is configured such that a T cell suspended in a buffer can pass through, wherein the microfluidic channel includes a constriction. The microfluidic channel can be made of any one of a number of materials, including silicon, metal (e.g., stainless steel), plastic (e.g., polystyrene), ceramics, glass, crystalline substrates, amorphous substrates, or polymers (e.g., Poly-methyl methacrylate (PMMA), PDMS, Cyclic Olefin Copolymer (COC), etc.). Fabrication of the microfluidic channel can be performed by any method known in the art, including dry etching, wet etching, photolithography, injection molding, laser ablation, or SU-8 masks.

In some embodiments, the constriction within the microfluidic channel includes an entrance portion, a centerpoint, and an exit portion. In some embodiments, the length, depth, and width of the constriction within the microfluidic channel can vary. In some embodiments, the diameter of the constriction within the microfluidic channel is a function of the diameter of the T cell. In some embodiments, the diameter of the constriction within the microfluidic channel is about 20%, to about 99% of the diameter of the T cell. In some embodiments, the constriction size is about 20%, about 30%, about 40%, about 50%, about 60%, about 70%, about 80%, about 90%, or about 99% of the T cell diameter. In some embodiments, the constriction size is about 20%, about 30%, about 40%, about 50%, about 60%, about 70%, about 80%, about 90%, or about 99% of the minimum cross-sectional distance of the T cell. In some embodiments, the channel comprises a constriction width of between about 2 μm and about 10 μm or any width or range of widths therebetween. For example, the constriction width can be any one of about 2 μm, about 3 μm, about 4 μm, about 5 μm, about 6 μm, or about 7 μm. In some embodiments, the channel comprises a constriction length of about 10 μm and a constriction width of about 4 μm. The cross-section of the channel, the entrance portion, the centerpoint, and the exit portion can also vary. For example, the cross-sections can be circular, elliptical, an elongated slit, square, hexagonal, or triangular in shape. The entrance portion defines a constriction angle, wherein the constriction angle is optimized to reduce clogging of the channel and optimized for enhanced delivery of a compound into the T cell. The angle of the exit portion can vary as well. For example, the angle of the exit portion is configured to reduce the likelihood of turbulence that can result in non-laminar flow. In some embodiments, the walls of the entrance portion and/or the exit portion are linear. In other embodiments, the walls of the entrance portion and/or the exit portion are curved.

In some embodiments according to any one of the methods or compositions described herein, the diameter of the constriction is a function of the T cell diameter. In some embodiments, the diameter of a T cell is measured by the minimum cross-sectional distance of the T cell.

In some embodiments according to any one of the methods or compositions described herein, the diameter of the constriction is about 10% to about 99% of the mean diameter of the input T cells. In some embodiments, the diameter of the constriction is any one of about 10% to about 90%, about 10% to about 80%, about 10% to about 70%, about 20% to about 60%, about 40% to about 60%, or about 30% to about 45% of the mean diameter of the input T cells. In some embodiments, the diameter of the constriction is any one of about 10% to about 20%, about 20% to about 30%, about 30% to about 40%, about 40% to about 50%, about 50% to about 60%, about 60% to about 70%, about 70% to about 80%, about 80% to about 90%, or about 90% to about 99% of the mean diameter of the input T cells. In some embodiments, the diameter of the constriction is any one of about 10%, 15%, 20%, 25%, 30%, 35%, 40%, 45%, 50%, 55%, 60%, 65%, 70%, 75%, 80%, 85%, 90%, 95%, or 99% of the mean diameter of the input T cells.

In some embodiments according to any one of the methods or compositions described herein, the diameter of the constriction is about 1.5 μm to about 10 μm. In some embodiments, the diameter of the constriction is about 2 μm to about 8 μm. In some embodiments, the diameter of the constriction is about 2.5 μm to about 6 μm. In some embodiments, the diameter of the constriction is about 3 μm to about 5 μm. In some embodiments, the diameter of the constriction is about 3 μm to about 4 μm. In some embodiments, the diameter of the constriction is any one of about 1.5 μm to about 10 μm, about 1.75 μm to about 9 μm, about 2 μm to about 8 μm, about 2.25 μm to about 7 μm, about 2.5 μm to about 6 μm, about 2.75 μm to about 5.5 μm, about 3 μm to about 5 μm, about 3 μm to about 4 μm, about 3.1 μm to about 3.9 μm, about 3.2 μm to about 3.8 μm, about 3.3 μm to about 3.7 μm, or about 3.4 μm to about 3.6 μm. In some embodiments, the diameter of the constriction is any one of about 1.0 μm, 1.2 μm, 1.4 μm, 1.6 μm, 1.8 μm, 2.0 μm, 2.2 μm, 2.4 μm, 2.6 μm, 2.8 μm, 3.0 μm, 3.2 μm, 3.4 μm, 3.6 μm, 3.8 μm, 4.0 μm, 4.2 μm, 4.4 μm, 4.6 μm, 4.8 μm, 5.0 μm, 5.5 μm, 6.0 μm, 6.5 μm, 7.0 μm, 8.0 μm, 9.0 μm or about 10.0 μm. In some embodiments, the diameter of the constriction is about 3.5 μm.

In some embodiments according to any one of the methods or compositions described herein, the diameter of the constriction is about 3 μm to about 15 μm. In some embodiments, the diameter of the constriction is about 3 μm to about 10 μm. In some embodiments, the diameter of the constriction is about 4 μm to about 10 μm. In some embodiments, the diameter of the constriction is about 4.2 μm to about 6 μm. In some embodiments, the diameter of the constriction is about 4.2 μm to about 4.8 μm. In some embodiments, the diameter of the constriction is any one of about 2 μm to about 14 μm, about 4 μm to about 12 μm, about 6 μm to about 9 μm, about 4 μm to about 6 μm, about 4 μm to about 5 μm, about 3.5 μm to about 7 μm, about 3.5 μm to about 6.3 μm, about 3.5 μm to about 5.6 μm, about 3.5 μm to about 4.9 μm, about 4.2 μm to about 6.3 μm, about 4.2 μm to about 5.6 μm, or about 4.2 μm to about 4.9 μm. In some embodiments, the diameter of the constriction is any one of about 2 μm, 2.5 μm, 3 μm, 3.5 μm, 4 μm, 4.5 μm, 5 μm, 5.5 μm, 6 μm, 6.5 μm, 7 μm, 7.5 μm, 8 μm, 8.5 μm, 9 μm, 9.5 μm, 10 μm, 10.5 μm, 11 μm, 11.5 μm, 12 μm, 12.5 μm, 13 μm, 13.5 μm, 14 μm, 14.5 μm or 15 μm. In some embodiments, the diameter of the constriction is any one of about 4.0 μm, 4.1 μm, 4.2 μm, 4.3 μm, 4.4 μm, 4.5 μm, 4.6 μm, 4.7 μm, 4.8 μm, 4.9 μm, or 5.0 μm In some embodiments, the diameter of the constriction is about 4.5 μm.

In some embodiments according to any one of the methods or compositions described herein, the input T cell is passed through the constriction at a flow rate between about 0.001 mL/min to about 200 mL/min or any rate or range of rates therebetween. In some embodiments, the flow rate is between about 0.001 mL/min to about 175 mL/min, about 0.001 mL/min to about 150 mL/min, about 0.001 mL/min to about 125 mL/min, about 0.001 mL/min to about 100 mL/min, about 0.001 mL/min to about 50 mL/min, about 0.001 mL/min to about 25 mL/min, about 0.001 mL/min to about 10 mL/min, about 0.001 mL/min to about 7.5 mL/min, about 0.001 mL/min to about 5.0 mL/min, about 0.001 mL/min to about 2.5 mL/min, about 0.001 mL/min to about 1 mL/min, about 0.001 mL/min to about 0.1 mL/min or about 0.001 mL/min to about 0.01 mL/min. In some embodiments, the flow rate is between about 0.001 mL/min to about 200 mL/min, about 0.01 mL/min to about 200 mL/min, about 0.1 mL/min to about 200 mL/min, about 1 mL/min to about 200 mL/min, about 10 mL/min to about 200 mL/min, about 50 mL/min to about 200 mL/min, about 75 mL/min to about 200 mL/min, about 100 mL/min to about 200 mL/min, about 150 mL/min to about 200 mL/min, about 0.5 mL/min to about 200 mL/min, about 1 mL/min to about 200 mL/min, about 2.5 mL/min to about 200 mL/min, about 5 mL/min to about 200 mL/min, about 7.5 mL/min to about 200 mL/min, about 10 mL/min to about 200 mL/min, about 25 mL/min to about 200 mL/min, or about 175 mL/min to about 200 mL/min. In some embodiments, the input T cell is passed through the constriction at a flow rate between about 10 mL/min to about 200 mL/min. In some embodiments, the input T cell is passed through the constriction at a flow rate of about 100 mL/min.

In some embodiments according to any one of the methods or compositions described herein, the constriction can have any shape known in the art; e.g. a 3-dimensional shape or a 2-dimensional shape. The 2-dimensional shape, such as the cross-sectional shape, of the constriction can be, without limitation, circular, elliptical, round, square, star-shaped, triangular, polygonal, pentagonal, hexagonal, heptagonal, or octagonal. The 3-dimensional shape of the constriction can be, without limitation, cylindrical, conical, or cuboidal. In some embodiments, the cross-sectional shape of the constriction is a rectangle. In some embodiments, the cross-sectional shape of the constriction is a slit. In some embodiments, the cross-sectional shape of the constriction is a slit comprising a width of about 2.5 μm to about 10 μm and/or a depth of about 1 μm to about 200 μm. In some embodiments, the cross-sectional shape of the constriction is a slit comprising a width of about 3 μm to about 6 μm and/or a depth of about 40 μm to about 120 μm. In some embodiments, the cross-sectional shape of the constriction is a slit comprising a width of about 3.2 μm to about 4 μm and/or a depth of about 20 μm to about 80 μm. In some embodiments, the cross-sectional shape of the constriction is a slit comprising a width of about 3.5 μm and/or a depth of about 80 μm. In other embodiments, the cross-sectional shape of the constriction is a slit comprising a width of about 4 μm to about 10 μm and/or a depth of about 1 μm to about 200 μm. In some embodiments, the cross-sectional shape of the constriction is a slit comprising a width of about 4.2 μm to about 6 μm and/or a depth of about 40 μm to about 120 μm. In some embodiments, the cross-sectional shape of the constriction is a slit comprising a width of about 4.2 μm to about 6 μm and/or a depth of about 20 μm to about 80 μm. In some embodiments, the cross-sectional shape of the constriction is a slit comprising a width of about 4.5 μm and/or a depth of about 80 μm. In some embodiments, the slit comprises a length of about 10 μm to about 30 μm. In some embodiments, the slit comprises a length of about 2 μm to about 50 μm. In some embodiments, the slit comprises a length of any one of about 2 μm to about 5 μm, about 5 μm to about 10 μm, about 10 μm to about 15 μm, about 15 μm to about 20 μm, about 20 μm to about 25 μm, about 25 μm to about 30 μm, about 30 μm to about 35 μm, about 35 μm to about 40 μm, about 40 μm to about 45 μm, or about 45 μm to about 50 μm. In some embodiments, the slit comprises a length of about 10 μm.

Surface Having Pores to Provide Cell Deforming Constrictions

In some embodiments, the invention provides methods for modulating an immune response by passing a cell suspension comprising a T cell through a constriction, wherein the constriction deforms the T cell thereby causing a perturbation of the T cell such that an antigen and/or adjuvant enters the T cell, wherein the constriction is a pore or contained within a pore. In some embodiments, the pore is contained in a surface. Exemplary surfaces having pores for use in the methods disclosed herein are described in WO2017041050.

The surfaces as disclosed herein can be made of any one of a number of materials and take any one of a number of forms. In some embodiments, the surface is a filter. In some embodiments, the surface is a membrane. In some embodiments, the filter is a tangential flow filter. In some embodiments, the surface is a sponge or sponge-like matrix. In some embodiments, the surface is a matrix.

In some embodiments the surface is a tortuous path surface. In some embodiments, the tortuous path surface comprises cellulose acetate. In some embodiments, the surface comprises a material selected from, without limitation, synthetic or natural polymers, polycarbonate, silicon, glass, metal, alloy, cellulose nitrate, silver, cellulose acetate, nylon, polyester, polyethersulfone, polyacrylonitrile (PAN), polypropylene, PVDF, polytetrafluorethylene, mixed cellulose ester, porcelain, and ceramic.

The surface disclosed herein can have any shape known in the art; e.g. a 3-dimensional shape. The 2-dimensional shape of the surface can be, without limitation, circular, elliptical, round, square, star-shaped, triangular, polygonal, pentagonal, hexagonal, heptagonal, or octagonal. In some embodiments, the surface is round in shape. In some embodiments, the surface 3-dimensional shape is cylindrical, conical, or cuboidal.

The surface can have various cross-sectional widths and thicknesses. In some embodiments, the surface cross-sectional width is between about 1 mm and about 1 m or any cross-sectional width or range of cross-sectional widths therebetween. In some embodiments, the surface has a defined thickness. In some embodiments, the surface thickness is uniform. In some embodiments, the surface thickness is variable. For example, in some embodiments, portions of the surface are thicker or thinner than other portions of the surface. In some embodiments, the surface thickness varies by about 1% to about 90% or any percentage or range of percentages therebetween. In some embodiments, the surface is between about 0.01 μm to about 5 mm thick or any thickness or range of thicknesses therebetween.

In some embodiments, the constriction is a pore or contained within a pore. The cross-sectional width of the pores is related to the type of T cell to be treated. In some embodiments, the pore size is a function of the diameter of the T cell or cluster of T cells to be treated. In some embodiments, the pore size is such that a T cell is perturbed upon passing through the pore. In some embodiments, the pore size is less than the diameter of the T cell. In some embodiments, the pore size is about 10% to about 99% of the diameter of the T cell. In some embodiments, the pore size is about 10%, about 15%, about 20%, about 30%, about 40%, about 50%, about 60%, about 70%, about 80%, about 90%, or about 99% of the T cell diameter. Optimal pore size or pore cross-sectional width can vary based upon the application and/or T cell type. In some embodiments, the pore size is about 2 μm to about 14 μm. In some embodiments, the pore size is about 2 μm, about 3 μm, about 4 μm, about 5 μm, about 8 μm, about 10 μm, about 12 μm, or about 14 μm. In some embodiments, the cross-sectional width is about 2 μm to about 14 μm. In some embodiments, the pore cross-sectional is about 2 μm, about 3 μm, about 4 μm, about 5 μm, about 8 μm, about 10 μm, about 12 μm, or about 14 μm.

The entrances and exits of the pore passage may have a variety of angles. The pore angle can be selected to minimize clogging of the pore while T cells are passing through. In some embodiments the flow rate through the surface is between about 0.001 mL/cm$^2$/sec to about 100 L/cm$^2$/sec or any rate or range of rates therebetween. For example, the angle of the entrance or exit portion can be between about 0 and about 90 degrees. In some embodiments, the entrance or exit portion can be greater than 90 degrees. In some embodiments, the pores have identical entrance and exit angles. In some embodiments, the pores have different entrance and exit angles. In some embodiments, the pore edge is smooth, e.g. rounded or curved. A smooth pore edge has a continuous, flat, and even surface without bumps, ridges, or uneven parts. In some embodiments, the pore edge is sharp. A sharp pore edge has a thin edge that is pointed or at an acute angle. In some embodiments, the pore passage is straight. A straight pore passage does not contain curves, bends, angles, or other irregularities. In some embodiments, the pore passage is curved. A curved pore passage is bent or deviates from a straight line. In some embodiments, the pore passage has multiple curves, e.g. about 2, 3, 4, 5, 6, 7, 8, 9, 10 or more curves.

The pores can have any shape known in the art, including a 2-dimensional or 3-dimensional shape. The pore shape (e.g., the cross-sectional shape) can be, without limitation, circular, elliptical, round, square, star-shaped, triangular, polygonal, pentagonal, hexagonal, heptagonal, and octagonal. In some embodiments, the cross-section of the pore is round in shape. In some embodiments, the 3-dimensional shape of the pore is cylindrical or conical. In some embodiments, the pore has a fluted entrance and exit shape. In some embodiments, the pore shape is homogenous (i.e. consistent or regular) among pores within a given surface. In some embodiments, the pore shape is heterogeneous (i.e. mixed or varied) among pores within a given surface.

The surfaces described herein can have a range of total pore numbers. In some embodiments, the pores encompass about 10% to about 80% of the total surface area. In some embodiments, the surface contains about $1.0\times10^5$ to about $1.0\times10^{30}$ total pores or any number or range of numbers therebetween. In some embodiments, the surface comprises between about 10 and about $1.0\times10^{15}$ pores/$mm^2$ surface area.

The pores can be distributed in numerous ways within a given surface. In some embodiments, the pores are distributed in parallel within a given surface. In one such example, the pores are distributed side-by-side in the same direction and are the same distance apart within a given surface. In some embodiments, the pore distribution is ordered or homogeneous. In one such example, the pores are distributed in a regular, systematic pattern or are the same distance apart within a given surface. In some embodiments, the pore distribution is random or heterogeneous. In one such example, the pores are distributed in an irregular, disordered pattern or are different distances apart within a given surface. In some embodiments, multiple surfaces are distributed in series. The multiple surfaces can be homogeneous or heterogeneous in surface size, shape, and/or roughness. The multiple surfaces can further contain pores with homogeneous or heterogeneous pore size, shape, and/or number, thereby enabling the simultaneous delivery of a range of compounds into different T cell types.

In some embodiments, an individual pore has a uniform width dimension (i.e. constant width along the length of the pore passage). In some embodiments, an individual pore has a variable width (i.e. increasing or decreasing width along the length of the pore passage). In some embodiments, pores within a given surface have the same individual pore depths. In some embodiments, pores within a given surface have different individual pore depths. In some embodiments, the pores are immediately adjacent to each other. In some embodiments, the pores are separated from each other by a distance. In some embodiments, the pores are separated from each other by a distance of about 0.001 μm to about 30 mm or any distance or range of distances therebetween.

In some embodiments, the surface is coated with a material. The material can be selected from any material known in the art, including, without limitation, Teflon, an adhesive coating, surfactants, proteins, adhesion molecules, antibodies, anticoagulants, factors that modulate cellular function, nucleic acids, lipids, carbohydrates, or transmembrane proteins. In some embodiments, the surface is coated with polyvinylpyrrolidone (PVP). In some embodiments, the material is covalently attached to the surface. In some embodiments, the material is non-covalently attached or adsorbed to the surface. In some embodiments, the surface molecules are released as the T cells pass through the pores.

In some embodiments, the surface has modified chemical properties. In some embodiments, the surface is polar. In some embodiments, the surface is hydrophilic. In some embodiments, the surface is non-polar. In some embodiments, the surface is hydrophobic. In some embodiments, the surface is charged. In some embodiments, the surface is positively and/or negatively charged. In some embodiments, the surface can be positively charged in some regions and negatively charged in other regions. In some embodiments, the surface has an overall positive or overall negative charge. In some embodiments, the surface can be any one of smooth, electropolished, rough, or plasma treated. In some embodiments, the surface comprises a zwitterion or dipolar compound. In some embodiments, the surface is plasma treated.

In some embodiments, the surface is contained within a larger module. In some embodiments, the surface is contained within a syringe, such as a plastic or glass syringe. In some embodiments, the surface is contained within a plastic filter holder. In some embodiments, the surface is contained within a pipette tip.

Cell Perturbations

In some embodiments, the invention provides methods for modulating an immune response by passing a cell suspension comprising a T cell through a constriction, wherein the constriction deforms the T cell thereby causing a perturbation of the T cell such that an antigen and/or adjuvant enters the T cell, wherein the perturbation in the T cell is a breach in the T cell that allows material from outside the T cell to move into the T cell (e.g., a hole, tear, cavity, aperture, pore, break, gap, perforation). The deformation can be caused by, for example, mechanical strain and/or shear forces. In some embodiments, the perturbation is a perturbation within the T cell membrane. In some embodiments, the perturbation is transient. In some embodiments, the T cell perturbation lasts from about $1.0\times10^{--9}$ seconds to about 2 hours, or any time or range of times therebetween. In some embodiments, the T cell perturbation lasts for about $1.0\times10^{-9}$ second to about 1 second, about 1 second to about 1 minute, or about 1 minute to about 1 hour. In some embodiments, the T cell perturbation lasts for between any one of about $1.0\times10^{-9}$ to about $1.0\times10^{-1}$, about $1.0\times10^{-9}$ to about $1.0\times10^{-2}$, about $1.0\times10^{-9}$ to about $1.0\times10^{-3}$, about $1.0\times10^{-9}$ to about $1.0\times10^{-4}$, about $1.0\times10^{-9}$ to about $1.0\times10^{-5}$, about $1.0\times10^{-9}$ to about $1.0\times10^{-6}$, about $1.0\times10^{-9}$ to about $1.0\times10^{-7}$, or about $1.0\times10^{-9}$ to about $1.0\times10^{-8}$ seconds. In some embodiment, the T cell perturbation lasts for any one of about $1.0\times10^{-8}$ to about $1.0\times10^{-1}$, about $1.0\times10^{-7}$ to about $1.0\times10^{-1}$, about $1.0\times10^{-6}$ to about $1.0\times10^{-1}$, about $1.0\times10^{-5}$ to about $1.0\times10^{-1}$, about $1.0\times10^{-4}$ to about $1.0\times10^{-1}$, about $1.0\times10^{-3}$ to about $1.0\times10^{-1}$, or about $1.0\times10^{-2}$ to about $1.0\times10^{-1}$ seconds. The T cell perturbations (e.g., pores or holes) created by the methods described herein are not formed as a result of assembly of protein subunits to form a multimeric pore structure such as that created by complement or bacterial hemolysins.

As the T cell passes through the constriction, the constriction temporarily imparts injury to the T cell membrane that allows for passive diffusion of material through the perturbation. In some embodiments, the T cell is only deformed for a brief period of time, on the order of 100 μs to minimize the chance of activating apoptotic pathways through cell signaling mechanisms, although other durations are possible (e.g., ranging from nanoseconds to hours). In some embodiments, the T cell is deformed for about 1.0×

$10^{-9}$ seconds to about 2 hours, or any time or range of times therebetween. In some embodiments, the T cell is deformed for about $1.0\times10^{-9}$ second to about 1 second, about 1 second to about 1 minute, or about 1 minute to about 1 hour. In some embodiments, the T cell is deformed for between any one of about $1.0\times10^{-9}$ to about $1.0\times10^{-1}$, about $1.0\times10^{-9}$ to about $1.0\times10^{-2}$, about $1.0\times10^{-9}$ to about $1.0\times10^{-3}$, about $1.0\times10^{-9}$ to about $1.0\times10^{-4}$, about $1.0\times10^{-9}$ to about $1.0\times10^{-5}$, about $1.0\times10^{-9}$ to about $1.0\times10^{-6}$, about $1.0\times10^{-9}$ to about $1.0\times10^{-7}$, or about $1.0\times10^{-9}$ to about $1.0\times10^{-8}$ seconds. In some embodiment, the T cell is deformed for any one of about $1.0\times10^{-8}$ to about $1.0\times10^{-1}$, about $1.0\times10^{-7}$ to about $1.0\times10^{-1}$, about $1.0\times10^{-6}$ to about $1.0\times10^{-1}$, about $1.0\times10^{-5}$ to about $1.0\times10^{-1}$, about $1.0\times10^{-4}$ to about $1.0\times10^{-1}$, about $1.0\times10^{-3}$ to about $1.0\times10^{-1}$, or about $1.0\times10^{-2}$ to about $1.0\times10^{-1}$ seconds. In some embodiments, deforming the T cell includes deforming the T cell for a time ranging from, without limitation, about 1 μs to at least about 750 μs, e.g., at least about 1 μs, 10 μs, 50 μs, 100 μs, 500 μs, or 750 μs.

In some embodiments, the passage of the antigen and/or adjuvant into the T cell occurs simultaneously with the T cell passing through the constriction and/or the perturbation of the T cell. In some embodiments, passage of the compound into the T cell occurs after the T cell passes through the constriction. In some embodiments, passage of the compound into the T cell occurs on the order of minutes after the T cell passes through the constriction. In some embodiments, the passage of the compound into the T cell occurs from about $1.0\times10^{-2}$ seconds to at least about 30 minutes after the T cell passes through the constriction. For example, the passage of the compound into the T cell occurs from about $1.0\times10^{-2}$ seconds to about 1 second, about 1 second to about 1 minute, or about 1 minute to about 30 minutes after the T cell passes through the constriction. In some embodiments, the passage of the compound into the T cell occurs about $1.0\times10^{-2}$ seconds to about 10 minutes, about $1.0\times10^{-2}$ seconds to about 5 minutes, about $1.0\times10^{-2}$ seconds to about 1 minute, about $1.0\times10^{-2}$ seconds to about 30 seconds, about $1.0\times10^{-2}$ seconds to about 10 seconds, about $1.0\times10^{-2}$ seconds to about 1 second, or about $1.0\times10^{-2}$ seconds to about 0.1 second after the T cell passes through the constriction. In some embodiments, the passage of the compound into the T cell occurs about $1.0\times10^{1}$ seconds to about 10 minutes, about 1 second to about 10 minutes, about 10 seconds to about 10 minutes, about 50 seconds to about 10 minutes, about 1 minute to about 10 minutes, or about 5 minutes to about 10 minutes after the T cell passes through the constriction. In some embodiments, a perturbation in the T cell after it passes through the constriction is corrected within the order of about five minutes after the T cell passes through the constriction.

In some embodiments, the cell viability after passing through a constriction is about 5% to about 100%. In some embodiments, the cell viability after passing through the constriction is at least about 5%, 10%, 20%, 30%, 40%, 50%, 60%, 70%, 75%, 80%, 85%, 90%, 95%, or 99%. In some embodiments, the cell viability is measured from about $1.0\times10^{-2}$ seconds to at least about 10 days after the T cell passes through the constriction. For example, the cell viability is measured from about $1.0\times10^{-2}$ seconds to about 1 second, about 1 second to about 1 minute, about 1 minute to about 30 minutes, or about 30 minutes to about 2 hours after the T cell passes through the constriction. In some embodiments, the cell viability is measured about $1.0\times10^{-2}$ seconds to about 2 hours, about $1.0\times10^{-2}$ seconds to about 1 hour, about $1.0\times10^{-2}$ seconds to about 30 minutes, about $1.0\times10^{-2}$ seconds to about 1 minute, about $1.0\times10^{-2}$ seconds to about 30 seconds, about $1.0\times10^{-2}$ seconds to about 1 second, or about $1.0\times10^{-2}$ seconds to about 0.1 second after the T cell passes through the constriction. In some embodiments, the cell viability is measured about 1.5 hours to about 2 hours, about 1 hour to about 2 hours, about 30 minutes to about 2 hours, about 15 minutes to about 2 hours, about 1 minute to about 2 hours, about 30 seconds to about 2 hours, or about 1 second to about 2 hours after the T cell passes through the constriction. In some embodiments, the cell viability is measured about 2 hours to about 5 hours, about 5 hours to about 12 hours, about 12 hours to about 24 hours, or about 24 hours to about 10 days after the T cell passes through the constriction.

Delivery Parameters

A number of parameters may influence the delivery of a compound to a T cell for modulating an immune response by the methods described herein. In some embodiments, the cell suspension is contacted with the compound before, concurrently, or after passing through the constriction. The T cell may pass through the constriction suspended in a solution that includes the compound to deliver, although the compound can be added to the cell suspension after the T cells pass through the constriction. In some embodiments, the compound to be delivered is coated on the constriction.

Examples of parameters that may influence the delivery of the compound into the T cell include, but are not limited to, the dimensions of the constriction, the entrance angle of the constriction, the surface properties of the constrictions (e.g., roughness, chemical modification, hydrophilic, hydrophobic, etc.), the operating flow speeds (e.g., cell transit time through the constriction), the T cell concentration, the concentration of the compound in the cell suspension, and the amount of time that the T cell recovers or incubates after passing through the constrictions can affect the passage of the delivered compound into the T cell. Additional parameters influencing the delivery of the compound into the T cell can include the velocity of the T cell in the constriction, the shear rate in the constriction, the viscosity of the cell suspension, the velocity component that is perpendicular to flow velocity, and time in the constriction. Such parameters can be designed to control delivery of the compound. In some embodiments, the T cell concentration ranges from about 10 to at least about $10^{12}$ cells/mL or any concentration or range of concentrations therebetween. In some embodiments, delivery compound concentrations can range from about 10 ng/mL to about 1 g/mL or any concentration or range of concentrations therebetween. In some embodiments, delivery compound concentrations can range from about 1 pM to at least about 2 M or any concentration or range of concentrations therebetween.

The temperature used in the methods of the present disclosure can be adjusted to affect compound delivery and cell viability. In some embodiments, the method is performed between about −5° C. and about 45° C. For example, the methods can be carried out at room temperature (e.g., about 20° C.), physiological temperature (e.g., about 37° C.), higher than physiological temperature (e.g., greater than about 37° C. to 45° C. or more), or reduced temperature (e.g., about −5° C. to about 4° C.), or temperatures between these exemplary temperatures.

Various methods can be utilized to drive the T cells through the constrictions. For example, pressure can be applied by a pump on the entrance side (e.g., compressor), a vacuum can be applied by a vacuum pump on the exit side, capillary action can be applied through a tube, and/or the system can be gravity fed. Displacement based flow systems can also be used (e.g., syringe pump, peristaltic pump, manual syringe or pipette, pistons, etc.). In some embodiments, the T cells are passed through the constrictions by positive pressure or negative pressure. In some embodiments, the T cells are passed through the constrictions by constant pressure or variable pressure. In some embodiments, pressure is applied using a syringe. In some embodiments, the pressure is positive pressure applied using a gas (e.g., from a gas cylinder). In some embodiments, pressure is applied using a pump. In some embodiments, the pump is a peristaltic pump or a diaphragm pump. In some embodiments, pressure is applied using a vacuum. In some embodiments, the T cells are passed through the constrictions by g-force. In some embodiments, the T cells are passed through the constrictions by centrifugal force. In some embodiments, the T cells are passed through the constrictions by capillary pressure.

In some embodiments, fluid flow directs the T cells through the constrictions. In some embodiments, the fluid flow is turbulent flow prior to the T cells passing through the constriction. Turbulent flow is a fluid flow in which the velocity at a given point varies erratically in magnitude and direction. In some embodiments, the fluid flow through the constriction is laminar flow. Laminar flow involves uninterrupted flow in a fluid near a solid boundary in which the direction of flow at every point remains constant. In some embodiments, the fluid flow is turbulent flow after the T cells pass through the constriction. The velocity at which the T cells pass through the constrictions can be varied. In some embodiments, the T cells pass through the constrictions at a uniform cell speed. In some embodiments, the T cells pass through the constrictions at a fluctuating cell speed.

In other embodiments, a combination treatment is used to modulate an immune response by passing a cell suspension comprising a T cell through a constriction, wherein the constriction deforms the T cell thereby causing a perturbation of the T cell such that an antigen and/or adjuvant enters the T cell, e.g., the methods described herein, followed by exposure to an electric field downstream of the constriction. In some embodiments, the T cell is passed through an electric field generated by at least one electrode after passing through the constriction. In some embodiments, the electric field assists in delivery of compounds to a second location inside the T cell such as the T cell nucleus. For example, the combination of a cell-deforming constriction and an electric field delivers a plasmid encoding an antibody into the T cell (e.g., the cell nucleus), resulting in the de novo production of antibody. In some embodiments, one or more electrodes are in proximity to the cell-deforming constriction to generate an electric field. In some embodiments, the electric field is between about 0.1 kV/m to about 100 MV/m, or any number or range of numbers therebetween. In some embodiments, an integrated circuit is used to provide an electrical signal to drive the electrodes. In some embodiments, the T cells are exposed to the electric field for a pulse width of between about 1 ns to about 1 s and a period of between about 100 ns to about 10 s or any time or range of times therebetween.

Cell Suspensions for Delivery to T Cells

The cell suspension may be a mixed or purified population of T cells. In some embodiments, the cell suspension is a mixed cell population, such as whole blood. In some embodiments, the cell suspension is a purified cell population, such as a purified population of T cells.

The composition of the cell suspension (e.g., osmolarity, salt concentration, serum content, cell concentration, pH, etc.) can impact delivery of the compound for modulating an immune response. In some embodiments, the suspension comprises whole blood. Alternatively, the cell suspension is a mixture of cells in a physiological saline solution or physiological medium other than blood. In some embodiments, the cell suspension comprises an aqueous solution. In some embodiments, the aqueous solution comprises cell culture medium, phosphate buffered saline (PBS), salts, metal ions, sugars, growth factors, animal derived products, bulking materials, surfactants, lubricants, lipids, vitamins, amino acids, proteins, cell cycle inhibitors, and/or an agent that impacts actin polymerization. In some embodiments, the cell culture medium is DMEM, Opti-MEM®, EIDM, RPMI, X-Vivo 10, and X-Vivo 15. Additionally, solution buffer can include one or more lubricants (pluronics or other surfactants) that can be designed, for example, to reduce or eliminate clogging of the constriction or pore and improve cell viability. Exemplary surfactants include, without limitation, poloxamer, polysorbates, sugars or sugar alcohols such as mannitol, sorbitol, animal derived serum, and albumin protein.

In some configurations with certain types of T cells, the T cells can be incubated in one or more solutions that aid in the delivery of the compound to the interior of the T cell. In some embodiments, the aqueous solution comprises an agent that impacts actin polymerization. In some embodiments, the agent that impacts actin polymerization is Latrunculin A, Cytochalasin, and/or Colchicine. For example, the T cells can be incubated in a depolymerization solution such as Lantrunculin A (0.1 μg/mL) for 1 hour prior to delivery to depolymerize the actin cytoskeleton. As an additional example, the T cells can be incubated in 10 M Colchicine (Sigma) for 2 hours prior to delivery to depolymerize the microtubule network.

In some embodiments, the cell population is enriched prior to use in the disclosed methods. For example, cells are obtained from a bodily fluid, e.g., peripheral blood, and optionally enriched or purified to concentrate T cells. Cells may be enriched by any methods known in the art, including without limitation, magnetic cell separation, fluorescent activated cell sorting (FACS), or density gradient centrifugation.

The viscosity of the cell suspension can also impact the methods disclosed herein. In some embodiments, the viscosity of the cell suspension ranges from about $8.9\times10^{-4}$ Pa·s to about $4.0\times10^{-3}$ Pa·s or any value or range of values therebetween. In some embodiments, the viscosity ranges between any one of about $8.9\times10^{-4}$ Pa·s to about $4.0\times10^{-3}$ Pa·s, about $8.9\times10^{-4}$ Pa·s to about $3.0\times10^{-3}$ Pa·s, about $8.9\times10^{-4}$ Pa·s to about $2.0\times10^{-3}$ Pa·s, or about $8.9\times10^{-3}$ Pa·s to about $1.0\times10^{-3}$ Pa·s. In some embodiments, the viscosity ranges between any one of about 0.89 cP to about 4.0 cP, about 0.89 cP to about 3.0 cP, about 0.89 cP to about 2.0 cP, or about 0.89 cP to about 1.0 cP. In some embodiments, a shear thinning effect is observed, in which the viscosity of the cell suspension decreases under conditions of shear strain. Viscosity can be measured by any method known in the art, including without limitation, viscometers, such as a glass capillary viscometer, or rheometers. A viscometer measures viscosity under one flow condition, while a rheometer is used to measure viscosities which vary with flow conditions. In some embodiments, the viscosity is measured for a shear thinning solution such as blood. In some embodiments, the viscosity is measured between about −5° C. and about 45° C. For example, the viscosity is measured at room temperature (e.g., about 20° C.), physiological temperature (e.g., about 37° C.), higher than physiological temperature (e.g., greater than about 37° C. to 45° C. or more), reduced temperature (e.g., about −5° C. to about 4° C.), or temperatures between these exemplary temperatures.

Systems and Kits

In some aspects, the invention provides a system comprising one or more of a constriction, a T cell suspension, antigens or adjuvants according to any of the embodiments described herein, such as for use in any of the methods described herein. The system can include any embodiment described for the compositions of matter and methods disclosed herein, including those disclosed in the above section titled "Microfluidic systems and components thereof" In some embodiment, the cell-deforming constrictions are sized for delivery to T cells. In some embodiments, the delivery parameters, such as operating flow speeds, cell and compound concentration, temperature, velocity of the cell in the constriction, and the composition of the cell suspension (e.g., osmolarity, salt concentration, serum content, cell concentration, pH, etc.) are optimized for maximum response of a compound for modulating an immune response.

Also provided are kits or articles of manufacture for use in modulating an immune response in an individual. In some embodiments, the kit comprises a modified T cell comprising an antigen and/or an adjuvant, including any of the modified T cells described herein. In some embodiments, the kit comprises one or more of a constriction, a T cell suspension, antigens or adjuvants for use in generating modified T cells for use in modulating an immune response in an individual. In some embodiments, the kits comprise components described herein (e.g. a microfluidic channel or surface containing pores, cell suspensions, and/or compounds) in suitable packaging. Suitable packaging materials are known in the art, and include, for example, vials (such as sealed vials), vessels, ampules, bottles, jars, flexible packaging (e.g., sealed Mylar or plastic bags), and the like. These articles of manufacture may further be sterilized and/or sealed.

The invention also provides kits comprising components of the methods described herein and may further comprise instructions for performing said methods to modulate an immune response in an individual and/or instructions for introducing an antigen and/or an adjuvant into a T cell. The kits described herein may further include other materials, including buffers, diluents, filters, needles, syringes, and package inserts with instructions for performing any of the methods described herein; e.g., instructions for modulating an immune response in an individual or instructions for modifying a T cell to contain an antigen and/or an adjuvant.

Exemplary Embodiments

Embodiment 1. A modified T cell comprising an antigen and an adjuvant, wherein the antigen is exogenous to the modified T cell and comprises an immunogenic epitope, and wherein the adjuvant is present intracellularly.

Embodiment 2. A modified T cell comprising an antigen comprising the amino acid sequence of any one of SEQ ID NOs: 18-25.

Embodiment 3. A modified T cell comprising an antigen and an adjuvant, wherein the antigen comprises an immunogenic epitope, prepared by a process comprising the steps of a) passing a cell suspension comprising an input T cell through a cell-deforming constriction, wherein a diameter of the constriction is a function of a diameter of the input T cell in the suspension, thereby causing perturbations of the input T cell large enough for the antigen and the adjuvant to pass through to form a perturbed input T cell; and b) incubating the perturbed input T cell with the antigen and the adjuvant for a sufficient time to allow the antigen and the adjuvant to enter the perturbed input T cell; thereby generating the modified T cell comprising the antigen and adjuvant.

Embodiment 4. The modified T cell of embodiment 3, wherein the concentration of the antigen incubated with the perturbed input T cell is between about 0.1 μM and about 1 mM and/or the concentration of the adjuvant incubated with the perturbed input T cell is between about 0.1 μM and about 1 mM.

Embodiment 5. The modified T cell of embodiment 3 or 4, wherein the ratio of the antigen to the adjuvant incubated with the perturbed input T cell is between about 10000:1 to about 1:10000.

Embodiment 6. A modified T cell comprising an antigen and an adjuvant, wherein the antigen comprises an immunogenic epitope, prepared by a process comprising the steps of: a) passing a cell suspension comprising an input T cell comprising the adjuvant through a cell-deforming constriction, wherein a diameter of the constriction is a function of a diameter of the input T cell in the suspension, thereby causing perturbations of the input T cell large enough for the antigen to pass through to form a perturbed input T cell; and b) incubating the perturbed input T cell with the antigen for a sufficient time to allow the antigen to enter the perturbed input T cell, thereby generating the modified T cell comprising the antigen and the adjuvant.

Embodiment 7. The modified T cell of embodiment 6, wherein the concentration of the antigen incubated with the perturbed input T cell is between about 0.1 μM and about 1 mM.

Embodiment 8. A modified T cell comprising an antigen and an adjuvant, wherein the antigen comprises an immunogenic epitope, prepared by a process comprising the steps of: a) passing a cell suspension comprising an input T cell comprising the antigen through a cell-deforming constriction, wherein a diameter of the constriction is a function of a diameter of the input T cell in the suspension, thereby causing perturbations of the input T cell large enough for the adjuvant to pass through to form a perturbed input T cell; and b) incubating the perturbed input T cell with the adjuvant for a sufficient time to allow the adjuvant to enter the perturbed input T cell, thereby generating the modified T cell comprising the antigen and the adjuvant.

Embodiment 9. The modified T cell of embodiment 8, wherein the concentration of the adjuvant incubated with the perturbed input T cell is between about 0.1 μM and about 1 mM.

Embodiment 10. The modified T cell of any one of embodiments 3-9, wherein a deforming force is applied to the input T cell as it passes through the constriction, thereby causing the perturbations of the input T cell.

Embodiment 11. The modified T cell of any one of embodiments 3-10, wherein the process further comprises a step of incubating the input T cell and/or the modified T cell with an agent that enhances the viability and/or function of the modified T cell as compared to a corresponding modified T cell prepared without the further incubation step.

Embodiment 12. The modified T cell of embodiment 11, wherein the agent is a compound that enhances endocytosis, or acts as a stabilizing agent or a co-factor.

Embodiment 13. The modified T cell of any one of embodiments 3-12, wherein the diameter of the constriction is less than the diameter of the input T cell.

Embodiment 14. The modified T cell of embodiment 13, wherein the diameter of the constriction is about 20% to about 99% of the diameter of the input T cell.

Embodiment 15. The modified T cell of embodiment 14, wherein the diameter of the constriction is about 20% to about 60% of the diameter of the input T cell.

Embodiment 16. The modified T cell of any one of embodiments 1-15, wherein the antigen and/or adjuvant are present in the cytosol and/or a vesicle of the modified T cell.

Embodiment 17. The modified T cell of any one of embodiments 1-16, wherein the vesicle is an endosome.

Embodiment 18. The modified T cell of any one of embodiments 1-17, wherein the antigen and/or the adjuvant are present in multiple compartments of the modified T cell.

Embodiment 19. The modified T cell of any one of embodiments 1-18, wherein the antigen or immunogenic epitope is bound to the surface of the modified T cell.

Embodiment 20. The modified T cell of any one of embodiments 1-19, wherein the adjuvant is a CpG oligodeoxynucleotide (ODN), IFN-α, STING agonists, RIG-I agonists, poly I.C, imiquimod, resiquimod, or lipopolysaccharide (LPS)

Embodiment 21. The modified T cell of embodiment 20, wherein the adjuvant is a CpG ODN.

Embodiment 22. The modified T cell of embodiment 21, wherein the CpG ODN is a Class A CpG ODN, a Class B CpG ODN, or a Class C CpG ODN.

Embodiment 23. The modified T cell of any one of embodiments 1-22, wherein the immunogenic epitope is derived from a disease-associated antigen.

Embodiment 24. The modified T cell of embodiment 23, wherein the immunogenic epitope is derived from peptides or mRNA isolated from a diseased cell.

Embodiment 25. The modified T cell of any one of embodiments 1-24, wherein the immunogenic epitope is derived from a non-self antigen.

Embodiment 26. The modified T cell of any one of embodiments 1-25, wherein the immunogenic epitope is derived from a tumor antigen, viral antigen, bacterial antigen, or fungal antigen.

Embodiment 27. The modified T cell of embodiment 26, wherein the immunogenic epitope is derived from a human papillomavirus (HPV) antigen.

Embodiment 28. The modified T cell of embodiment 27, wherein the HPV is HPV-16 or HPV-18.

Embodiment 29. The modified T cell of embodiment 27 or 28, wherein the antigen comprises an HLA-A2-restricted peptide derived from HPV E6 and/or E7.

Embodiment 30. The modified T cell of embodiment 29, wherein the HLA-A2-restricted peptide comprises the amino acid sequence of any one of SEQ ID NOs: 1-4.

Embodiment 31. The modified T cell of embodiment 30, wherein the antigen comprises the amino acid sequence of any one of SEQ ID NOs: 18-25.

Embodiment 32. The modified T cell of any one of embodiments 1-30, wherein the modified T cell comprises a plurality of antigens that comprise a plurality of immunogenic epitopes.

Embodiment 33. The modified T cell of embodiment 32, wherein following administration to an individual of the modified T cell comprising the plurality of antigens that comprise the plurality of immunogenic epitopes, none of the plurality of immunogenic epitopes decreases an immune response in the individual to any of the other immunogenic epitopes.

Embodiment 34. The modified T cell of any one of embodiments 1-33, wherein the antigen is a polypeptide and the immunogenic epitope is an immunogenic peptide epitope.

Embodiment 35. The modified T cell of embodiment 30, wherein the immunogenic peptide epitope is fused to an N-terminal flanking polypeptide and/or a C-terminal flanking polypeptide.

Embodiment 36. The modified T cell of embodiment 30, wherein the antigen is a polypeptide comprising an immunogenic peptide epitope and one or more heterologous peptide sequences.

Embodiment 37. The modified T cell of embodiment 34, wherein the antigen is a polypeptide comprising an immunogenic peptide epitope that is flanked on the N-terminus and/or the C-terminus by heterologous peptide sequences Embodiment 38. The modified T cell of embodiment 35, wherein the flanking heterologous peptide sequences are derived from a disease-associated immunogenic peptides.

Embodiment 39. The modified T cell of embodiment 35, wherein the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17.

Embodiment 40. The modified T cell of any one of embodiments 1-39, wherein the antigen is capable of being processed into an MHC class I-restricted peptide and/or an MHC class II-restricted peptide.

Embodiment 41. The modified T cell of any one of embodiments 1-40, wherein the modified T cell comprises the adjuvant at a concentration between about 0.1 μM and about 1 mM.

Embodiment 42. The modified T cell of any one of embodiments 1-41, wherein the modified T cell comprises the antigen at a concentration between about 0.1 μM and about 1 mM.

Embodiment 43. The modified T cell of any one of embodiments 1-42, wherein the ratio of the antigen to the adjuvant is between about 10000:1 to about 1:10000.

Embodiment 44. The modified T cell of any one of embodiments 1-43, wherein the modified T cell comprises a complex comprising: a) the antigen, b) the antigen and at least one other antigen, and/or c) the antigen and the adjuvant.

Embodiment 45. The modified T cell of any one of embodiments 1-44, wherein the modified T cell further comprises an agent that enhances the viability and/or function of the modified T cell as compared to a corresponding modified T cell that does not comprise the agent.

Embodiment 46. The modified T cell of embodiment 45, wherein the agent is a compound that enhances endocytosis, a stabilizing agent or a co-factor.

Embodiment 47. The modified T cell of embodiment 45, wherein the agent is albumin.

Embodiment 48. The modified T cell of embodiment 47, wherein the albumin is mouse, bovine, or human albumin.

Embodiment 49. The modified T cell of embodiment 45, wherein the agent is a divalent metal cation, glucose, ATP, potassium, glycerol, trehalose, D-sucrose, PEG1500, L-arginine, L-glutamine, or EDTA.

Embodiment 50. The modified T cell of embodiment 49, wherein the agent comprises mouse serum albumin (MSA).

Embodiment 51. The modified T cell of any one of embodiments 1-50, wherein the cells are further modified to increase expression of one or more of co-stimulatory molecules.

Embodiment 52. The modified T cell of embodiment 51, wherein the co-stimulatory molecule is B7-H2 (ICOSL), B7-1 (CD80), B7-2 (CD86), CD70, LIGHT, HVEM, CD40, 4-1BBL, OX40L, TL1A, GITRL, CD30L, TIM4, SLAM, CD48, CD58, CD155, or CD112.

Embodiment 53. The modified T cell of embodiments 51 or 52, wherein the cell comprises a nucleic acid that results in increased expression of the one or more co-stimulatory molecules.

Embodiment 54. The modified T cell of any one of embodiments 1-53, wherein the modified T cell comprises a further modification to modulate MHC class I expression.

Embodiment 55. The modified T cell of any one of embodiments 1-54, wherein the modified T cell comprises a further modification to modulate MHC class II expression.

Embodiment 56. The modified T cell of embodiment 54, wherein an innate immune response mounted in an individual in response to administration, in an allogeneic context, of the modified T cells is reduced compared to an innate immune response mounted in an individual in response to administration, in an allogeneic context, of corresponding modified T cells that do not comprise the further modification.

Embodiment 57. The modified T cell of embodiment 54 or 56, wherein the circulating half-life of the modified T cells in an individual to which they were administered is increased compared to the circulating half-life of corresponding modified T cells that do not comprise the further modification in an individual to which they were administered.

Embodiment 58. The modified T cell of any one of embodiments 1-57, wherein the modified T cell includes one or more of helper T cells, cytotoxic T cells, memory T cells, or natural killer T cells.

Embodiment 59. The modified T cell of any one of embodiments 1-58, wherein the modified T cell includes one or more of CD3+ T cells, CD4+ T cells, CD8+ T cells, CD45RA+ T cells, CD45RO+ T cells, or γδ-T cells.

Embodiment 60. A composition comprising the modified T cell of any one of embodiments 1-59.

Embodiment 61. A pharmaceutical composition comprising the modified T cell of any one of embodiments 1-59 and a pharmaceutically acceptable carrier.

Embodiment 62. A method for modulating an immune response in an individual, comprising administering to the individual the modified T cell of any one of embodiments 1-59, the composition of embodiment 60, or the pharmaceutical composition of embodiment 61.

Embodiment 63. A method for modulating an immune response in an individual, comprising: a) administering a modified T cell comprising an antigen comprising the amino acid sequence of any one of SEQ ID NOs: 18-25 to the individual; and b) administering an adjuvant to the individual.

Embodiment 64. A method for modulating an immune response in an individual, comprising: a) passing a cell suspension comprising an input T cell through a cell-deforming constriction, wherein a diameter of the constriction is a function of a diameter of the input T cell in the suspension, thereby causing perturbations of the input T cell large enough for an antigen and an adjuvant to pass through to form a perturbed input T cell, wherein the antigen comprises an immunogenic epitope; b) incubating the perturbed input T cell with the antigen and the adjuvant for a sufficient time to allow the antigen and the adjuvant to enter the perturbed input T cell, thereby generating a modified T cell comprising the antigen and adjuvant; and c) administering the modified T cell to the individual.

Embodiment 65. The method of embodiment 64, wherein the concentration of the antigen incubated with the perturbed input T cell is between about 0.1 μM and about 1 mM and/or the concentration of the adjuvant incubated with the perturbed input T cell is between about 0.1 μM and about 1 mM.

Embodiment 66. The method of embodiment 64 or 65, wherein the ratio of the antigen to the adjuvant incubated with the perturbed input T cell is between about 10000:1 to about 1:10000.

Embodiment 67. A method for modulating an immune response in an individual, comprising: a) passing a cell suspension comprising an input T cell comprising an adjuvant through a cell-deforming constriction, wherein a diameter of the constriction is a function of a diameter of the input T cell in the suspension, thereby causing perturbations of the input T cell large enough for an antigen to pass through to form a perturbed input T cell, wherein the antigen comprises an immunogenic epitope; b) incubating the perturbed input T cell with the antigen for a sufficient time to allow the antigen to enter the perturbed input T cell, thereby generating a modified T cell comprising the antigen and the adjuvant; and c) administering the modified T cell to the individual.

Embodiment 68. The method of embodiment 67, wherein the concentration of the antigen incubated with the perturbed input T cell is between about 0.1 μM and about 1 mM.

Embodiment 69. A method for modulating an immune response in an individual, comprising: a) passing a cell suspension comprising an input T cell comprising an antigen through a cell-deforming constriction, wherein the antigen comprises an immunogenic epitope, wherein a diameter of the constriction is a function of a diameter of the input T cell in the suspension, thereby causing perturbations of the input T cell large enough for an adjuvant to pass through to form a perturbed input T cell; b) incubating the perturbed input T cell with the adjuvant for a sufficient time to allow the adjuvant to enter the perturbed input T cell, thereby generating a modified T cell comprising the antigen and the adjuvant; and c) administering the modified T cell to the individual.

Embodiment 70. The method of embodiment 69, wherein the concentration of the adjuvant incubated with the perturbed input T cell is between about 0.1 μM and about 1 mM.

Embodiment 71. The method of any one of embodiments 64-70, wherein the modified T cell comprises the antigen at a concentration between about 0.1 μM and about 1 mM.

Embodiment 72. The method of any one of embodiments 64-71, wherein the modified T cell comprises the adjuvant at a concentration between about 0.1 μM and about 1 mM.

Embodiment 73. The method of any one of embodiments 64-72, wherein the ratio of the antigen to the adjuvant in the modified T cell is between about 10000:1 and about 1:10000.

Embodiment 74. The method of any one of embodiments 64-73, wherein the modified T cell comprises a complex comprising: a) the antigen, b) the antigen and at least one other antigen, and/or c) the antigen and the adjuvant.

Embodiment 75. A method for modulating an immune response in an individual, comprising: a) passing a cell suspension comprising an input T cell through a cell-deforming constriction, wherein a diameter of the constriction is a function of a diameter of the input T cell in the suspension, thereby causing perturbations of the input T cell large enough for an antigen to pass through to form a perturbed input T cell, wherein the antigen comprises an immunogenic epitope; b) incubating the perturbed input T cell with the antigen for a sufficient time to allow the antigen to enter the perturbed input T cell, thereby generating a modified T cell comprising the antigen; c) administering the modified T cell to the individual; and d) administering an adjuvant to the individual.

Embodiment 76. The method of embodiment 75, wherein the concentration of the antigen incubated with the perturbed input T cell is between about 0.1 μM and about 1 mM.

Embodiment 77. The method of any one of embodiments 64-76, wherein a deforming force is applied to the input T cell as it passes through the constriction, thereby causing the perturbations of the input T cell.

Embodiment 78. The method of any one of embodiments 64-77, further comprising a step of incubating the input T cell and/or modified T cell with an agent that enhances the viability and/or function of the modified T cell as compared to a corresponding modified T cell prepared without the further incubation step.

Embodiment 79. The method of embodiment 78, wherein the agent is a compound that enhances endocytosis, a stabilizing agent, or a co-factor.

Embodiment 80. The method of any one of embodiments 64-79, wherein the immune response is enhanced.

Embodiment 81. The method of embodiment 80, wherein the enhanced immune response is directed towards the antigen.

Embodiment 82. The method of any one of embodiments 64-81, wherein the diameter of the constriction is less than the diameter of the input T cell.

Embodiment 83. The method of embodiment 82, wherein the diameter of the constriction is about 20% to about 99% of the diameter of the input T cell.

Embodiment 84. The method of embodiment 83, wherein the diameter of the constriction is about 20% to about 60% of the diameter of the input T cell.

Embodiment 85. The method of any one of embodiments 64-84, wherein the antigen and/or adjuvant are present in the cytosol and/or a vesicle of the modified T cell.

Embodiment 86. The method of any one of embodiments 64-85, wherein the vesicle is an endosome.

Embodiment 87. The method of any one of embodiments 64-86, wherein the antigen and/or the adjuvant are present in multiple compartments of the modified T cell.

Embodiment 88. The method of any one of embodiments 64-87, wherein the antigen or immunogenic epitope is bound to the surface of the modified T cell.

Embodiment 89. The method of any one of embodiments 64-88, wherein the adjuvant is a CpG ODN, IFN-α, STING agonists, RIG-I agonists, poly I:C, imiquimod, resiquimod, and/or lipopolysaccharide (LPS).

Embodiment 90. The method of embodiment 89, wherein the adjuvant is a CpG ODN.

Embodiment 91. The method of embodiment 90, wherein the CpG ODN is a Class A CpG ODN, a Class B CpG ODN, or a Class C CpG ODN.

Embodiment 92. The method of any one of embodiments 64-91, wherein the immunogenic epitope is derived from a disease-associated antigen.

Embodiment 93. The method of embodiment 92, wherein the immunogenic epitope is derived from peptides or mRNA isolated from a diseased cell.

Embodiment 94. The method of any one of embodiments 64-93, wherein the immunogenic epitope is derived from a non-self antigen.

Embodiment 95. The method of any one of embodiments 64-94, wherein the immunogenic epitope is derived from a tumor antigen, viral antigen, bacterial antigen, or fungal antigen.

Embodiment 96. The method of embodiment 95, wherein the immunogenic epitope is derived from a human papillomavirus (HPV) antigen.

Embodiment 97. The method of embodiment 96, wherein the HPV is HPV-16 or HPV-18.

Embodiment 98. The method of embodiment 96 or 97, wherein the antigen comprises an HLA-A2-restricted peptide derived from HPV E6 and/or E7.

Embodiment 99. The method of embodiment 98, wherein the HLA-A2-restricted peptide comprises the amino acid sequence of any one of SEQ ID NOs: 1-4.

Embodiment 100. The method of embodiment 99, wherein the antigen comprises the amino acid sequence of any one of SEQ ID NOs: 18-25.

Embodiment 101. The method of any one of embodiments 64-100, wherein the modified T cell comprises a plurality of antigens that comprise a plurality of immunogenic epitopes.

Embodiment 102. The method of embodiment 64-101, wherein none of the plurality of immunogenic epitopes decreases an immune response in the individual to any of the other immunogenic epitopes.

Embodiment 103. The method of any one of embodiments 64-102, wherein the antigen is a polypeptide and the immunogenic epitope is an immunogenic peptide epitope.

Embodiment 104. The method of embodiment 103, wherein the immunogenic peptide epitope is fused to an N-terminal flanking polypeptide and/or a C-terminal flanking polypeptide.

Embodiment 105. The modified T cell of embodiment 104, wherein the immunogenic peptide epitope fused to the N-terminal flanking polypeptide and/or the C-terminal flanking polypeptide is a non-naturally occurring sequence.

Embodiment 106. The method of embodiment 105, wherein the N-terminal and/or C-terminal flanking polypeptides are derived from an immunogenic synthetic long peptide (SLP).

Embodiment 107. The method of embodiment 105, wherein the N-terminal and/or C-terminal flanking polypeptides are derived from a disease-associated immunogenic SLP.

Embodiment 108. The method of embodiment 105, wherein the N-terminal flanking polypeptide comprises the amino acid sequence of any one of SEQ ID NOs: 5-10 and/or the C-terminal flanking polypeptide comprises the amino acid sequence of any one of SEQ ID NOs: 11-17.

Embodiment 109. The method of any one of embodiments 64-108, wherein the antigen is capable of being processed into an MHC class I-restricted peptide and/or an MHC class II-restricted peptide.

Embodiment 110. The method of any one of embodiments 64-109, wherein the modified T cell further comprises an agent that enhances the viability and/or function of the modified T cell as compared to a corresponding modified T cell that does not comprise the agent.

Embodiment 111. The modified T cell of embodiment 110, wherein the agent is a compound that enhances endocytosis, a stabilizing agent or a co-factor.

Embodiment 112. The modified T cell of embodiment 111, wherein the agent is albumin.

Embodiment 113. The modified T cell of embodiment 112, wherein the albumin is mouse, bovine, or human albumin.

Embodiment 114. The modified T cell of embodiment 110, wherein the agent is a divalent metal cation, glucose, ATP, potassium, glycerol, trehalose, D-sucrose, PEG1500, L-arginine, L-glutamine, or EDTA.

Embodiment 115. The method of any one of embodiments 64-114, wherein the modified T cell comprises a further modification to modulate MHC class I expression.

Embodiment 116. The method of any one of embodiments 64-115, wherein the modified T cell comprises a further modification to modulate MHC class II expression.

Embodiment 117. The method of embodiment 115, wherein an innate immune response mounted in the individual in response to administration, in an allogeneic context, of the modified T cells is reduced compared to an innate immune response mounted in an individual in response to administration, in an allogeneic context, of corresponding modified T cells that do not comprise the further modification.

Embodiment 118. The method of embodiment 115 or 117, wherein the circulating half-life of the modified T cells in an individual to which they were administered is increased compared to the circulating half-life of corresponding modified T cells that do not comprise the further modification in an individual to which they were administered.

Embodiment 119. The method of any one of embodiments 64-118, wherein the modified T cell includes one or more of helper T cells, cytotoxic T cells, memory T cells, or natural killer T cells.

Embodiment 120. The method of any one of embodiments 64-119, wherein the modified T cell includes one or more of CD3+ T cells, CD4+ T cells, CD8+ T cells, CD45RA+ T cells, CD45RO+ T cells, or γδ-T cells.

Embodiment 121. The method of any one of embodiments 64-120, wherein the modified T cell is allogeneic to the individual.

Embodiment 122. The method of any one of embodiments 64-121, wherein the modified T cell is autologous to the individual.

Embodiment 123. The method of any one of embodiments 64-122, wherein the individual is pre-conditioned to modulate inflammation and/or an immune response.

Embodiment 124. The method of any one of embodiments 64-123, further comprising administering to the individual a second adjuvant.

Embodiment 125. The method of embodiment 124, wherein the second adjuvant is IFN-α, LPS or a CpG ODN.

Embodiment 126. The method of embodiment 124 or 125, wherein the modified T cell and the second adjuvant are administered concurrently or simultaneously.

Embodiment 127. The method of embodiment 124 or 125, wherein the modified T cell and the second adjuvant are administered sequentially.

Embodiment 128. The method of embodiments 124-127, wherein the modified T cell is administered prior to administering the second adjuvant.

Embodiment 129. The method of embodiments 124-128, wherein the modified T cell is administered following administration of the second adjuvant.

Embodiment 130. The method of embodiments 64-129, wherein the modified T cell is administered prior to, concurrently with, or following administration of an immune checkpoint inhibitor.

Embodiment 131. The method of embodiment 130, wherein the immune checkpoint inhibitor is targeted to any one of PD-1, PD-L1, CTLA-4, TIM-3, LAG3, VISTA, TIM1, B7-H4 (VTCN1) or BTLA.

Embodiment 132. The method of embodiments 64-131, wherein the modified T cell is administered prior to, concurrently with, or following administration of a chemotherapy.

Embodiment 133. The method of embodiment 132, wherein the chemotherapy comprises cisplatin.

Embodiment 134. The method of any one of embodiments 64-133, wherein administration of the modified T cell to the individual results in activation and/or expansion of cytotoxic T lymphocytes (CTLs) specific for the antigen.

Embodiment 135. The method of any one of embodiments 64-134 wherein administration of the modified T cell to the individual results in activation and/or expansion of helper T (Th) cells specific for the antigen.

Embodiment 136. The method of any one of embodiments 64-135, wherein the amount of the modified T cell administered to the individual is between about $1\times10^6$ and about $1\times10^{12}$ cells.

Embodiment 137. The method of any one of embodiments 64-136, wherein the method comprises multiple administrations of the modified T cell.

Embodiment 138. The method of embodiment 137, wherein the time interval between two successive administrations of the modified T cell is between about 1 day and about 30 days.

Embodiment 139. A method for modulating an immune response in an individual, comprising: administering to the individual a modified T cell associated with an antigen, wherein the modified T cell is prepared by a process comprising the steps of: a) incubating an input T cell with an antigen and/or an adjuvant for a sufficient time to allow the antigen to associate with the cell surface of the input T cell, wherein the antigen comprises an immunogenic epitope, thereby generating a modified T cell associated with the antigen; and b) administering the modified T cell to the individual.

Embodiment 140. The method in embodiment 139, wherein the HPV antigen comprises an amino acid sequence with at least 90% similarity to any one of SEQ ID NOs:18-25.

Embodiment 141. The method in embodiment 140, wherein the HPV antigen comprises the amino acid sequence of SEQ ID NO:23.

Embodiment 142. The method in any one of embodiments 139-141, wherein the adjuvant is CpG ODN or LPS.

Embodiment 143. The method of embodiment 142, wherein the CpG ODN is CpG ODN 1018, CpG ODN 1826 or CpG ODN 2006.

Embodiment 144. A composition comprising the modified T cell of any one of embodiments 1-59 for use in a method of treatment of the human or animal body by surgery, therapy or diagnosis.

Embodiment 145. A composition comprising the modified T cell of any one of embodiments 1-59 for use in a method for modulating an immune response in an individual, the method comprising administering to the individual the modified T cell.

Embodiment 146. A composition comprising the modified T cell for use in a method of treatment of the human or animal body by surgery, therapy or diagnosis, wherein the modified T cell comprising an antigen comprising the amino acid sequence of any one of SEQ ID NOs: 18-25.

Embodiment 147. A composition comprising the modified T cell for use in a method of modulating an immune response in an individual, wherein the modified T cell comprising an antigen comprising the amino acid sequence of any one of SEQ ID NOs: 18-25.

Embodiment 148. A composition comprising the modified T cell for use in a method of treatment of the human or animal body by surgery, therapy or diagnosis, wherein the modified T cell is prepared by the method comprising: a) passing a cell suspension comprising an input T cell through a cell-deforming constriction, wherein a diameter of the constriction is a function of a diameter of the input T cell in the suspension, thereby causing perturbations of the input T cell large enough for an antigen and an adjuvant to pass through to form a perturbed input T cell, wherein the antigen comprises an immunogenic epitope; b) incubating the perturbed input T cell with the antigen and the adjuvant for a sufficient time to allow the antigen and the adjuvant to enter the perturbed input T cell, thereby generating a modified T cell comprising the antigen and adjuvant.

Embodiment 149. A composition comprising the modified T cell for use in a method of modulating an immune response in an individual, wherein the modified T cell is prepared by the method comprising: a) passing a cell suspension comprising an input T cell through a cell-deforming constriction, wherein a diameter of the constriction is a function of a diameter of the input T cell in the suspension, thereby causing perturbations of the input T cell large enough for an antigen and an adjuvant to pass through to form a perturbed input T cell, wherein the antigen comprises an immunogenic epitope; b) incubating the perturbed input T cell with the antigen and the adjuvant for a sufficient time to allow the antigen and the adjuvant to enter the perturbed input T cell, thereby generating a modified T cell comprising the antigen and adjuvant.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Example 1

In order to determine the minimum effective cell dose of $T_{APC}$s needed to lead to tumor growth inhibition in a therapeutic setting, four different doses of prime/boost $T_{APC}$s were tested in a TC1 tumor model, with the area of the tumors plotted against time.

C57BL/6J female mice were injected in the right rear flank with TC1 tumor cells (50k cells/mouse) at Day 0. On Days 4 (prime) and 7 (boost), T cells from C57BL/6J female donor mice were isolated and loaded using SQZ with 200 μg/mL CpG ODN 1826 and pre-complexed 40 μM E7 SLP (GQAEPDRAHYNIVTFSSKSDSTLRLSVQSTHVDIR; SEQ ID NO:25)+40 μM mouse serum albumin (MSA). Animals (10 mice/group) were injected intravenously with the relevant dose of E7+MSA+CpG loaded T cells (50M cells/mL) and TC-1 tumor growth was measured beginning 1 week post-tumor implantation two times per week and compared to tumor growth in untreated mice. A representative schematic of the treatment groups and schedule is outlined in FIG. 1A.

Figure 1B:
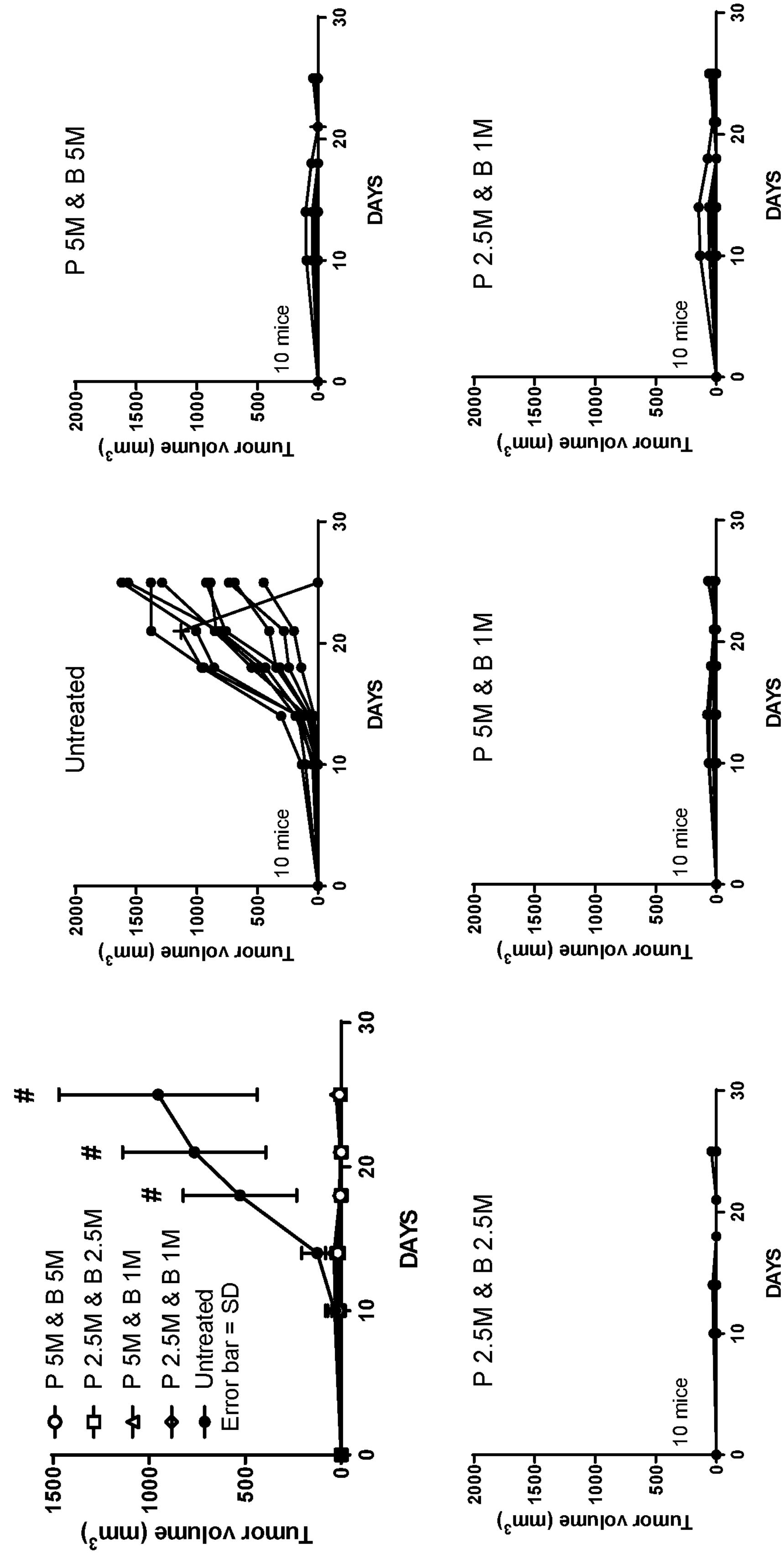
FIG. 1B shows tumor growth, as measured by the formula ((length×width$^2$)/2) compared between mice from the untreated group (no adoptive transfer of T cells) and the treatment groups B-E outlined in FIG. 1A.

Tumor growth, as measured by the formula ((length×width$^2$)/2), was compared between mice from the untreated group (no adoptive transfer of T cells) and the treatment groups B-E outlined in FIG. 1A is shown in FIG. 1B. All treatment conditions led to complete tumor reduction, indicative that the lowest cell dose tested (2.5M cells prime, 1M cells boost) was still capable of achieving the same tumor reduction as higher cell doses, each reaching statistical significance relative to untreated at Day 18 (#P<0.0001).

Example 2

To determine the E7 SLP design, two different E7 SLPs, the native E7 SLP and one in which the native sequence has all cysteines replaced with serine, were SQZ'd into T APCs along with CpG co-administration, and each condition was assessed for IFN-γ production by ICS.

Figure 2A:
FIG. 2A shows a representative schematic for evaluating E7 antigens.
Figure 2B:
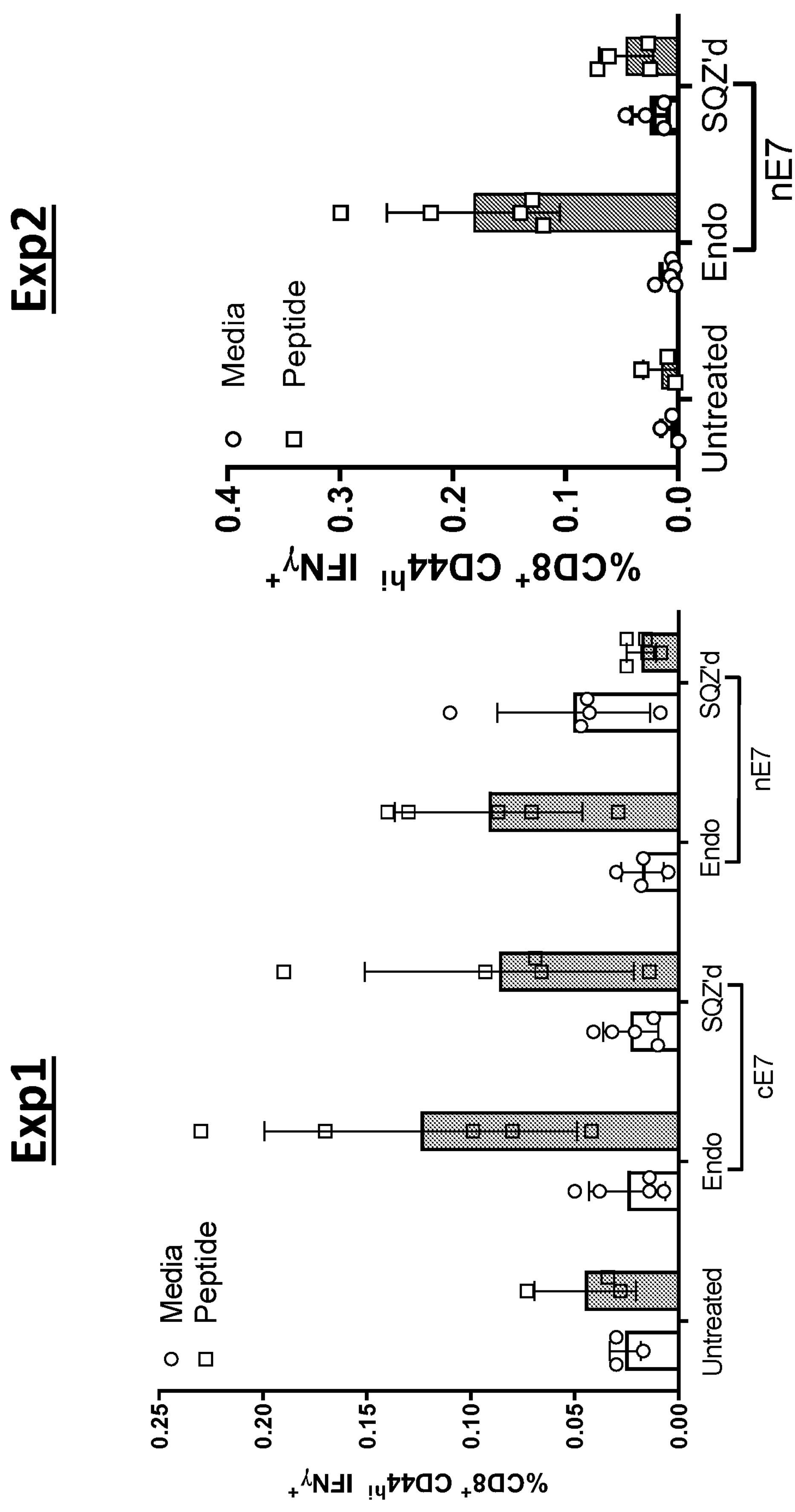
FIG. 2B shows that the impact of SLP sequence on IFN-γ-producing CD8+ T cells generated in response to $T_{APC}$ vaccination.

T cells from C57BL/6J female donor mice were isolated and loaded using SQZ with varying doses (Left—200 μg/mL, Right—25 μg/mL) CpG ODN 1826 and pre-complexed 40 μM E7 native or classic SLP+40 μM mouse serum albumin (MSA) or T cells were incubated with the same conditions in the absence of SQZ as a negative control (Endo—Groups B and D). Animals (5 mice/group) were injected intravenously with 5M loaded or incubated T cells in 100 μL volume (50M cells/mL). On Day 8, spleens were harvested and the % of IFN-γ-producing CD8+ T cells was quantified by ICS. A representative schematic of the treatment groups and schedule is outlined in FIG. 2A.

The % of IFN-γ-producing CD8+ T cells was highest in the Endo control group using cE7, which was not significantly different from SQZ with cE7 or Endo with nE7.

Unexpectedly, there was no benefit to SQZ vs. Endo, but there was a notable decrease in % of IFN-γ-producing CD8+ T cells in the SQZ nE7 condition relative to all others. This data shows that the SLP sequence has an impact on % of IFN-γ-producing CD8+ T cells generated in response to T APC vaccination, particularly when the antigen is loaded into the T cell using SQZ.

Example 3

To determine the ability of E6 SLPs to induce an antigens-specific immune response in E6 responder T cells in an in vitro human model, primary human T cells were loaded with an E6 SLP and responder cell IFN-γ secretion was measured by ELISA.

Human T cells were isolated from the PBMCs of HLA-A02+ donors (10M cells/mL) and 50 μM E6 SLP containing the HLA-A02-restricted minimal $E6_{29-38}$ epitope (LPQLSTELQTTIHDIILECVYSKQQLLRREVYDFAF; SEQ ID NO:18) was delivered intracellularly by SQZ and the level of IFN-γ, as measured by ELISA, was compared between the SQZ conditions and a control wherein the E6 SLP is incubated with the $T_{APC}$s in the absence of SQZing (Endo). $T_{APC}$s were then co-cultured with E6-specific CD8+ responder cells in a ratio of 1:1 stimulator:effector and cultured in the presence of IL-2 (100 U/mL). After 18h, supernatant is harvested from each condition and the level of IFN-γ production was assessed by IFN-γ ELISA (Biolegend).

Figure 3:
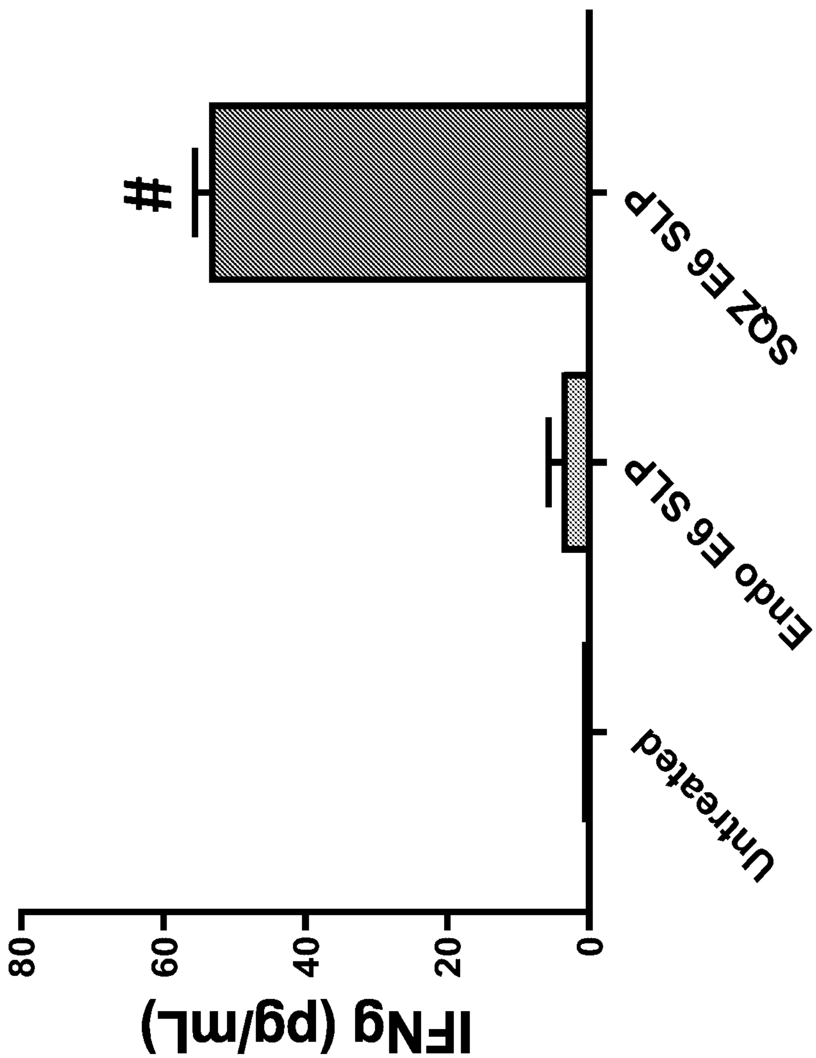
FIG. 3 is a graph showing the ability of E6 SLPs to induce an antigens-specific immune response in E6 responder T cells in an in vitro human model.

The E6 SLP tested, when delivered intracellularly using SQZ, led to a >10-fold increase in IFN-γ production when co-cultured with E6 responder CD8+ T cells (#P<0.0001) as shown in FIG. 3. These findings show the ability of T APCs to elicit an antigen-specific immune response to multiple HPV antigens (E6 and E7).

Example 4

To determine the ability of E7 SLPs to induce an antigen-specific immune response in $E7_{11-20}$ responder T cells, as well as the impact of SLP sequence on SQZ T cell APC ($T_{apc}$) activation in an in vitro human model, primary human T cells from multiple donors were loaded with different E7 SLPs and responder cell IFN-γ secretion was measured by ELISA.

Human T cells were isolated from the PBMCs of HLA-A02+ donors (10M cells/mL) and 50 μM OL-$E7_{1-35}$ (MHGDTPTLHEYMLDLQPETTDLYCYEQLNDSSEEE; SEQ ID NO:22) or E7.6 (QLCTELQTYMLDLQPETTYCKQQLL; SEQ ID NO:23) SLPs were delivered intracellularly by SQZ and the level of IFN-γ, as measured by ELISA, were compared between the SQZ conditions and a control wherein the E7 SLP were incubated with the $T_{apc}$s in the absence of SQZing (Endo). $T_{APC}$s were then co-cultured with $E7_{11-20}$-specific CD8+ responder cells in a ratio of 4:1 stimulator:effector and cultured in the presence of IL-2 (100 U/mL). After 24h, supernatant is harvested from each condition and the level of IFN-γ production was assessed by IFN-7 ELISA (Biolegend).

Figure 4:
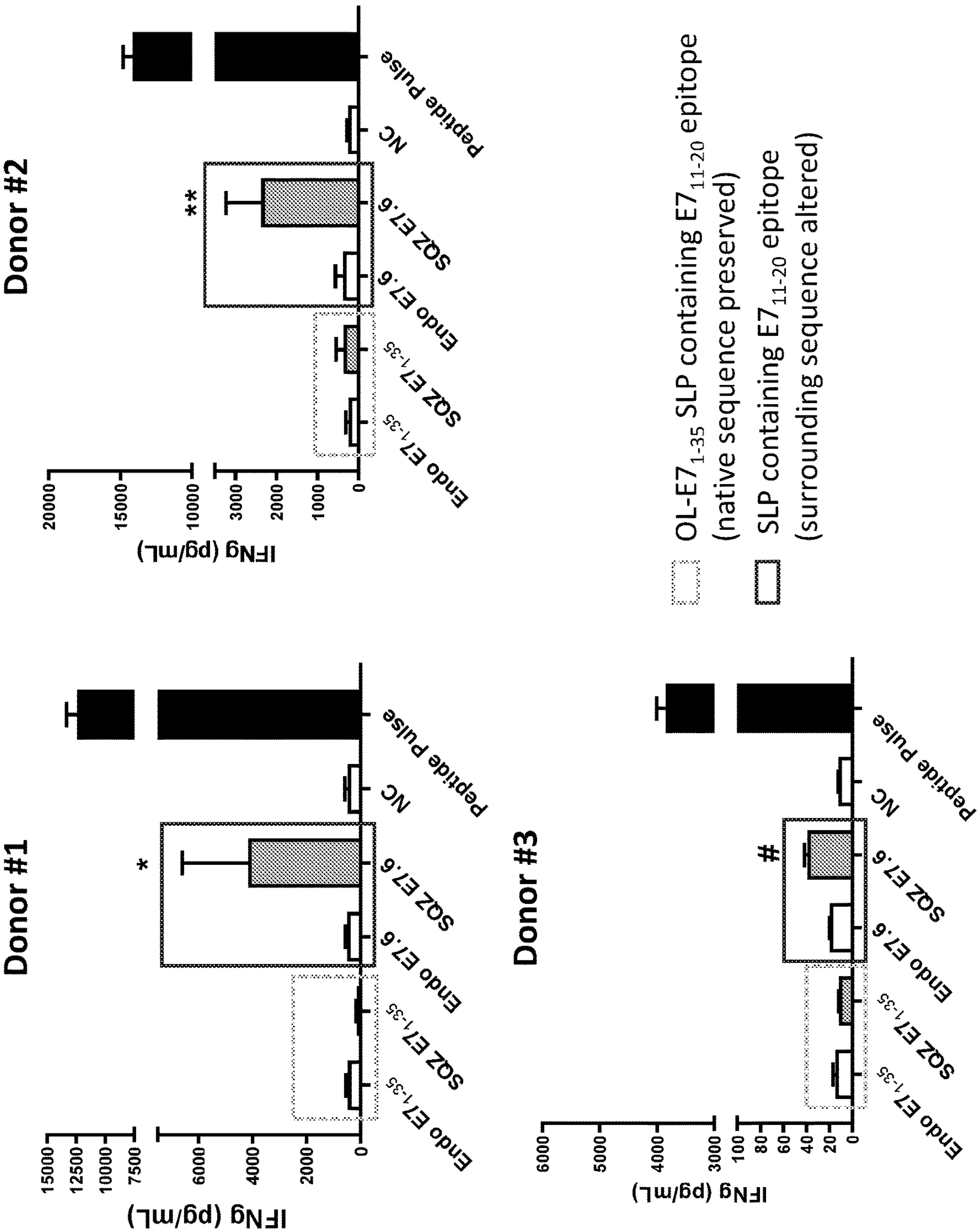
FIG. 4 shows the ability of E7 SLPs to induce an antigen-specific immune response in $E7_{11-20}$ responder T cells, as well as the impact of SLP sequence on SQZ T cell APC ($T_{apc}$) activation in an in vitro human model.

The native OL-$E7_{1-35}$ SLP elicited a minimal IFN-γ response when delivered using SQZ compared to Endo (FIG. 4). However, the E7.6, which comprises the E7 minimal epitope (YMLDLQPETT; SEQ ID NO:3) inserted in between the flanking regions of another reactive SLP ($E6_{21-45}$—QLCTELQTXXXXXXXXXXYCKQQLL), induced a greater IFN-γ response relative to the matched Endo control in all three donors tested when compared to the Endo controls (*P<0.05, **P<0.01; #P<0.0001). This finding highlights the importance of the flanking region sequence in the immunogenicity of the SLP and provides support that flanking regions of other SLPs, which are known to be reactive, can be used in conjunction with orthogonal minimal epitopes to achieve increased immune responses.

Example 5

To evaluate the dose of antigen for SQZ T cell APCs in an in vitro human model, primary human T cells were loaded with an E7 SLP at varying doses and assessed for IFN-γ by ELISA.

Human T cells were isolated from the PBMCs of HLA-A02+ donors (10M cells/mL) and varying doses (50 and 100 μM) E7 SLP (QLCTELQTYMLDLQPETTYCKQQLL; SEQ ID NO:23) were delivered intracellularly by SQZ and the level of IFN-γ, as measured by ELISA, were compared between the SQZ conditions and a control wherein the E7 SLP is incubated with the T APCs in the absence of SQZing (Endo). T APCs were then co-cultured with $E7_{11-20}$-specific CD8+ responder cells in a ratio of 4:1 stimulator:effector and cultured in the presence of IL-2 (100 U/mL). After 24h, supernatant is harvested from each condition and the level of IFN-γ production was assessed by IFN-γ ELISA (Biolegend). Additionally, a peptide pulse positive control was employed wherein B-LCL cells were incubated in the presence of the minimal E7 epitope (YMLDLQPETT; SEQ ID NO:3) for 1 h prior to ELISA.

Figure 5:
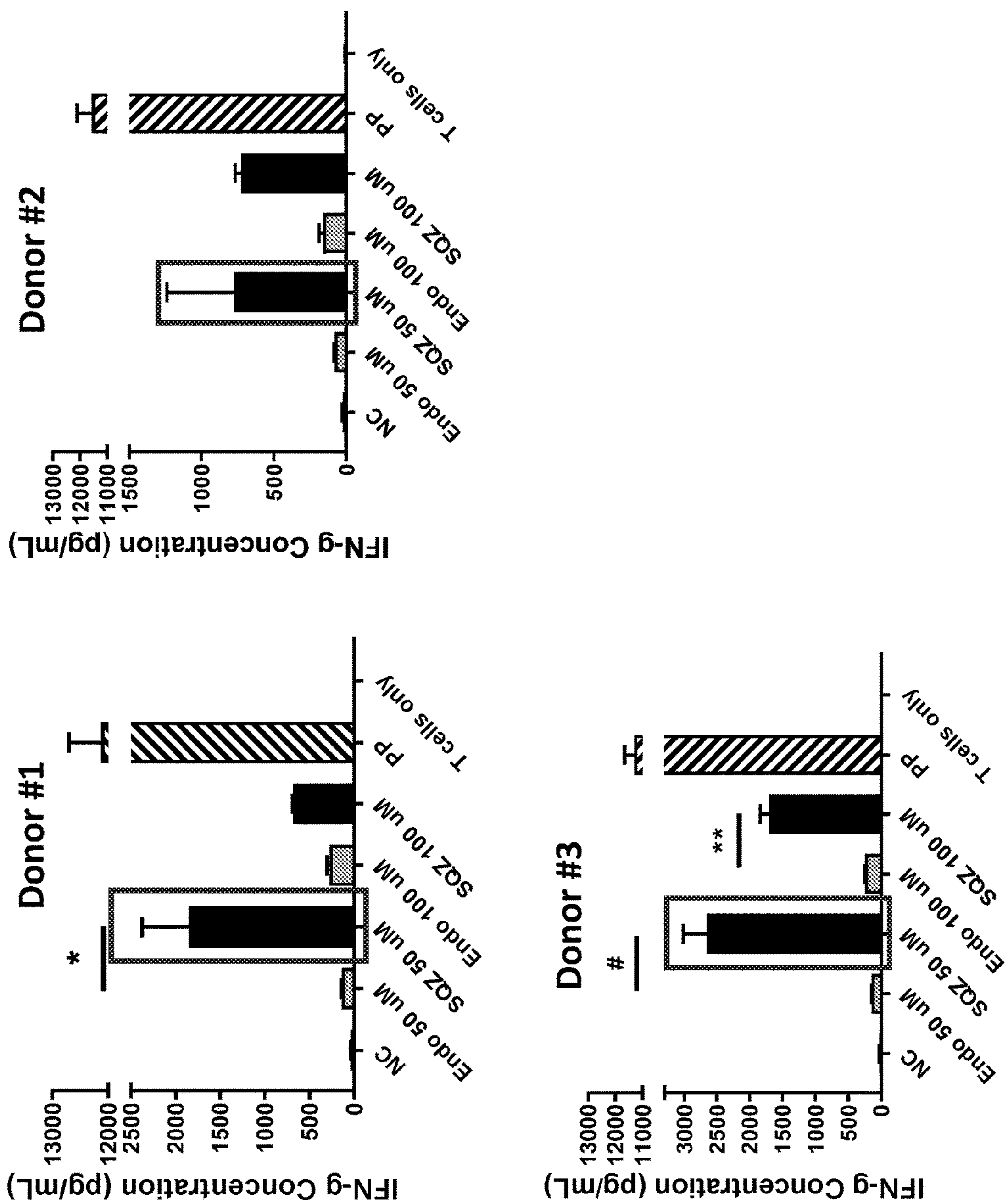
FIG. 5 shows results of a study to evaluate the dose of antigen for SQZ T cell APCs in an in vitro human model.

Across the three donors tested, consistent increases in IFN-γ occurs with all SQZ conditions relative to comparable control (Endo) where the SLP is incubated with the T cell in the absence of SQZ (FIG. 5). Donors 1 and 3 exhibited statistically significant increases with 50 μM E7 SLP (8668—*P<0.05; 8299—#P<0.0001), and a trend towards significance at the higher 100 μM E7 SLP. While there was no statistically significant difference between 50 and 100 μM for any donor, there was consistently equal or higher IFN-7 response with 50 μM E7 SLP.

Example 6

To determine the donor variability for SQZ T cell APCs in an in vitro human model, along with identify optimum combinations and doses of E6 and E7 SLPs that induce a significant immune response against E7 in primary human T cells from multiple HLA-A02+ donors were loaded with a E6 and E7 SLPs and assessed for IFN-γ by ELISA.

Human T cells were isolated from the PBMCs of HLA-A02+ donors (10M cells/mL) and 25 or 50 μM E6 SLP (QLCTELQTTIHDIILECVYCKQQLL; SEQ ID NO:19) and E7.6 SLP (QLCTELQTYMLDLQPETTYCKQQLL; SEQ ID NO:23) was delivered intracellularly by SQZ and the levels of IFN-γ, as measured by ELISA, were compared between the SQZ conditions and a control wherein the SLPs are incubated with the $T_{APC}$s in the absence of SQZing (Endo). A peptide pulse positive control was employed wherein B-LCL cells were incubated in the presence of the minimal E7 epitope (YMLDLQPETT; SEQ ID NO:3) at the same time as $T_{APC}$ generation. $T_{APC}$s and the positive control were then co-cultured with $E7_{11-20}$-specific CD8+ responder cells in a ratio of 4:1 stimulator:effector and cultured in the presence of IL-2 (100 U/mL). After 24h, supernatant is harvested from each condition and the level of IFN-γ production was assessed by IFN-γ ELISA (Biolegend).

Figure 6:
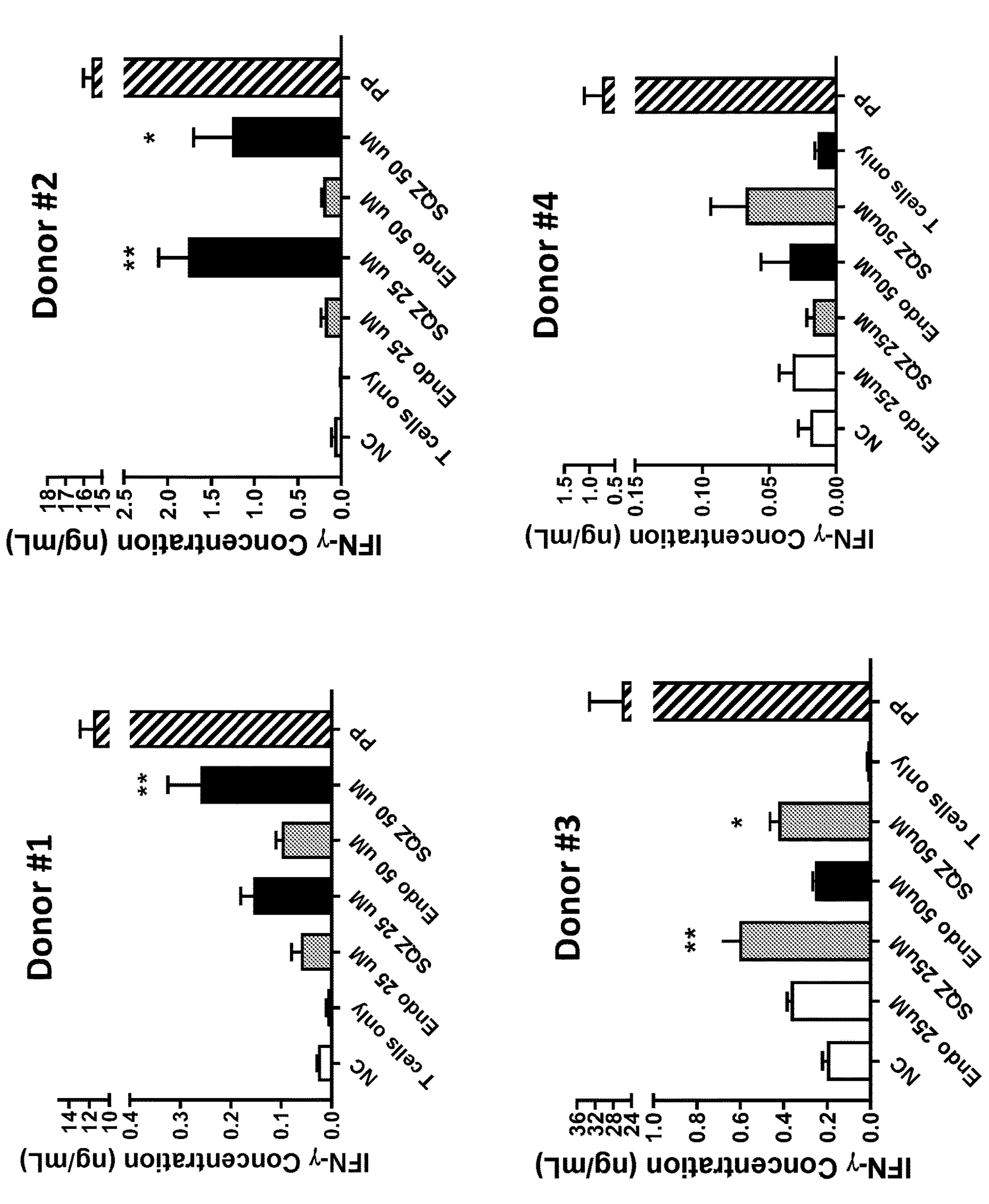
FIG. 6 shows the results of a study to determine the donor variability for SQZ T cell APCs in an in vitro human model.
Figure 6:
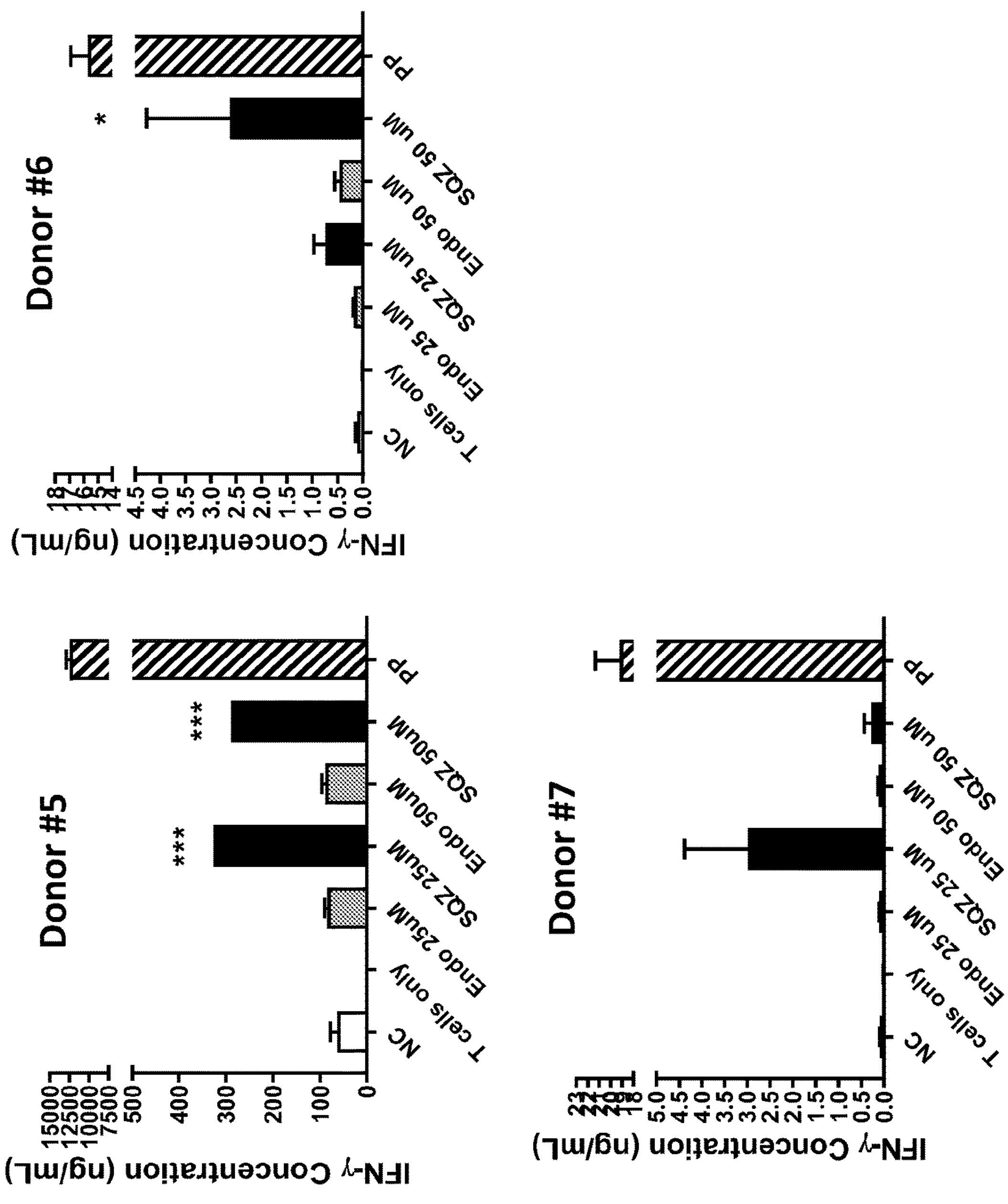

Five out of seven donors shown exhibited consistent increases in IFN-γ when treated with SQZ E6+E7 SLPs relative to comparable control (Endo) where the SLP is incubated with the T cell in the absence of SQZ (Donors 1-3, 5-6: *P<0.05, P<0.01, *P<0.005) as shown in FIG. 6. Of the two donors that did not have statistically significant increases when treated with SQZ'd T APCs relative to Endo controls, both donors (Donors 4 & 7) had conditions where there was detectable increases with one dose of SQZ'd T APCs tested (Donor 4-50 μM, Donor 7-25 μM), trending towards significance. Taken together, these data show that while different donor T APCs have differential immunostimulatory activity, we can see a consistent increase in IFN-γ production across multiple donors and that the E7-specific immune response is still significant when combined with multiple antigens/SLPs, in this case the HPV-specific E6 antigen.

Example 7

To help determine the adjuvant that leads to the most robust immune response, we tested the effect of two adjuvants that act on different pathways on the ability of the T APCs to induce an in vivo antigen-specific response. This effect was quantified by tetramer and ICS staining by flow cytometry.

Figure 7A:
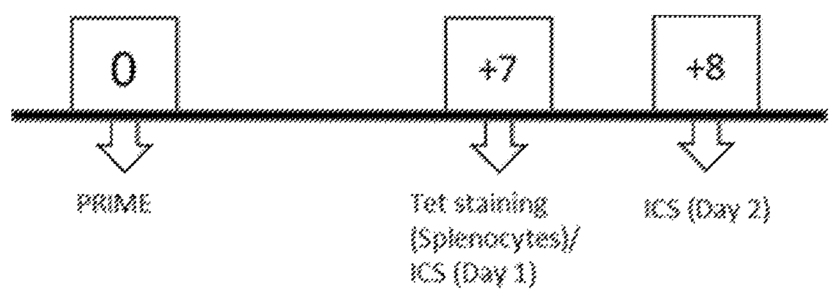
FIG. 7A is a schematic of an experiment to compare the robustness of immune responses using different adjuvants.

T cells from C57BL/6J female donor mice were isolated and loaded using SQZ with 400 μg/mL Ova+various concentrations of high- and low-molecular weight poly I:C (10, 30, 100, 300, 1000 μg/mL) and compared to T cells incubated with the same conditions in the absence of SQZ as a negative control (Endo—Groups C & E). T cells SQZ'd with Ova+200 μg/mL CpG were used as a positive control (Group F). On Day 0, mice (5/group, 3 untreated) were injected with 5M loaded or incubated T cells in 100 μL volume (50M cells/mL). On Day 7, spleens were harvested and Ova-specific T cells were quantified by tetramer staining using flow cytometry, while some splenocytes were permeabilized and fixed overnight. The next day (Day 8), the levels of IFN-γ was determined by ICS, with PMA/ionomycin acting as a positive control. A representative schematic of the treatment groups and schedule is outlined in FIG. 7A.

Figure 7B:
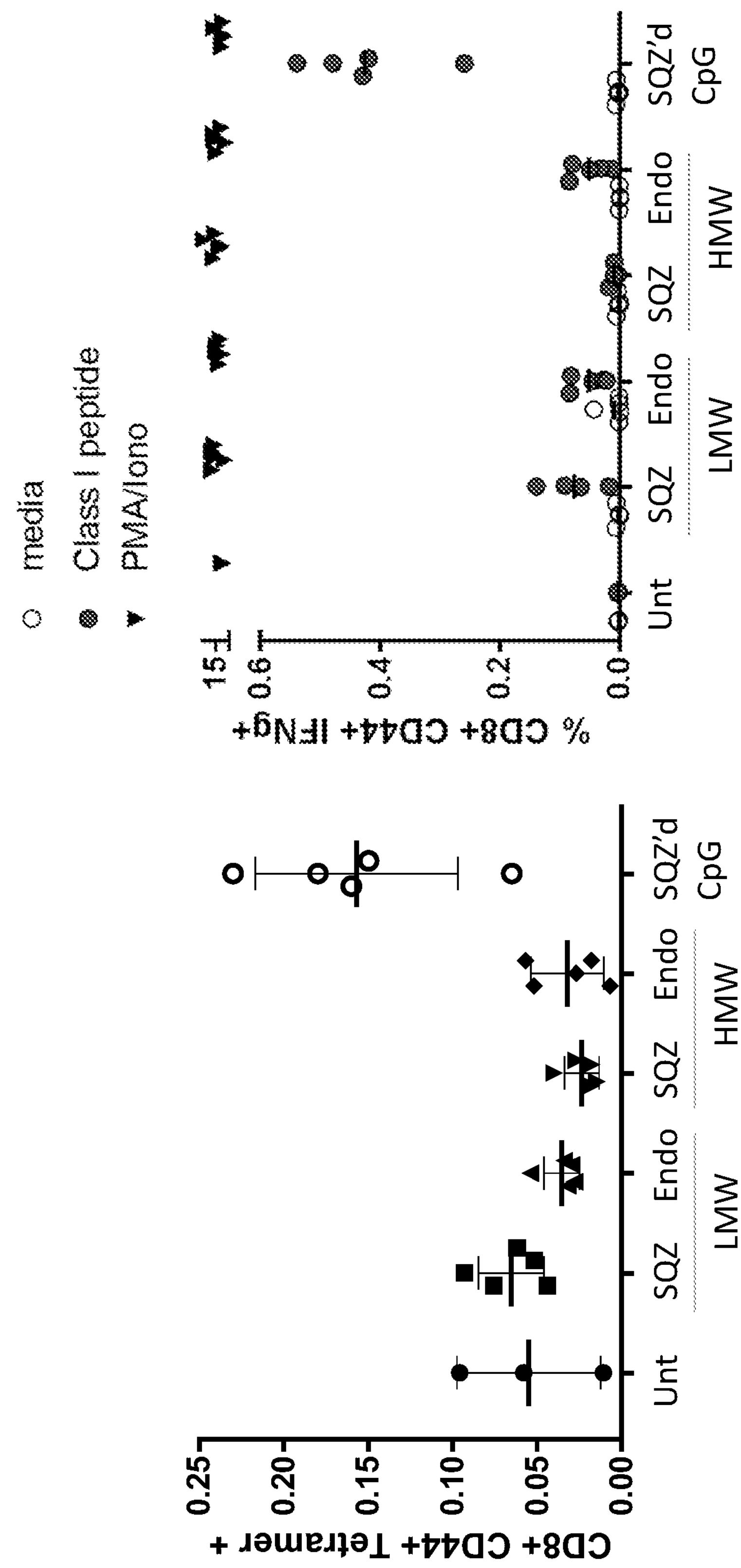
FIG. 7B shows the results of the experiment to compare robustness of immune responses using poly I:C and a CpG ODN.

The % of tetramer or IFN-γ-producing CD8+ T cells was highest in the group adjuvanted with CpG, while all conditions adjuvanted with LMW or HMVW poly I:C did not increase the percentage of Ova-specific or IFN γ-producing CD8+ T cells over untreated (FIG. 7B). As poly I:C is a TLR3 agonist, and CpG is a TLR9 agonist, this data supports the superiority of CpG over poly I:C as an adjuvant with T APC vaccination, while suggesting that TLR3 activation may not be beneficial in this setting.

Example 8

To help determine the concentration of CpG adjuvant that leads to the most robust immune response, we tested the effect of multiple doses of CpG on the ability of the T APCs to induce an in vivo antigen-specific response. This effect was quantified by tetramer and ICS staining by flow cytometry.

Figure 8A:
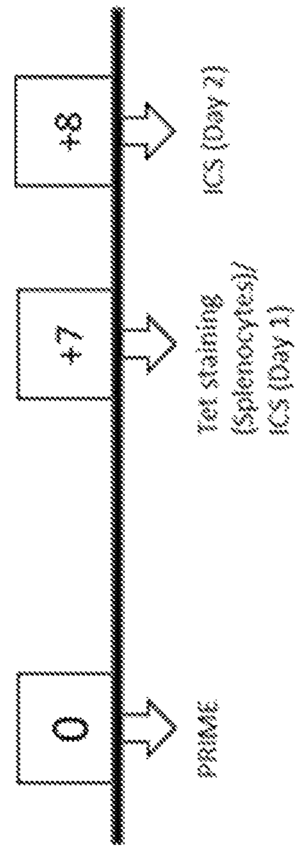
FIG. 8A is a schematic of an experiment evaluating the effect of concentration of CpG ODN on immune responses.

T cells from C57BL/6J female donor mice were isolated and loaded using SQZ with 400 μg/mL Ova+various concentrations of CpG 1826 (50, 100, 200 μg/mL) and compared to T cells incubated with the same conditions in the absence of SQZ as a negative control (Endo—Groups B, D & F). On Day 0, mice (5/group, 3 untreated) were injected with 5M loaded or incubated T cells in 100 μL volume (50M cells/mL). On Day 7, spleens were harvested and Ova-specific T cells were quantified by tetramer staining using flow cytometry, while some splenocytes were permeabilized and fixed overnight. The next day (Day 8), the levels of IFN-7 was determined by ICS, with PMA/ionomycin acting as a positive control. A representative schematic of the treatment groups and schedule is outlined in FIG. 8A.

Figure 8B:
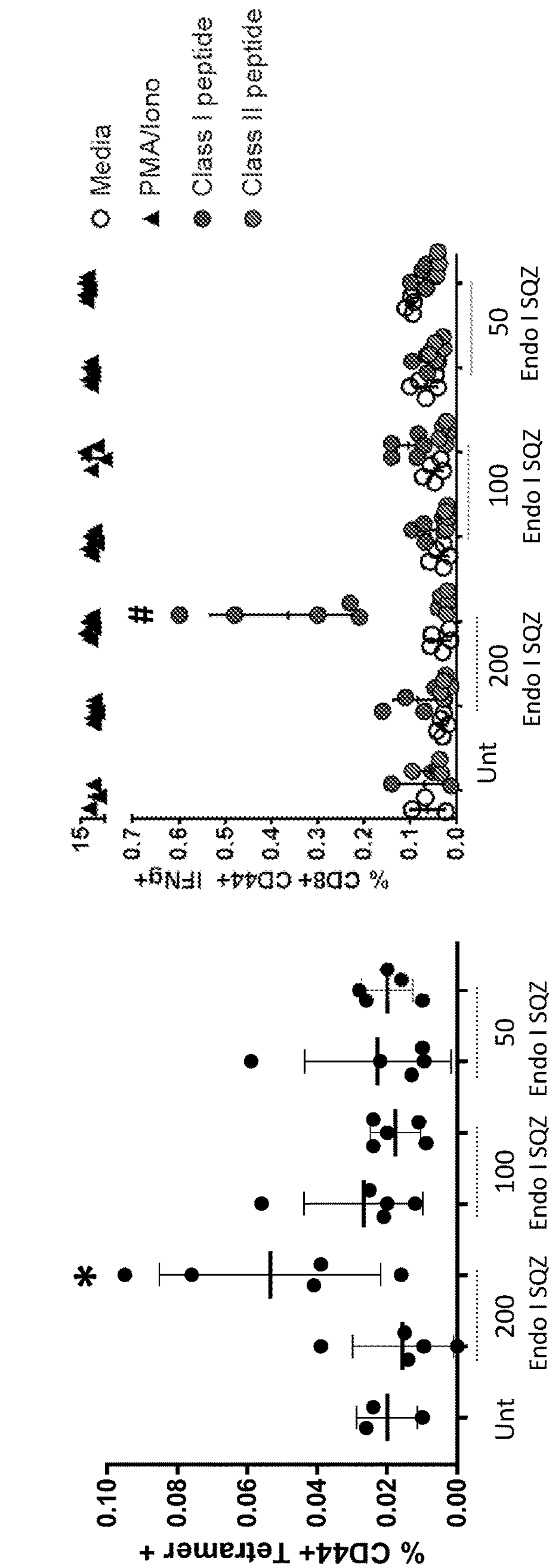
FIG. 8B shows the results of the experiment evaluating the effect of concentration of CpG ODN on immune responses.

The % of tetramer or IFN-γ-producing CD8+ T cells was highest in the group with 200 μg/mL CpG and was significantly different from the related Endo control (*P<0.05 for tetramer, #P<0.0001 for IFN-γ) for Class I peptide/MHC-I, while all other conditions did not elicit a significant response over untreated or their respective Endo controls (FIG. 8B). The activation of Ova-specific T cells was only observed with the Class I peptide, supporting the direct presentation of Ova antigens to effect a CD8+ T cell response.

Example 9

To help evaluate schedule for CpG adjuvant administration that leads to a robust immune response, we tested the effect of multiple dosing schedules of CpG on the ability of the T APCs to induce an in vivo antigen-specific response. This effect was quantified by tetramer and ICS staining by flow cytometry.

Figure 9A:
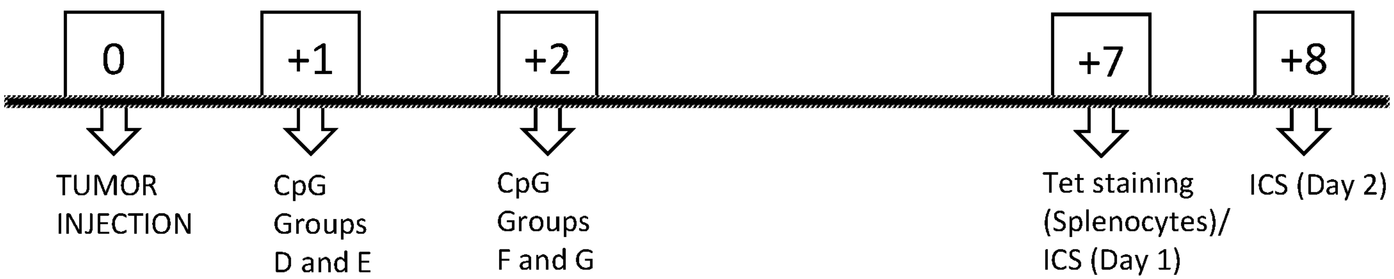
FIG. 9A is a schematic of an experiment evaluating the dosing schedule of CpG ODN on immune responses.

T cells from C57BL/6J female donor mice were isolated and loaded using SQZ with 400 μg/mL Ova and mice (5/group, 3 untreated) were injected with 5M loaded or incubated T cells in 100 μL volume (50M cells/mL). CpG 1826 (25 μg/mL) systemic co-administration of donor mice occurred either at the same time as the T APC prime (Day 0), or 1 or 2 days following prime (Day 1 or 2, respectively) and compared to T cells incubated with the same conditions in the absence of SQZ as a negative control (Groups B, D & F). T cells SQZ'd with (Ova+200 μg/mL CpG) were used as a positive control (Group H). On Day 7, spleens were harvested and Ova-specific T cells were quantified by tetramer staining using flow cytometry, while some splenocytes were permeabilized and fixed overnight. The next day (Day 8), the levels of IFN-γ was determined by ICS, with PMA/ionomycin acting as a positive control. A representative schematic of the treatment groups and schedule is outlined in FIG. 9A.

Figure 9B:
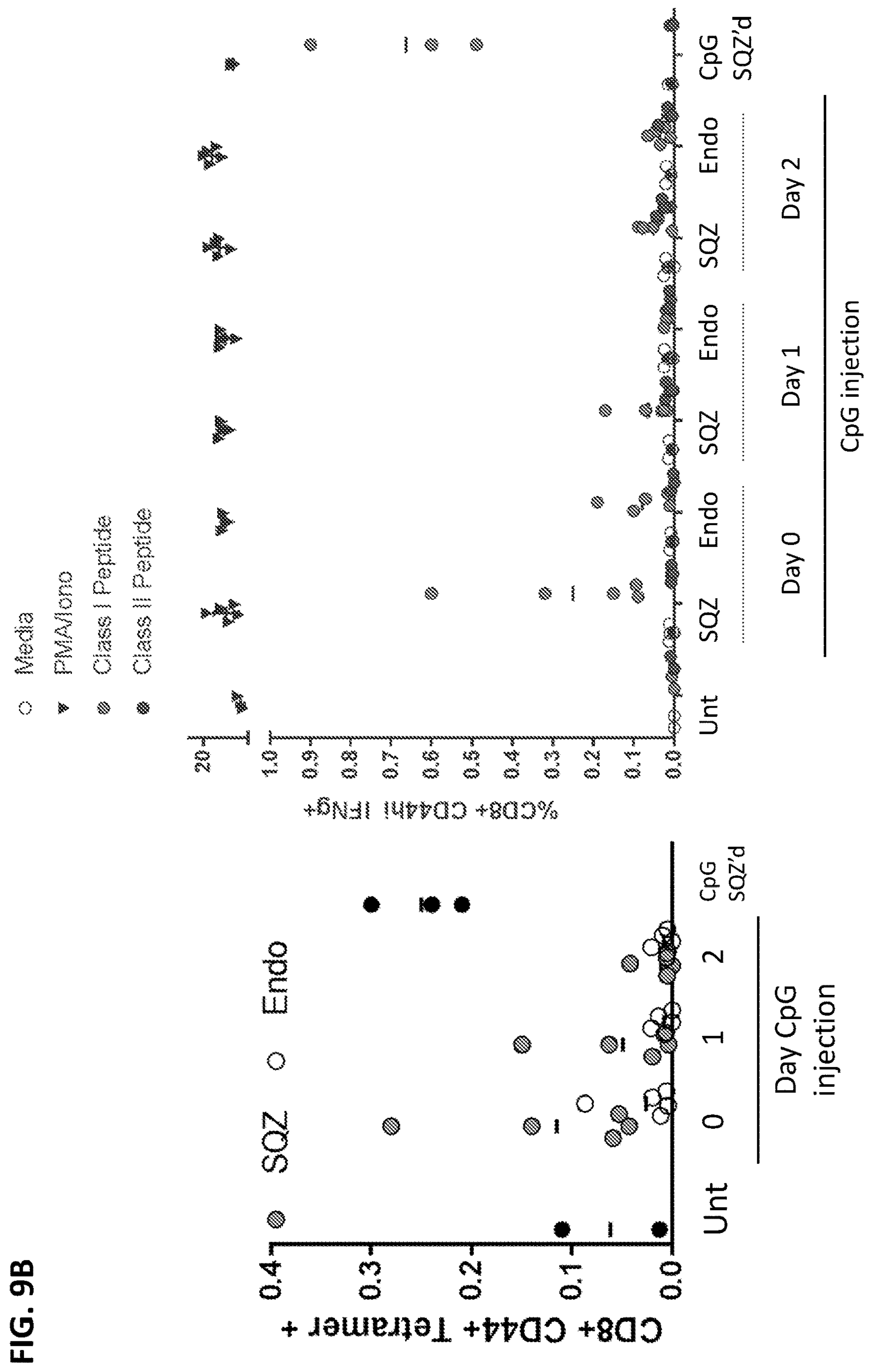
FIG. 9B shows the results of the experiment evaluating the dosing schedule of CpG ODN on immune responses.

The % of tetramer or IFN-γ-producing CD8+ T cells was highest in the group where Ova and CpG were co-delivered to T APCs, while co-administration the same day as prime (Group B) was the only co-administered CpG group to show some level of Ova-specific activation, trending towards significance (FIG. 9B). However, this data supports the observation that antigen+CpG co-delivery can lead to the greatest activation of Ova-specific CD8+ T cells, while delaying systemic administration of CpG leads to lower responses compared to simultaneous prime and co-administration of adjuvant.

Example 10

In order to determine a combination of intracellular and system adjuvant administration for T APC antitumor function, multiple routes of administration of CpG vs. IFN-α were compared in conjunction with our E7-specific T APC in a prophylactic TC-1 murine tumor model. Antigen-specific T cell responses were measured by tetramer staining and flow cytometry, while antitumor effect was measured by tumor growth prevention.

Figure 10A:
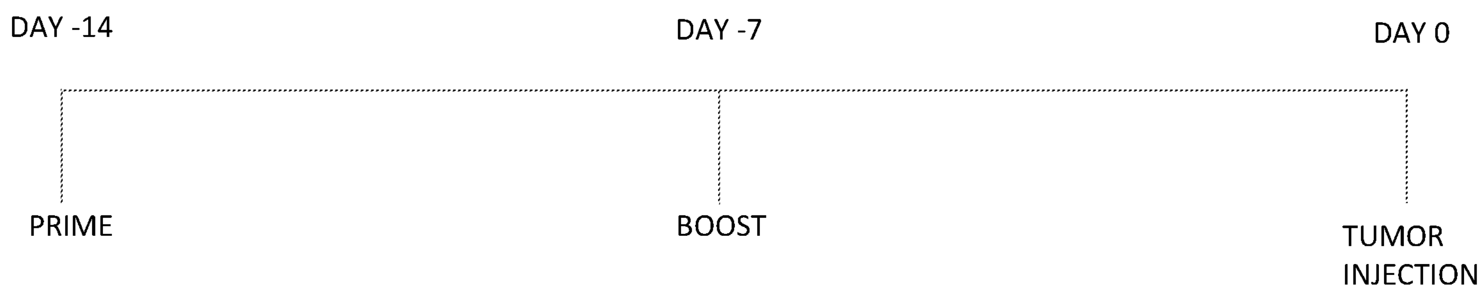
FIG. 10A is a schematic of an experiment to evaluate the combination of intracellular and systemic adjuvant administration for $T_{APC}$ antitumor function.

On Days −14 (prime) and −7 (boost), T cells from C57BL/6J female donor mice were isolated and loaded using SQZ with pre-complexed 40 μM E7 SLP (GQAEPDRAHYNIVTFSSKSDSTLRLSVQSTHVDIR; SEQ ID NO:25)+40 μM mouse serum albumin (MSA) (Groups B and C) or E7 SLP+MSA+200 μg/mL CpG ODN 1826 (Groups D, E and F). C57BL/6J female recipient mice (10 mice/group) were injected intravenously with 100 μL of loaded T cells (5M cells/animal), while groups B and E animals also received intravenous CpG (25 μg) and groups C and F received IV IFN-α (10k IU). On Days −8 and −3, 100 μL of murine blood was collected and the % of E7-specific CD8+ T cells was quantified by tetramer staining and flow cytometry. On Day 0, recipient mice were injected in the right rear flank with TC1 tumor cells (100k cells/mouse) and TC-1 tumor growth was measured two times per week beginning on Day 11 and compared to tumor growth in untreated mice. A representative schematic of the treatment groups and schedule is outlined in FIG. 10A.

Figure 10B:
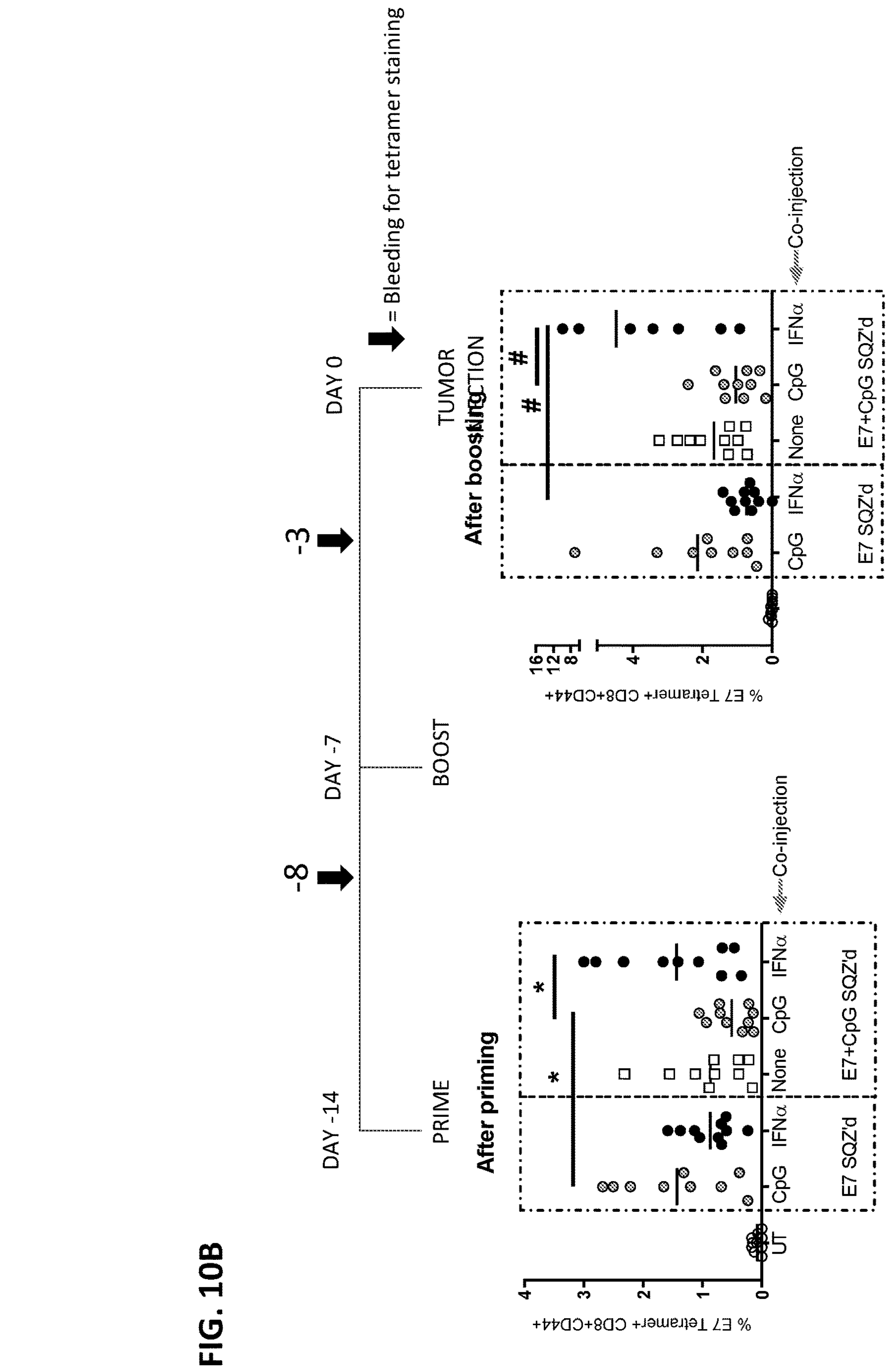
FIG. 10B shows T cell responses for each experimental group and FIG. 10C shows growth of tumors for each experimental group.
Figure 10C:
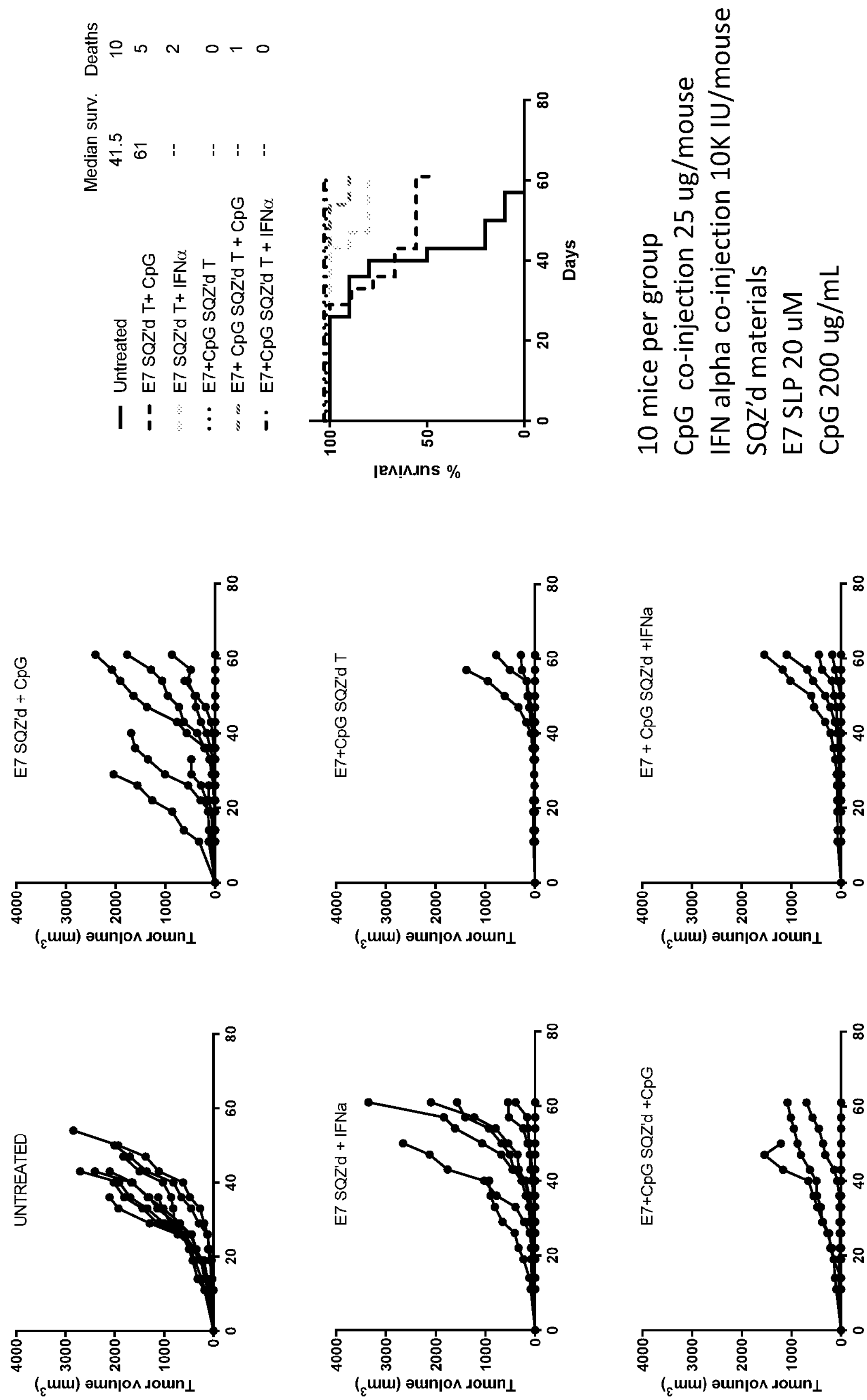
Figure 10D:
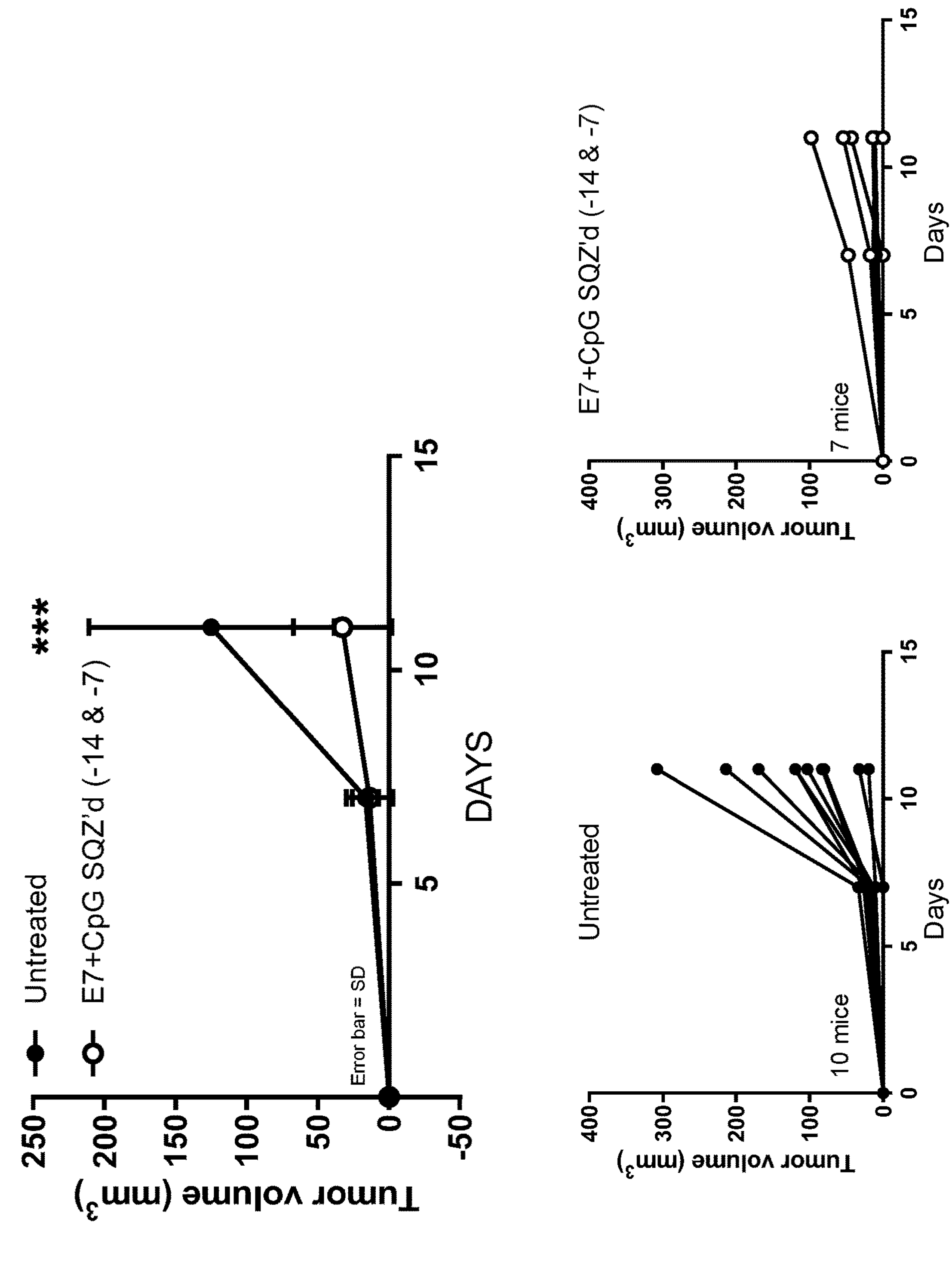
FIG. 10D shows tumor growth following rechallenge in animals treated with SQZ (E7+CpG) relative to untreated animals.

The percentage of E7-specific T cell were measured in mice by E7 tetramer staining after prime (Day −8) and boost (Day −3) with E7+MSA or E7+MSA+CpG SQZ'd T cells+/−co-administration of CpG or IFN-α (FIG. 10B). The highest relative proportion of E7-specific T cells were observed in the SQZ E7+CpG co-administration and SQZ (E7+CpG)+IFN-α co-administration groups. The relative number of E7-specific post-prime CD8+ T cells was surprisingly lower in the SQZ (E7+CpG)+co-administration of CpG relative to the SQZ E7+co-administration of CpG (*P<0.05), whereas the co-administration of IFN-α with SQZ (E7+CpG) T cells led to a significantly higher number of E7-specific T cells than co-administration of CpG with SQZ (E7+CpG) T cells (*P<0.05). After boost (Day −3), a similar trend was observed where SQZ E7+CpG co-administration and SQZ (E7+CpG)+IFN-α co-administration groups led to the highest % E7-specific T cells. However, the highest response came from the SQZ (E7+CpG)+IFN-α co-administration group, which was significantly higher than SQZ E7+IFN-α co-administration and SQZ (E7+CpG)+co-administration of CpG, showing that IFN-α co-administration leads to a higher percentage of antigen-specific T cells when used in combination with SQZ (E7+CpG) T cells. Tumor growth, as measured by the formula ((length×width$^2$)/2), was compared between mice from the untreated group (no adoptive transfer of T cells) and the treatment groups B-F outlined in FIG. 10C. The high tumor growth reduction and survival advantage of the SQZ (E7+CpG)+IFN-α co-administration group corresponds well with the tetramer staining, showing that the highest induction of E7-specific T cells led to the best antitumor activity. Interestingly, despite the low % of E7-specific T cells in the SQZ (E7+CpG) group, this treatment also afforded a very high level of antitumor activity, with this being the only other group (in addition to SQZ (E7+CpG)+IFN-α co-administration) that extended survival of all of the mice past 60 days. While slightly lower than the previously mentioned Groups D and F, there was a discernable survival extension and tumor growth inhibition in Groups C and E. On Day 78, the 7 tumor free mice from Group D were rechallenged with 50k cells to the opposite (left) flank and compared to age-matched untreated animals (10 mice) (FIG. 10D). Mice from Group D had a significant reduction in tumor growth after re-challenge, compared to untreated mice that have received their first challenge (***P<0.005), providing support that this antitumor effect is durable past 2 months.

Example 11

In order to determine the effect of combining multiple HPV antigens for T APC antitumor function, E6 and E7 synthetic long peptides (SLPs) alone and in combination in with our E7-specific T APCs in a prophylactic TC-1 murine tumor model. E7-specific T cell responses were measured by tetramer staining and flow cytometry, while antitumor effect was measured by tumor growth prevention.

Figure 11A:
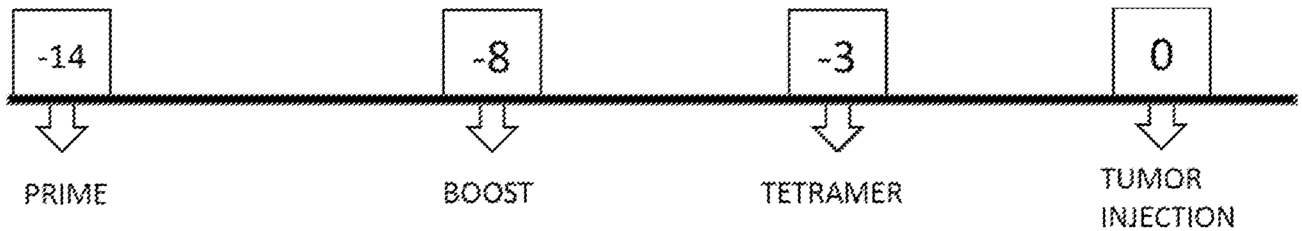
FIG. 11A is a schematic of an experiment to evaluate the effect of combining multiple HPV antigens for $T_{APC}$ antitumor function.

On Days −14 (prime) and −8 (boost), T cells from C57BL/6J female donor mice were isolated and loaded using SQZ with pre-complexed 20 μM mouse serum albumin (MSA)+20 μM E6 (VYSKQQLLRREVYDFAFRDLSIVYRDGNPYAVSDK; SEQ ID NO:21) and/or E7 SLP (GQAEPDRAHYNIVTFSSKSDSTLRLSVQSTHVDIR; SEQ ID NO:25) or the combination of both +/−200 μg/mL CpG ODN 1826 according to Table XX. T cells incubated with the same conditions as Group B in the absence of SQZ were used as a negative control (Group C). C57BL/6J female recipient mice (5-10 mice/group) were injected intravenously with 100 μL of loaded T cells (5M cells/animal). On Day −3, 100 μL of murine blood was collected and the % of E7-specific CD8+ T cells was quantified by tetramer staining and flow cytometry. On Day 0, recipient mice were injected in the right rear flank with TC1 tumor cells (100k cells/mouse) and TC-1 tumor growth was measured two times per week beginning on Day 11 and compared to tumor growth in untreated mice. A representative schematic of the treatment groups and schedule is outlined in FIG. 11A.

Figure 11B:
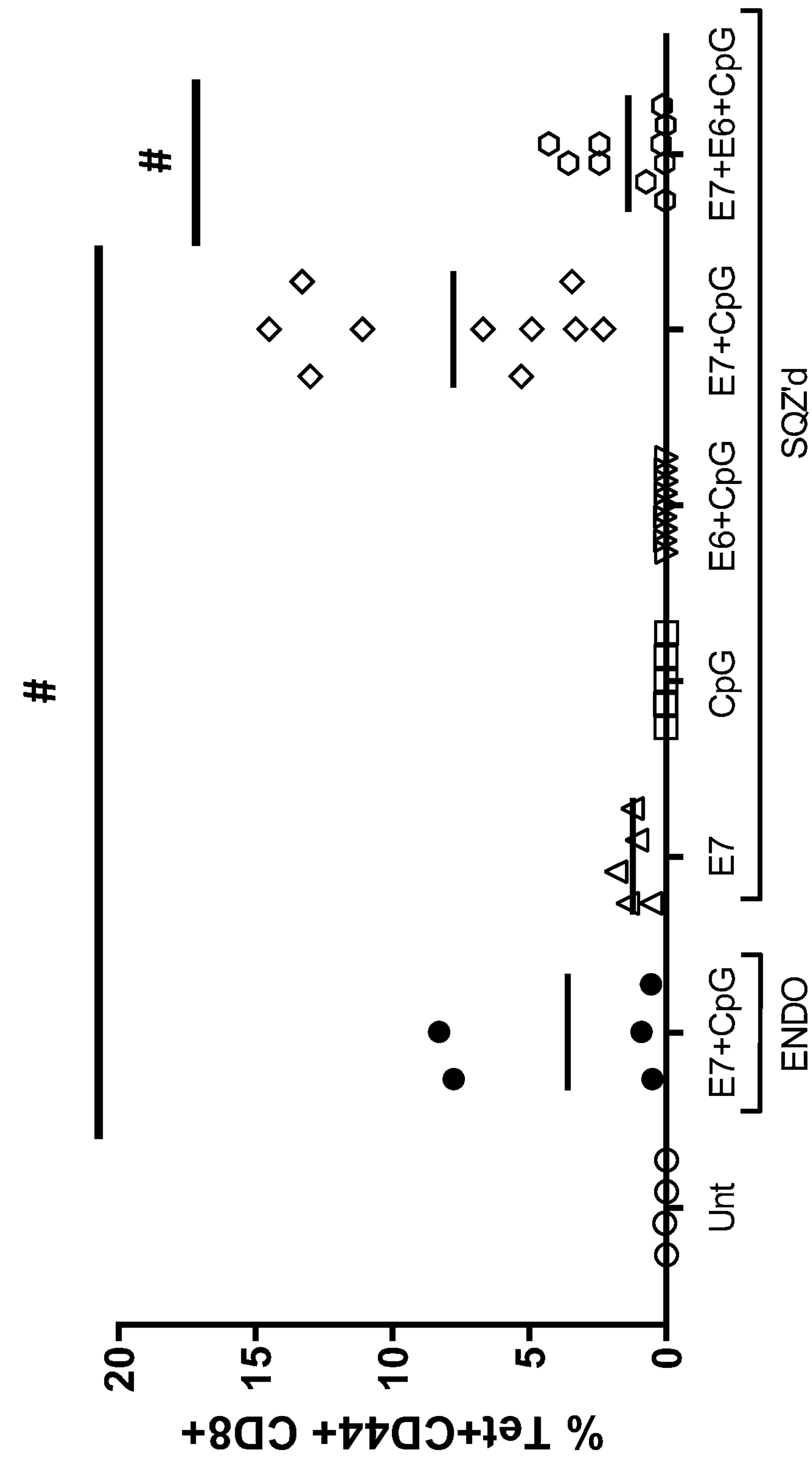
FIG. 11B shows T cell responses for each experimental group and FIG. 11C shows growth of tumors for each experimental group.
Figure 11C:
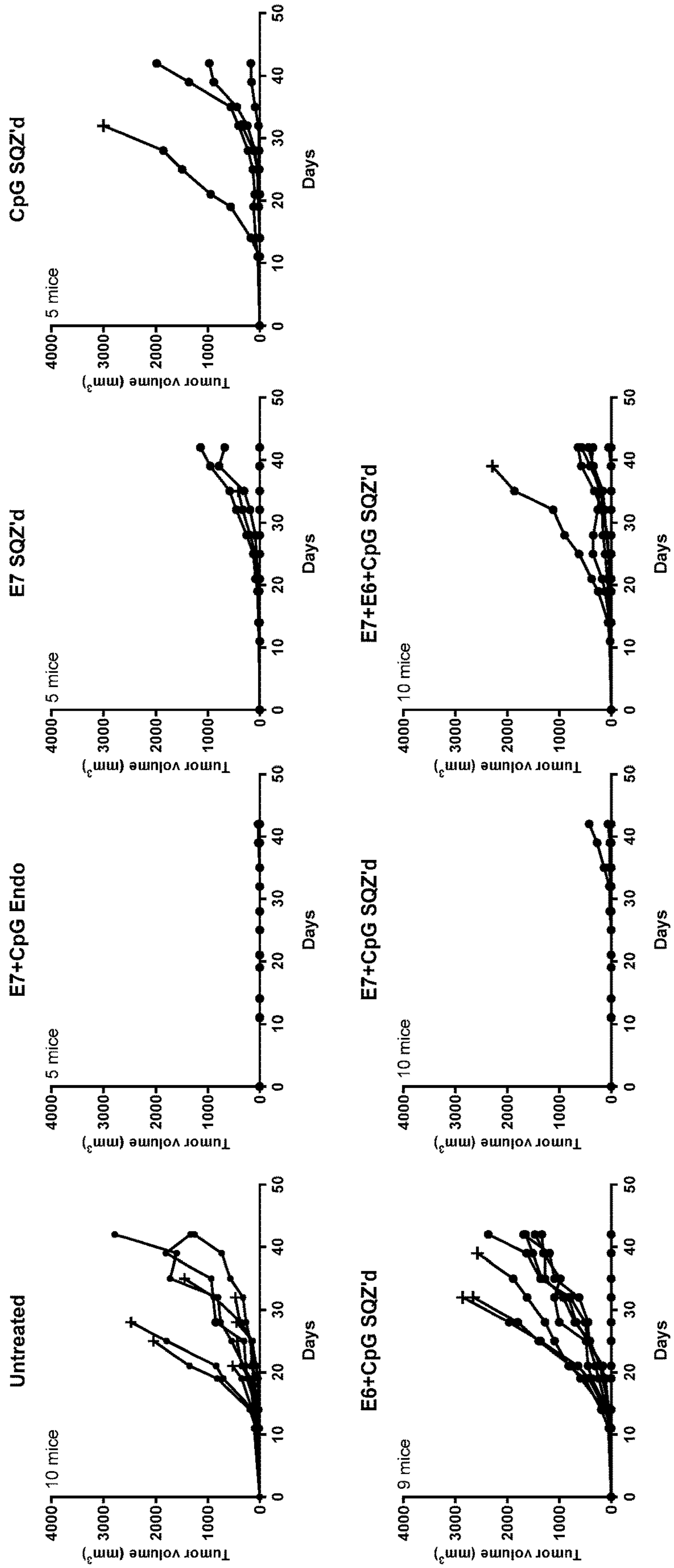

The percentage of E7-specific T cell were measured in mice by E7 tetramer staining after boost (Day −3) with the greatest effect observed with the CpG+E7 SQZ T APCs (Group B) as shown in FIG. 11B. Interestingly, Group B responses were significantly higher than untreated and the combination of E7 and E6 (Group F—#P<0.0001), providing evidence that the addition of the E6 SLP blunts the E7-specific response. Group B was significantly different from the other treatment groups, with the notable exception of the Endo control (Group C), wherein Group B was notably higher and trending towards statistical significance. As shown in FIG. 11C, tumor growth, as measured by the formula ((length×width$^2$)/2), was compared between mice from the untreated group (no adoptive transfer of T cells) and the treatment groups B-G outlined in FIG. 11A. High tumor growth prevention occurred in groups with T cells SQZ'd with E7+CpG, as well as T cells that were incubated in the presence of E7+CpG in the absence of SQZ. Groups D-F showed some level of tumor growth inhibition relative to untreated (Group A) and E6+CpG SQZ'd T cells (Group G), but were all less effective than Groups B and C.

Example 12

In order to determine the importance of the route of administration of CpG adjuvant for the E7-specific T APC antitumor effect, an E7 SLP was delivered to T cells in combination with CpG, either delivered to the T cell or systemically co-administered to the recipient animal and the antitumor effect was measured by tumor growth inhibition.

Figure 12A:
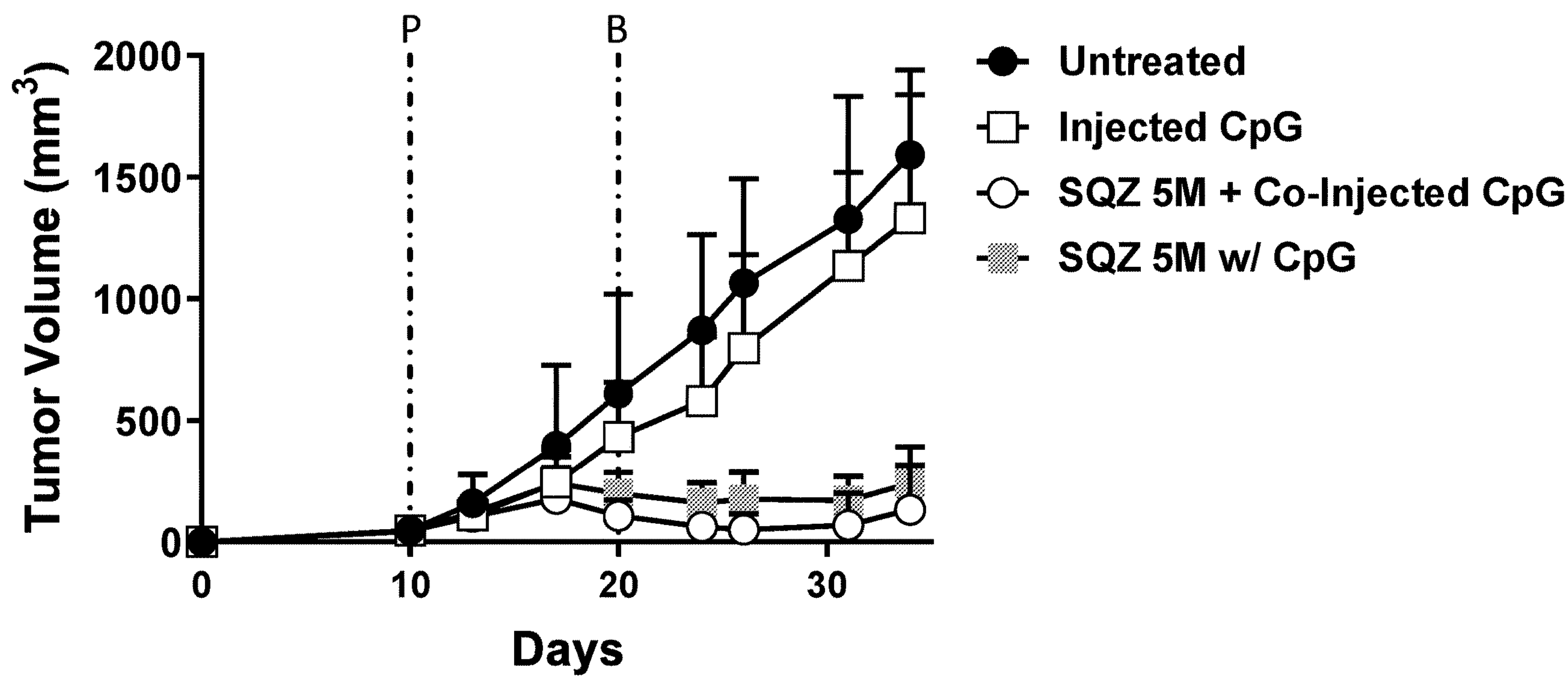
FIG. 12A shows the results of an experiment evaluating the importance of the route of administration of CpG adjuvant for the E7-specific $T_{APC}$ antitumor effect. The dosing schedule is provided.

On Day 0, recipient mice were injected in the right rear flank with TC1 tumor cells (50k cells/mouse). On Days 10 (prime) and 20 (boost), T cells from C57BL/6J female donor mice were isolated and loaded using SQZ with pre-complexed 20 μM mouse serum albumin (MSA)+20 μM E7 (GQAEPDRAHYNIVTFSSKSDSTLRLSVQSTHVDIR; SEQ ID NO:25) and ODN 1826 was either co-delivered (Group D) by SQZ at 200 μg/mL or co-administered to the animals systemically at 25 μg/mouse (Group C) and compared to untreated (Group A) and systemic administration of CpG alone (Group B). Recipient mice (8-10 mice/group) were treated with 100 μL of loaded T cells (5M cells/ animal). TC-1 tumor growth was measured two times per week beginning on Day 10. A representative schematic of the treatment groups and schedule is outlined in FIG. 12A.

Figure 12B:
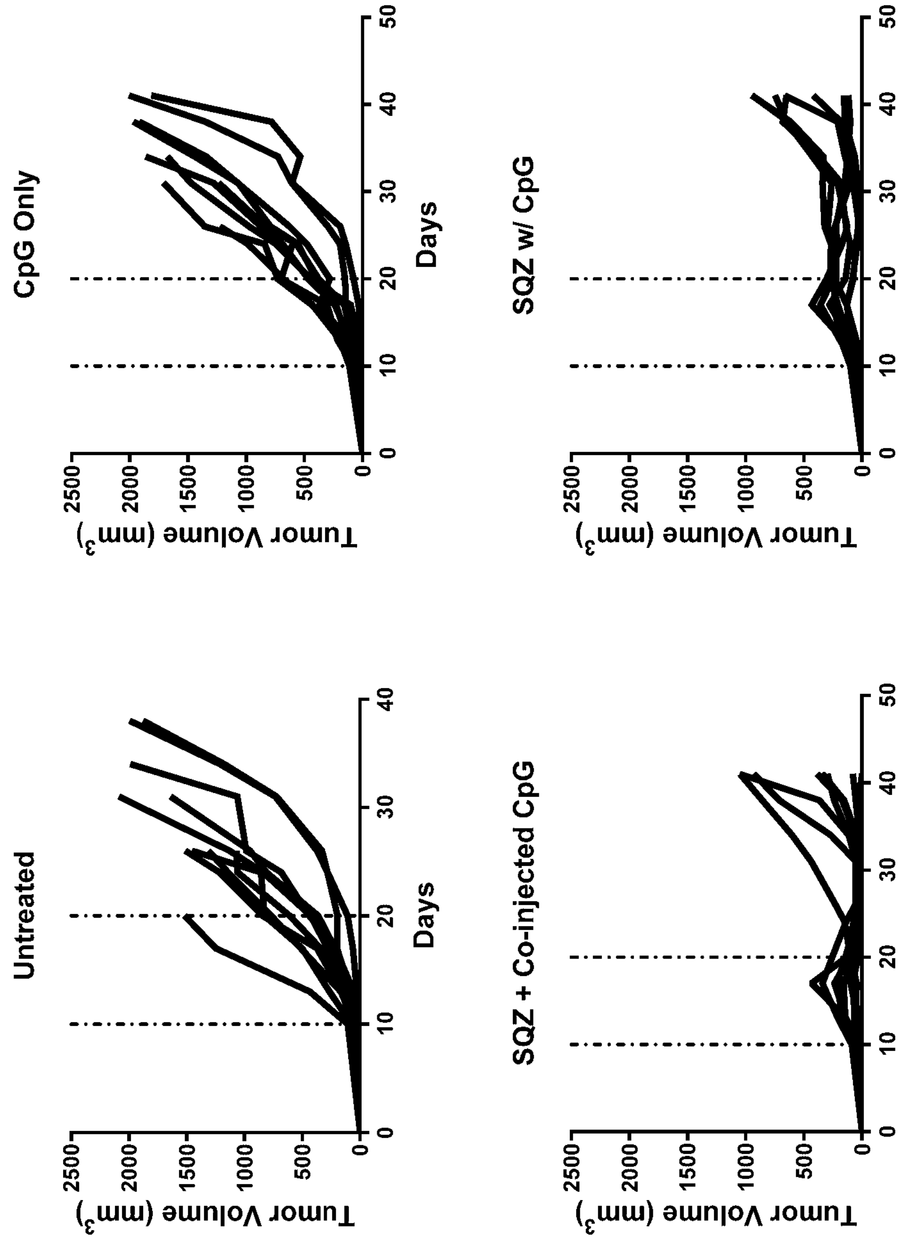
FIG. 12B shows tumor volume over time for individual mice within each treatment group.

In a therapeutic model of HPV-associated cancer (TC-1), T APCs that were SQZ'd with E7 SLP led to a significant reduction in tumor burden relative to untreated and CpG injection alone (Day 17: Group C—P<0.05; Day 20: Groups C & D—P<0.0001) (FIG. 12B). These data show that in a therapeutic setting both systemic co-administration and intracellular delivery of CpG adjuvant leads to a significant reduction in tumor burden relative to untreated or adjuvant alone.

Example 13

In order to assess the ability of co-administered adjuvants to lead to E7-specific T cell tumor infiltration, CpG vs. IFN-α were compared in combination with our E7-specific T APC in a therapeutic TC-1 murine tumor model. Antigen-specific T cell responses were measured in tumor infiltration lymphocytes by tetramer staining and flow cytometry.

On Day 0, recipient mice were injected in the right rear flank with TC1 tumor cells (50k cells/mouse). On Day 10, T cells from C57BL/6J female donor mice were isolated and loaded using SQZ with pre-complexed 20 μM E7 SLP (GQAEPDRAHYNIVTFSSKSDSTLRLSVQSTHVDIR; SEQ ID NO:25)+20 μM mouse serum albumin (MSA). SQZ-loaded T cells (5M cells/animal) were administered alone (Group C), with CpG ODN 1826 (25 μg/mouse—Group D), or IFN-α (10k IU/mouse—Group E) and were injected intravenously in 100 μL total volume. Mice were also injected with systemic CpG (25 μg—Group A) or IFN-α alone (10k IU—Group B). On Day 17, tumors were harvested and CD8+ tumor infiltrating T cells were isolated and E7-specific reactivity was assessed by tetramer staining. A representative schematic of the treatment groups and schedule is outlined in FIG. 13.

Figure 13:
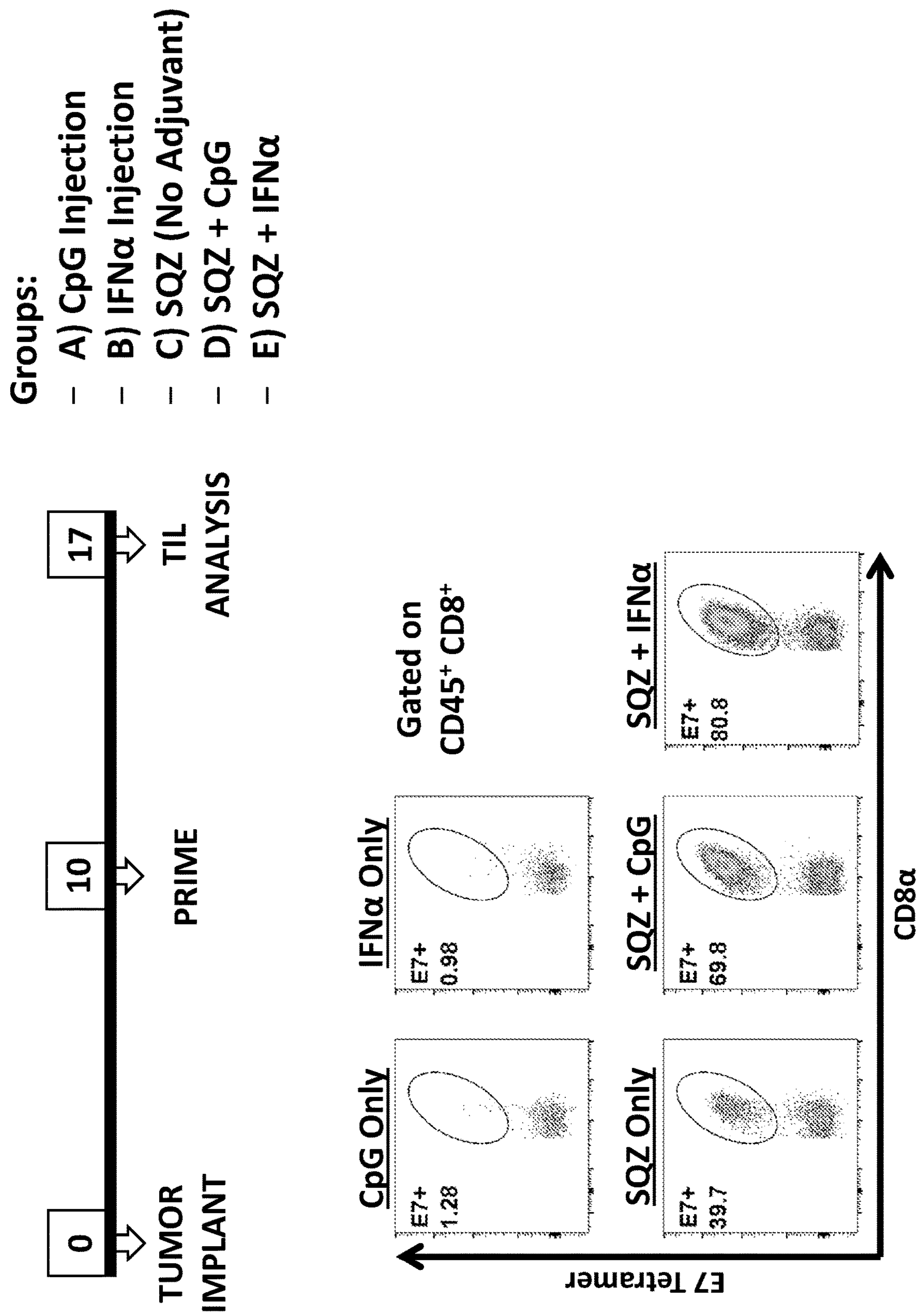
FIG. 13 shows a schematic of an experiment to assess the ability of co-administered adjuvants to lead to E7-specific T cell tumor infiltration. T cell responses are shown in the lower panel.

The percentage of E7-specific CD8+ T cell were measured in mice by E7 tetramer staining 7 days after prime (Day 17) and a representative example of the percentage of E7-specific T cells out of the CD8+ cells is shown in the bottom panel of FIG. 13. While injection of adjuvants alone did not generate an appreciable amount of E7-specific T cells, SQZ delivery of an E7 SLP afforded a 40% increase in E7-specific T cells and E7 delivered T cells in combination with CpG and IFN-α led to even higher percentages of antigen-specific T cells (70 and 80%, respectively). This data shows that a more robust E7-specific T cell response is generated when E7 SLP-loaded T cells are administered in combination with systemic adjuvants such as CpG or IFN-α.

Example 14

In order to determine a vaccination schedule for both prime and boost of T APCs loaded with an E7 synthetic long peptide (SLP)+CpG, we used a therapeutic TC-1 murine tumor model treated with our T APC vaccine at different time points and with differential number of boosts. The antitumor effect was measured by tumor growth inhibition.

Figure 14A:
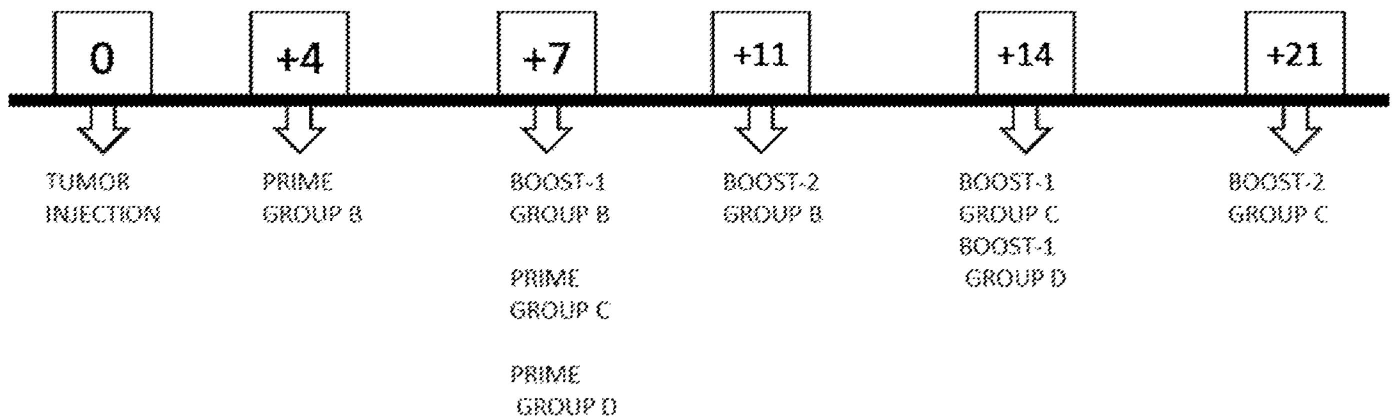
FIG. 14A is a schematic of an experiment to determine a vaccination schedule for both prime and boost of $T_{APC}$ s loaded with an E7 synthetic long peptide (SLP)+CpG.
Figure 14B:
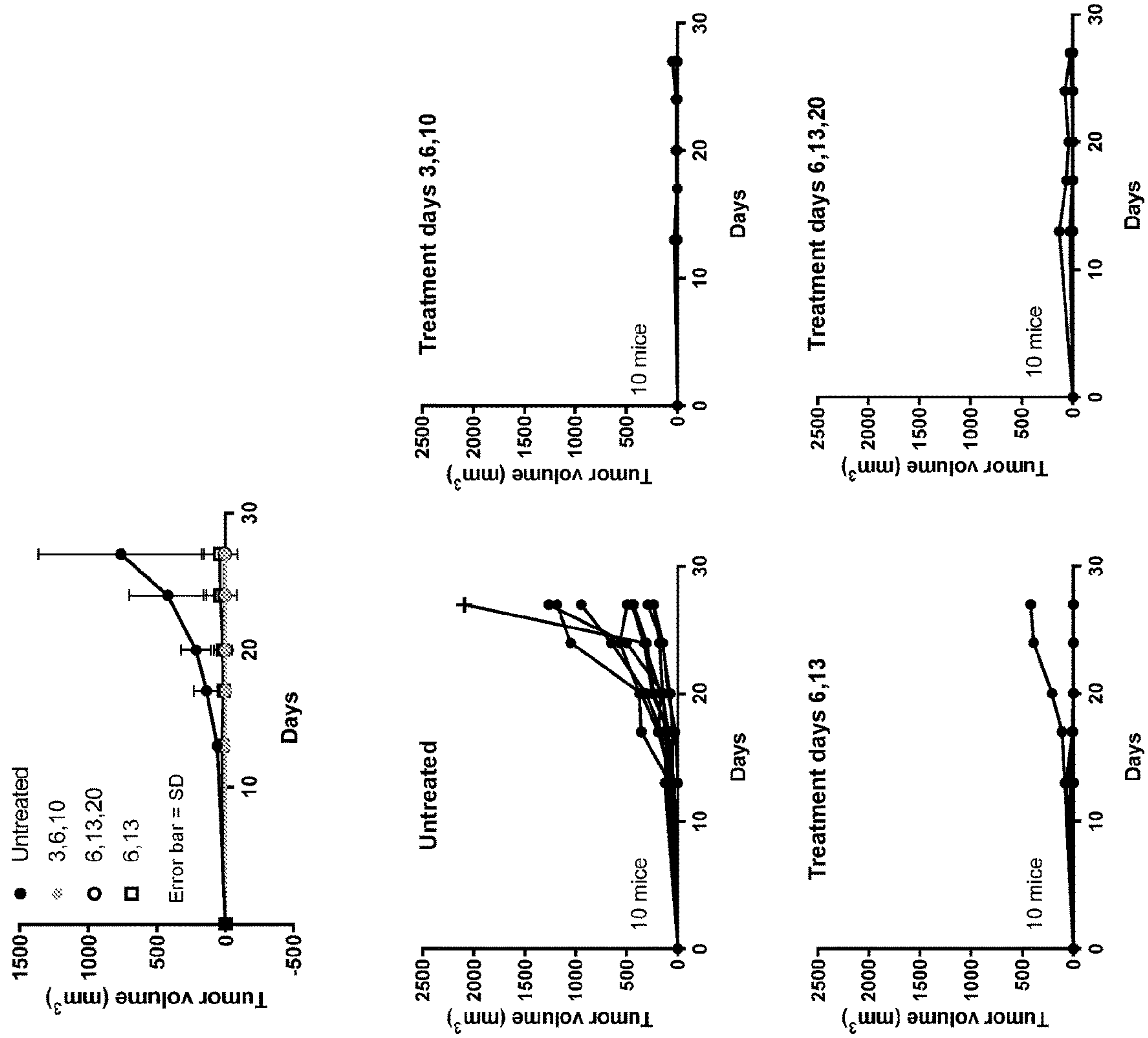
FIG. 14B shows growth of tumors for each experimental group.

On Day 0, recipient mice were injected in the right rear flank with TC1 tumor cells (50k cells/mouse) and TC-1 tumor growth was measured two times per week beginning on Day 11 and compared to tumor growth in untreated mice. On Days 3 or 6, T cells from C57BL/6J female donor mice were isolated and loaded using SQZ with pre-complexed 20 μM mouse serum albumin (MSA)+20 μM E7 SLP (GQAEPDRAHYNIVTFSSKSDSTLRLSVQSTHVDIR; SEQ ID NO:25)+200 μg/mL CpG ODN 1826 according to Table XX, followed by intravenous injection of recipient mice with 100 μL of loaded T cells (5M cells/animal). A representative schematic of the treatment groups and schedule is outlined in FIG. 14A.

Tumor growth inhibition occurred in all groups with T cells SQZ'd with E7+CpG, with statistical significance over untreated occurring at Day 20 (Day 20—All groups P<0.05; Day 24—All groups P<0.0001). This data shows that the dosing schedule with the T APC vaccine can work equally well when priming at Day 6 vs. Day 3 and there was no discernable benefit to adding a second boost at Day 21.

Example 15

In order to better understand the mechanism of antigen presentation by T cells that have had intracellular antigen delivery by SQZ, Ova was delivered to or incubated in the absence of SQZ with wild-type T cells injected into a wild-type mouse or into MHC-I knockout mice. Spleens were harvested and the amount of Ova-specific T cell (OT-I) proliferation was quantified by CFSE staining.

On Day 0, T cells from OT-I female donor mice were isolated and labeled with 2 μM CFSE and 2.5M cells were injected retro-orbitally (RO) in 100 μL PBS into either wild-type or MHC-I knockout mice. Also on Day 0, 400 μg/mL Ova was loaded into or incubated with T cells isolated from CD45.1 donor mice (4 mice/group), and 5M T cells were injected RO. On Day 3, spleens were harvested and the level of Ova-specific T cell proliferation was assessed by CFSE staining.

Figure 15:
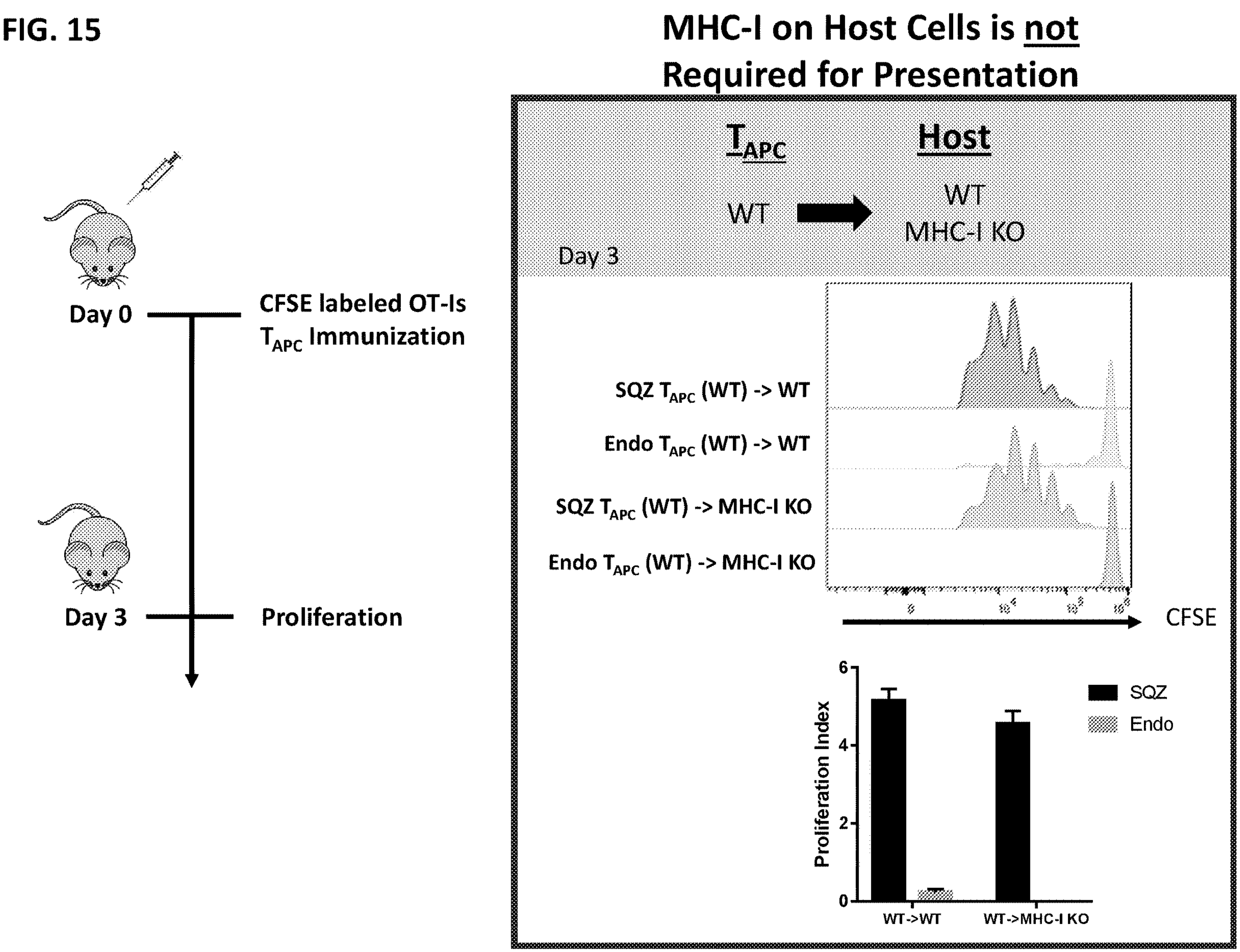
FIG. 15 shows the results of an experiment to show that SQZ'd $T_{APC}$s can present antigen directly.

The amount of Ova-specific T cell proliferation was assessed by CFSE labeling of Ova-responsive OT-I CD8+ T cells. To determine the mechanism of presentation of antigen-loaded $T_{APC}$s, mice deficient in MHC-I were used as recipient mice. This would preclude presentation of Ova antigens by endogenous murine APCs due to indirect uptake of antigen by dying SQZ'd T cells and cross-presentation on MHC-I to adoptively transferred OT-I cells. It was found that when recipient mice lack MHC-I, Ova-specific OT-I cell proliferation still occurred, providing evidence that SQZ'd T APCs are presenting antigen directly (FIG. 15). These data support the direct presentation of SQZ-mediated intracellularly delivered antigen.

Example 16

In order to assess the propensity of SQZ to alter cytokine production, T cells were SQZ delivered with CpG and assessed for the ability to alter T cell cytokine levels in an in vitro murine model. Cytokine levels in the supernatant were profiled using a multiplex cytokine kit.

C57BL/6J female recipient mice were primed with T cells from C57BL/6J female donor mice were isolated and SQZ'd with 200 μg/mL CpG and supernatants were collected after 24h (N=2). Supernatant was assessed for cytokine levels by Millipore Milliplex multiplex cytokine kit and expressed as a fold-change difference relative to untreated T cells.

Figure 16:
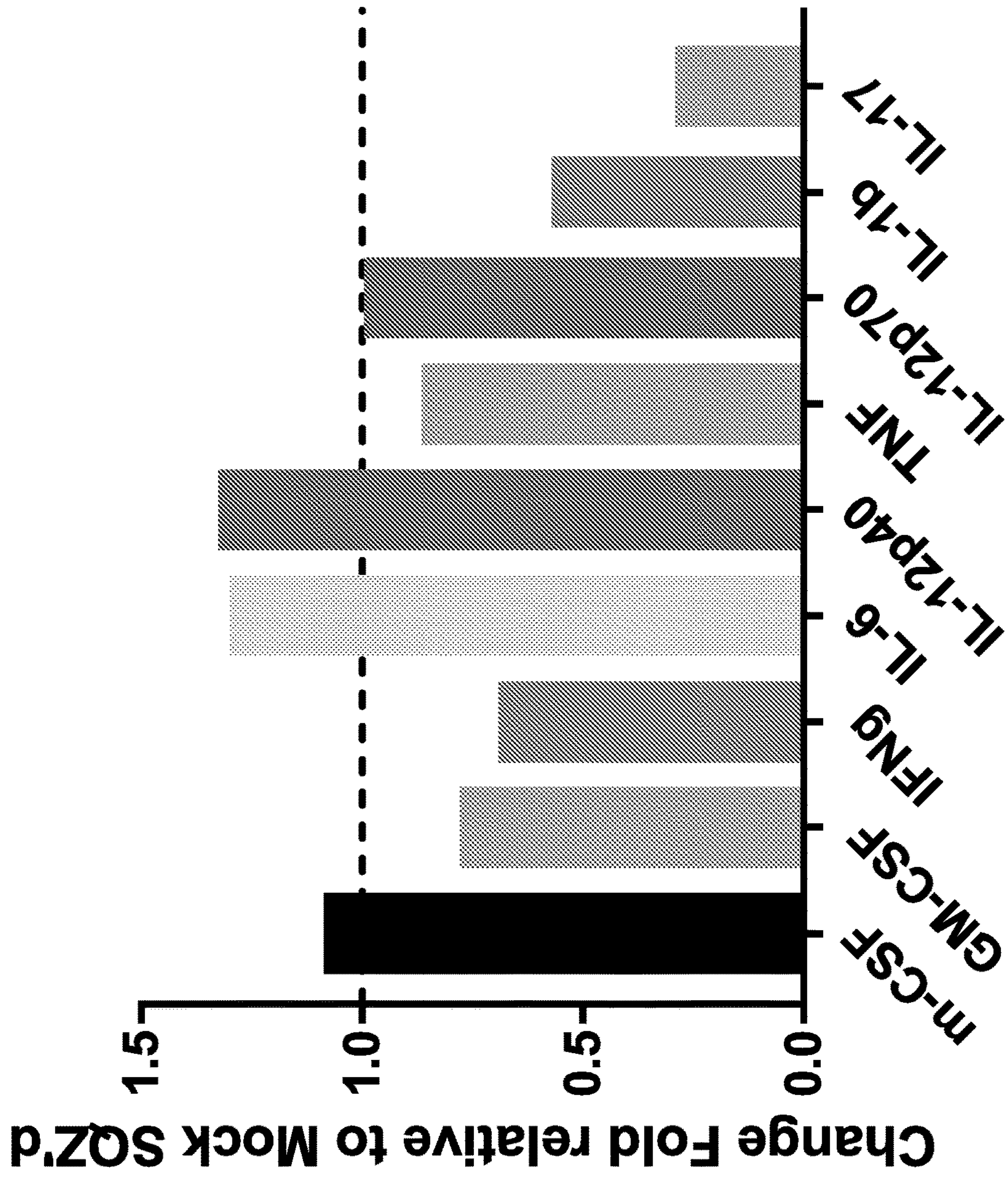
FIG. 16 shows that SQZ delivery of an adjuvant does not significantly alter T cell cytokine levels in vitro.

There were no significant changes between cytokine levels in the supernatant of T cells loaded with CpG via SQZ relative to untreated cells (FIG. 16). This data shows that SQZ delivery of an adjuvant does not significantly alter T cell cytokine levels in vitro.

Example 17

In order to assess the propensity of SQZ to alter cytokine production, T cells SQZ delivered with either Ova or Ova+

CpG were assessed for the ability to alter serum cytokine levels in an in vivo murine model. Serum cytokines were profiled using a multiplex cytokine kit.

C57BL/6J female recipient mice were primed with T cells from C57BL/6J female donor mice were isolated and SQZ'd with either 400 μg/mL Ova or Ova+200 μg/mL CpG and blood was drawn from the tail vein at 6 h and via cardiac puncture at 24 h post-priming. Serum was assessed for cytokine levels by Millipore Milliplex multiplex cytokine kit and expressed as a fold change vs. untreated T cells.

Figure 17:
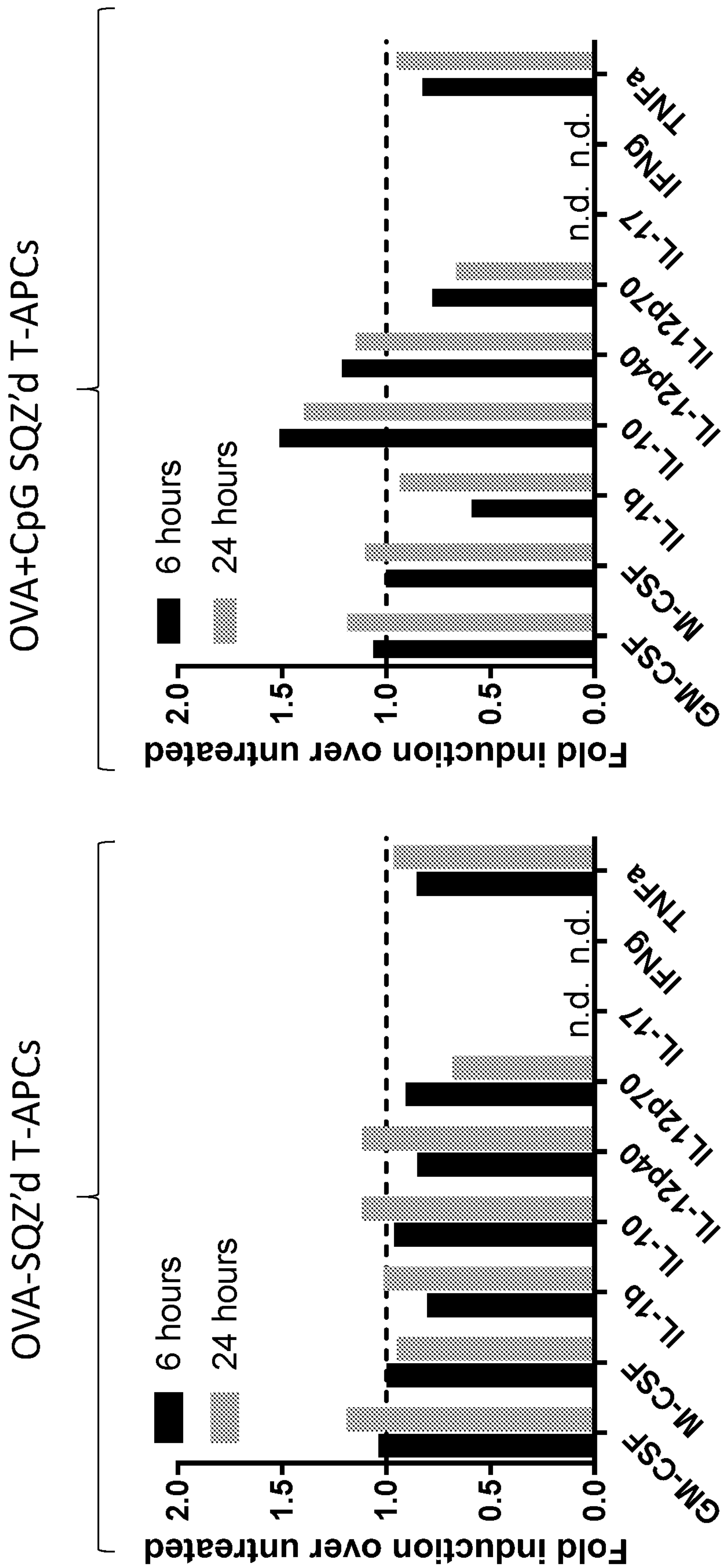
FIG. 17 shows that SQZ delivery of antigen+/−adjuvant does not significantly alter serum cytokine levels in vivo.

There were no significant changes between cytokine levels in the serum of mice primed with T cells loaded with Ova or Ova+CpG via SQZ (FIG. 17). Additionally, no significant differences were observed between 6 h and 24 h post-priming. These data show that SQZ delivery of antigen+/−adjuvant does not significantly alter serum cytokine levels in vivo.

Example 18

This example demonstrates, in part, that antigens introduced into T cells (T-APCs) are rapidly processed and directly presented.

In order to determine the kinetics of antigen-presentation of T cell as antigen-presenting cells (T-APCs), antigen was delivered to the T cell by SQZ, and the presence of the minimal peptide bound to MHC-I was assessed over time by immunostaining and flow cytometry.

Specifically, murine T cells from C56BL/6J mice were isolated and either SQZ-processed with no payload (SQZ: No Antigen) or with 200 μg/mL Ova protein loaded by SQZ (SQZ: Ovalbumin−N=3 technical replicates). At various time points between 2 hr-24 hr, the treated T cells were stained with an antibody (25-D1.16) specifically recognizing the Ova minimal epitope (SIINFEKL; SEQ ID NO:52), followed by flow cytometry. Any minimal epitope that had been processed from OVA protein and presented on MHC-I would be detected by immunostaining and the amount of antigen presentation was determined by flow cytometry.

Figure 18A:
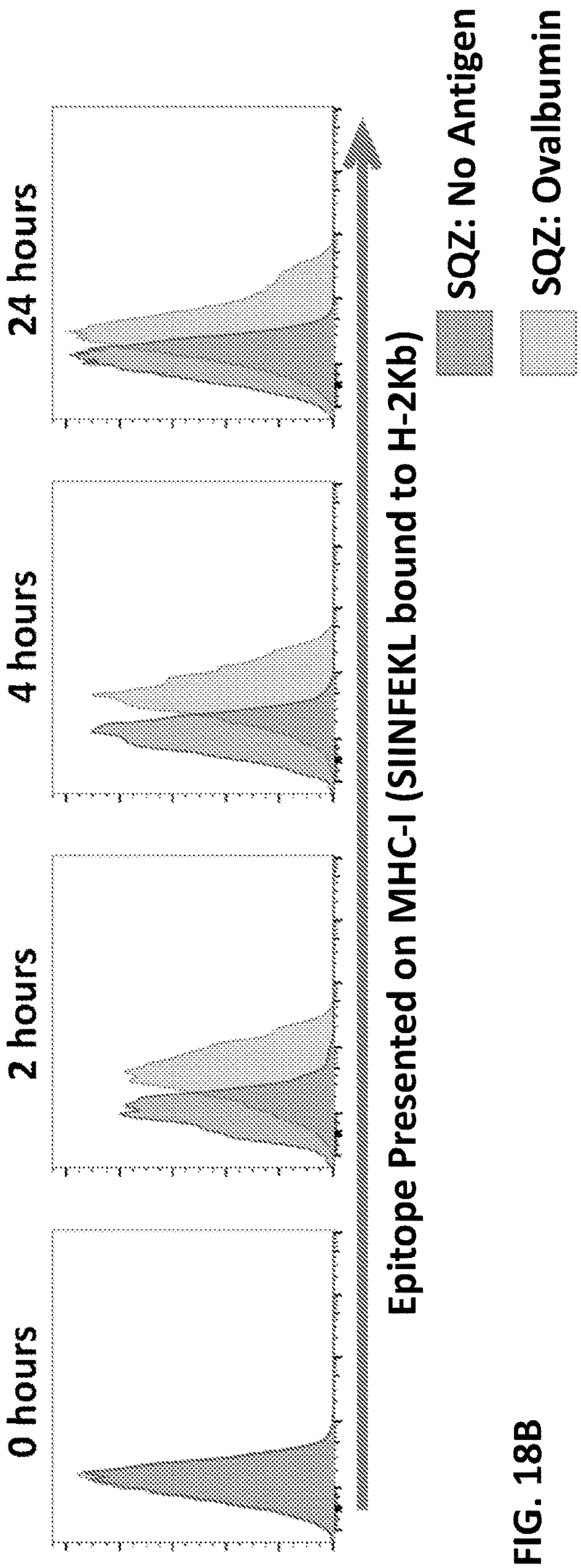
FIG. 18A shows histograms representing populations of cells with relative amount of minimal epitope presented on MHC-I.
Figure 18B:
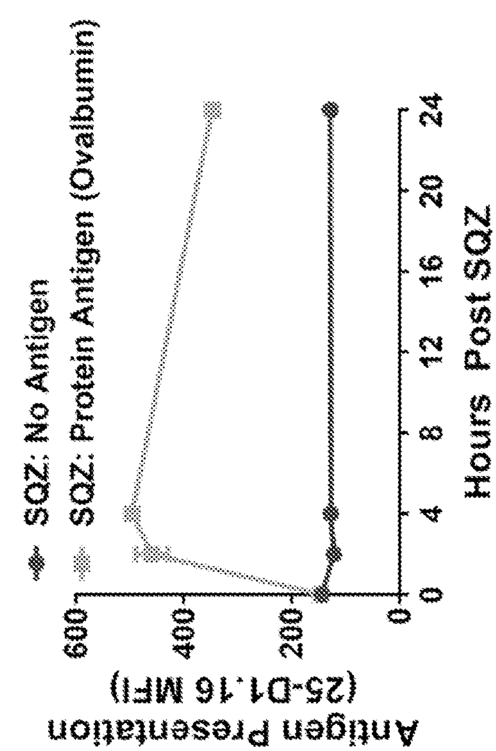
FIG. 18B shows the amount of antigen presentation per cell, as measured by mean fluorescence intensity.
Figure 19:
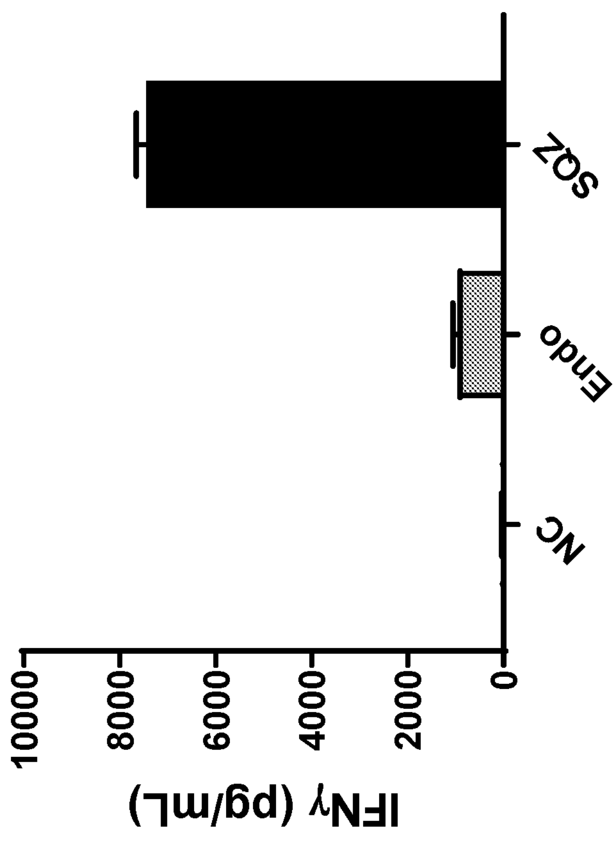
FIG. 19 shows the ability of T cells loaded with CMV pp65 antigen to induce an antigen-specific immune response in pp65 responder T cells in an in vitro model.
Figure 20:
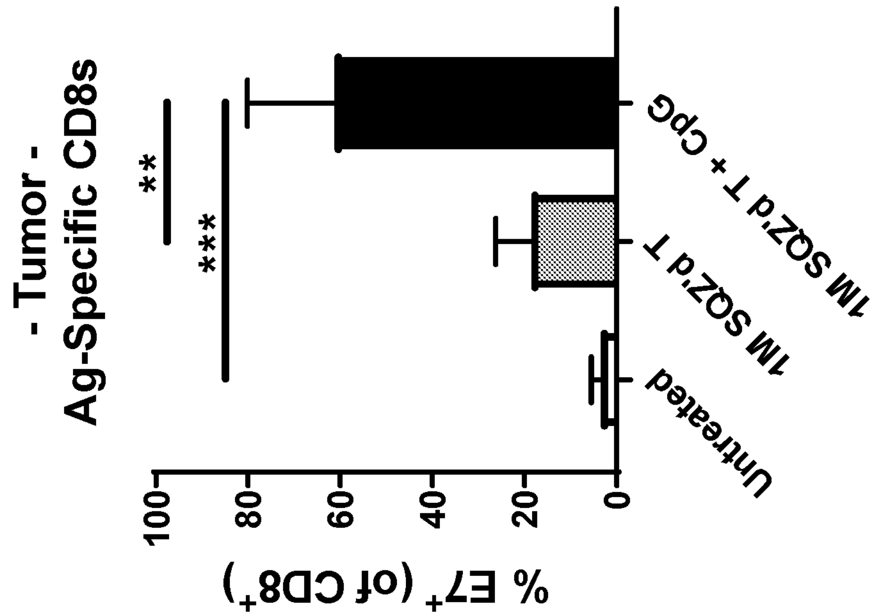
FIG. 20 shows the relative amounts of tumor infiltrating lymphocyte (TIL) recruitment to tumors administered with $T_{APC}$ SQZ-loaded with HPV16 E7 SLP, with or without co-administration of adjuvant.
Figure 21:
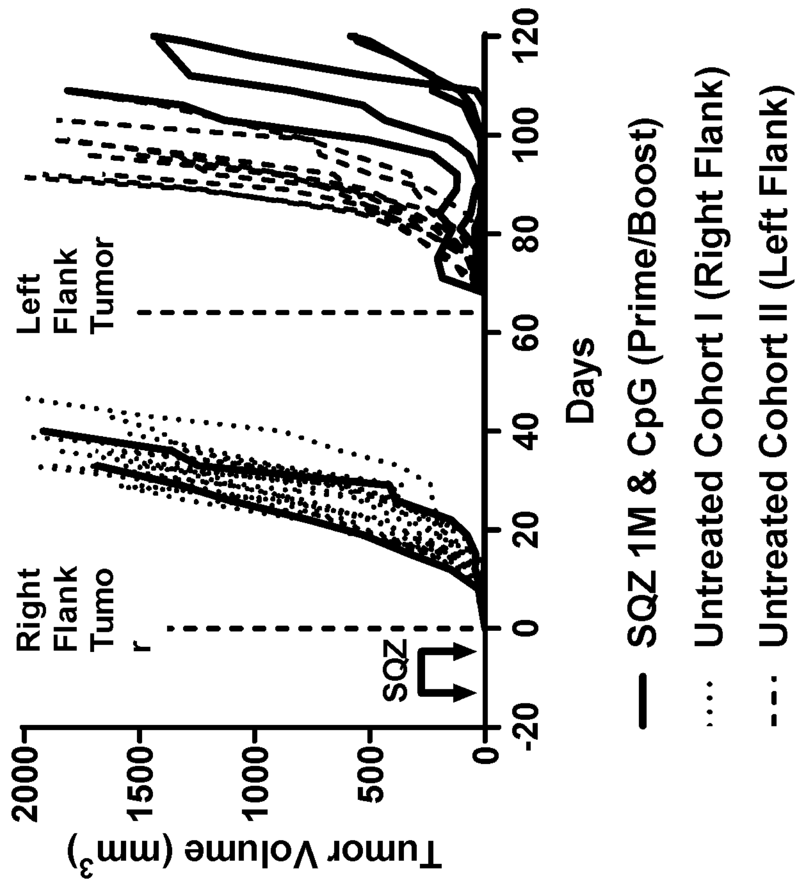
FIG. 21 shows the tumor volume over time in an experiment to determine the ability of SQZ-loaded T cells to act as APCs for prophylactic treatment for HPV-associated tumors, for both shorter term (right flank tumor, injected on Day 0) as well as longer term protection (left flank tumor, injected on Day 60)
Figure 22:
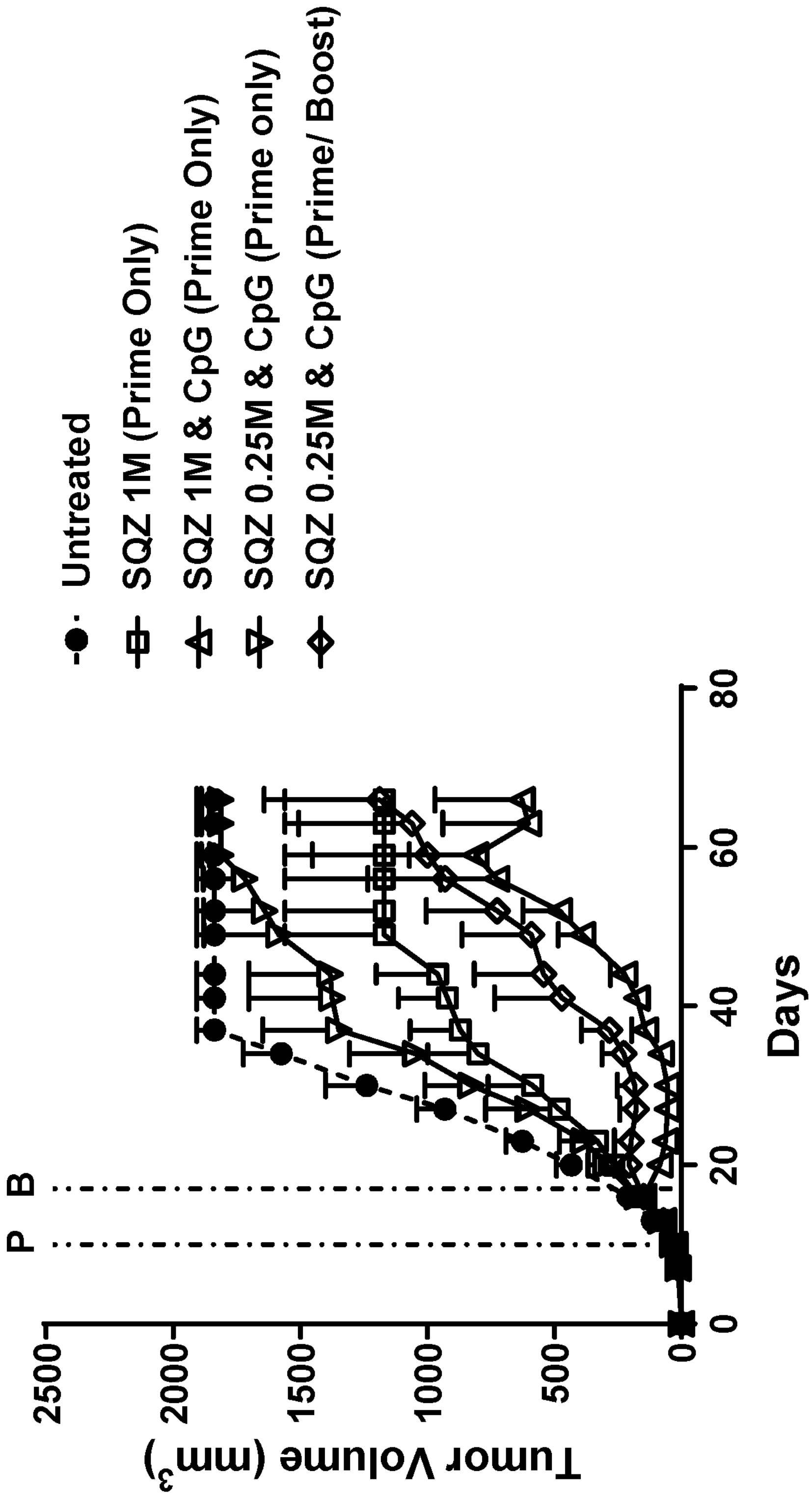
FIG. 22 shows the tumor volume over time in an experiment to determine the effect of T cell dose, co-administration of adjuvant as well as number of administrations (prime vs. prime/boost) on the ability of SQZ-loaded T cells to act as APCs for therapeutic treatment for HPV-associated tumors. "P" indicates prime, and "B" indicates boost in FIG. 22.

The relative populations of cells presenting various levels of SIINFEKL (SEQ ID NO:52) on MHC-I was depicted by the histograms (Dark gray represents SQZ: No antigen; Light Gray represents SQZ: Ovalbumin) overlaid at 0, 2, 4 and 24h (FIG. 18A). The rightward shift in the histogram representing SQZ: Ovalbumin indicated populations with increased SIINFEKL (SEQ ID NO:52) staining, and thus an increase of a population of cells presenting the processed antigen on MHC-I; as compared to the SQZ: No Antigen control. The described shift in the antigen-loaded T-APCs was evident at 2 hr, with small decreases in antigen-presentation observed only after 24 hrs. The relative amount of SIINFEKL (SEQ ID NO:52) presentation on MHC-I per cell over time was measured by mean fluorescence intensity (MFI) of the cells (FIG. 18B). SQZ: Ovalbumin populations showed an appreciable presentation of SIINFEKL (SEQ ID NO:52) after 2 hr, with the maximum presentation observed at 4 hr, followed by a slight decrease overtime observed between 4 and 24 hr. Throughout the measured time course, there was no observed difference in antigen presentation for the SQZ: No Antigen control. Taken together, this data supports that SQZ-mediated loading of antigen into T cells led to rapid presentation of the antigen (2-4h).

Example 19

This example demonstrates, in part, that T cells that have been SQZ-loaded with a disease-relevant antigen (T-APCs) efficiently stimulate in vitro antigen-specific T cell responses.

In order to determine the ability of human T cells that have been SQZ-loaded with a disease-relevant antigen (T-APCs) to stimulate an antigen-specific T cell response, T cells were SQZ-loaded with a CMV-associated antigen, co-cultured with antigen-specific responder T cells, and the levels of inflammatory cytokine secretion were measured by ELISA.

Specifically, human T cells from HLA-A2+ donors were isolated and a CMV pp65 SLP (50 μM) was either incubated with T cells (Endo), or delivered to T cells by SQZ (SQZ). Endo T cells or SQZ T cells (60k cells/well) were then incubated with pp65 responder T cells (30k cells/well) in a 2:1 ratio, and co-cultured in the presence of IL-2 (100 U/mL) and CpG 2006 (1 μM) for 24 hrs. Supernatants were then harvested and analyzed by ELISA for levels of IFN-γ secretion, which indicates the amount of in vitro antigen-specific immune stimulation.

When compared to T cells that were incubated with the pp65 SLP (Endo), there was a considerable and statistically significant increase in the stimulation of pp65-specific responders by the SQZ-loaded T cells, as measured by IFN-γ ELISA ($P<0.005$). These data show that by SQZ-loading disease-relevant antigens, human T cells could be modified to become efficient APCs in stimulating disease-relevant antigen-specific T cell responses in vitro.

Example 20

In order to evaluate the importance of adjuvant on the ability of a SQZ-loaded vaccine to induce antigen-specific tumor infiltrating lymphocytes (TILs), cells were loaded with a model antigen, matured with adjuvant and injected into tumor bearing mice. The relative percentage of antigen-specific T cells recruited to the tumor was measured by flow cytometry.

C57BL/6J female mice were injected in the right rear flank with TC1 tumor cells (50k cells/mouse) at Day 0. On Day 15 (prime), murine T cells were obtained from spleens of female C57BL/6J donor mice and were loaded with pre-complexed 5 μM E7 SLP (GQAEPDRAHYNIVTFSSKSDSTLRLSVQSTHVDIR; SEQ ID NO:25)+5 μM mouse serum albumin (MSA) via SQZ (40 psi, 3.5 μm constriction, room temperature) and incubated for 1 h at 37° C. Female C57BL/6J recipient mice (10/group) were injected retro-orbitally on Day 15 with 100 μL of either vehicle (PBS—Untreated) or E7-loaded T cells (1M cells/mouse)+/−CpG 1826 (25 μg/mouse). On Day 25, tumors were harvested and the amount of E7-specific TILs was measured by flow cytometry.

SQZ-loaded T APCs alone led to a small (~15%) but statistically insignificant increase in the number of E7-specific TILs, but when co-injected with CpG, there was higher and significant increase in the number of TILs (~55%, $^{}P<0.01$ compared to T APC alone; $^{*}P<0.0005$ compared to untreated). This data shows that co-injecting CpG along with the E7-loaded T APC leads to much higher recruitment of TILs compared to T APC alone.

Example 21

In order to evaluate the durability of the T APC+ adjuvant vaccine in a prophylactic setting, T APC-treated mice were compared to untreated mice for the tumor growth of an HPV E7-expressing TC1 tumor model both for the initial response, as well as a re-challenge 60 days later, with the area of the tumors plotted against time.

At Day −14, splenocyte were harvested from C57BL/6J female donor mice and T cells were isolated by immunomagnetic separation. Next, murine T cells were loaded with pre-complexed 20 μM E7 SLP (GQAEPDRAHYNIVTFSSKSDSTLRLSVQSTHVDIR; SEQ ID NO:25)+20 μM mouse serum albumin (MSA) via SQZ (45 psi; 3.5 μm constriction) and incubated for 1 hour at 37° C. Female C57BL/6J recipient mice (10 mice/group, except untreated cohort I, which was 20 mice/group) were injected retro-orbitally with 100 μL of either vehicle (PBS—Untreated) or E7-loaded T cells (1M cells/mouse)+CpG 1826 (25 μg/mouse) [Prime]. On Day −7, spleens were harvested from C57BL/6J female donor mice and T cells were isolated and SQZ'd and injected into recipient mice exactly as on Day −14 [Boost]. On Day 0, C57BL/6J female mice were injected in the right rear flank (except the 10 untreated cohort 2 that were not implanted with tumor cells until Day 64 with TC1 tumor cells (50k cells/mouse). TC-1 tumor growth was measured beginning 1 week post-tumor implantation two times per week and compared to tumor growth in untreated mice for up to 120 days.

Tumor growth, as measured by the formula ((length×width2)/2), was compared between mice from the untreated group and the T APC-treated group challenged with tumor cells at Day 0, and while all mice reached the humane endpoint in the untreated group by Day 47, there was significant tumor growth delay for the T APC group in all but 2 of the T APC mice, with the remainder of the mice (8) remaining tumor-free until re-challenged with tumors. Interestingly, when untreated mice that were implanted with tumors on Day 64 and compared to T APC-treated mice that had tumors re-implanted in their opposite flank, there was still a tumor growth delay, with 3 of the mice never growing measurable tumors, even after the secondary tumor challenge. These data suggest that treatment with E7-loaded T APCs+adjuvant can not only lead to antigen-specific tumor growth inhibition, but also tumor prevention that can even be durable over >100 days despite a secondary tumor challenge.

Example 22

In order to evaluate the impact of differing T APC concentration as well as prime-boosting schedules in a therapeutic vaccine setting, T APC-treated mice (multiple concentrations and prime-boost schedules) were compared to untreated mice for the tumor growth of an HPV E7-expressing TC1 tumor model, with the area of the tumors plotted against time.

At Day 0, C57BL/6J female mice were injected in the right rear flank with TC1 tumor cells (50k cells/mouse). On Day 10 (prime), murine T cells were obtained from spleens of female C57BL/6J donor mice by immunomagnetic separation and were loaded with pre-complexed 20 μM E7 SLP (GQAEPDRAHYNIVTFSSKSDSTLRLSVQSTHVDIR; SEQ ID NO:25)+20 μM mouse serum albumin (MSA) via SQZ (45 psi; 3.5 μm constriction) and incubated for 1 hour at 37° C. Then, female C57BL/6J recipient mice (10/group) were injected retro-orbitally with 100 μL of either vehicle (PBS) or T APCs (0.25 or 1M cells/mouse)+CpG 1826 (25 μg/mouse). On Day 17, the Prime/Boost group received a second injection with T APCs in an identical manner to Day 10. TC-1 tumor growth was measured beginning 1 week post-tumor implantation two times per week and compared to tumor growth in untreated mice for up to 66 days.

Tumor growth, as measured by the formula ((length×width2)/2) and the low dose T APC group (0.25M cells/mouse)+CpG (prime only) only led to a slight delay in tumor growth rate compared to untreated. The inclusion of a boost at Day 17 with the low dose of T APC+CpG (0.25M prime/boost) saw an enhancement of the tumor growth inhibition relative to the same concentration prime only condition and much larger inhibition relative to untreated. Increasing the dose of antigen-loaded T APCs to 1M/mouse (prime only) led to a slight tumor growth inhibition relative to the lower dose T APC+CpG (prime only). Interestingly, the use of the high dose T APC+CpG (prime only) led to the best protection from tumor growth, with tumor regression occurring between Days 20-40 and the highest level of growth inhibition of any of the observed groups. Taken together, these data highlight that increased cell dose, inclusion of adjuvant, or prime+boost dosing schedules can enhance the efficacy of a T APC vaccine.

Sequence Listing

| SEQ ID NO | Sequence | Description |
|---|---|---|
| 1 | TIHDIILECV | HPV16-E6(29-38), human epitope |
| 2 | EVYDFAFRDL | HPV16-E6(48-57), murine epitope |
| 3 | YMLDLQPETT | HPV16-E7(11-20), human epitope |
| 4 | RAHYNIVTF | HPV16-E7(49-57), murine epitope |
| 5 | LPQLSTELQT | HPV16-E6(19-28) N-terminal polypeptide, human |
| 6 | QLCTELQT | HPV16-E6(21-28) N-terminal polypeptide, human |
| 7 | KQQLLRR | HPV16-E6(41-47) N-terminal polypeptide, native murine |
| 8 | VYSKQQLLRR | HPV16-E6(38-47) N-terminal polypeptide, classic murine |
| 9 | MHGDTPTLHE | HPV16-E7(1-10) N-terminal polypeptide, human |
| 10 | GQAEPD | HPV16-E7(43-48) N-terminal polypeptide, murine |
| 11 | YSKQQLLRREVYDFAF | HPV16-E6(39-54) C-terminal polypeptide, human |

-continued

| Sequence Listing | | |
|---|---|---|
| SEQ ID NO | Sequence | Description |
| 12 | YCKQQLL | HPV16-E6(39-45) C-terminal polypeptide, human |
| 13 | CIVYRDGN | HPV16-E6(58-65) C-terminal polypeptide, native murine |
| 14 | SIVYRDGNPYAVSDK | HPV16-E6(58-72) C-terminal polypeptide, classic murine |
| 15 | DLYCYEQLNDSSEEE | HPV16-E7(21-35) C-terminal polypeptide, human |
| 16 | CCKCDSTLRLCVQSTHVDIR | HPV16-E7(58-77 C-terminal polypeptide, native murine |
| 17 | SSKSDSTLRLSVQSTHVDIR | HPV16-E7(58-77) C-terminal polypeptide, classic murine |
| 18 | LPQLSTELQTTIHDIILECVYSKQQLLRREVYDFAF | HPV16-E6(19-54) SLP, human |
| 19 | QLCTELQTTIHDIILECVYCKQQLL | HPV16-E6(21-45) SLP, human |
| 20 | KQQLLRREVYDFAFRDLCIVYRDGN | HPV16-E6(41-65) SLP, native murine |
| 21 | VYSKQQLLRREVYDFAFRDLSIVYRDGNPYAVSDK | HPV16-E6(38-72) SLP, classic murine |
| 22 | MHGDTPTLHEYMLDLQPETTDLYCYEQLNDSSEEE | HPV16-E7(1-35) SLP, human |
| 23 | QLCTELQTYMLDLQPETTYCKQQLL | HPV16-E7.6 SLP, human |
| 24 | GQAEPDRAHYNIVTFCCKCDSTLRLCVQSTHVDIR | HPV16-E7(43-77) SLP, native murine |
| 25 | GQAEPDRAHYNIVTFSSKSDSTLRLSVQSTHVDIR | HPV16-E7(43-77) SLP, classic murine |
| 26 | ggGGTCAACGTTGAgggggg<br>Bases shown in capital letters are phosphodiester, and those in lower case are phosphorothioate | ODN 1585 (Class A, mouse-specific) |
| 27 | ggGGGACGA:TCGTCgggggg<br>Bases shown in capital letters are phosphodiester, and those in lower case are phosphorothioate | ODN 2216 (Class A, human-selective) |
| 28 | gggGACGAC:GTCGTGgggggg<br>Bases shown in capital letters are phosphodiester, and those in lower case are phosphorothioate | ODN 2336 (Class A, human preferred) |
| 29 | tccatgacgttcctgatgct<br>Bases shown in capital letters are phosphodiester, and those in lower case are phosphorothioate | ODN 1668 (Class B, mouse specific) |
| 30 | tccatgacgttcctgacgtt<br>Bases are phosphorothioate | ODN 1826 (Class B, mouse specific) |
| 31 | tcgtcgttttgtcgttttgtcgtt<br>Bases are phosphorothioate | ODN 2006 (Class B, human selective) |
| 32 | tcg tcg ttg tcg ttt tgt cgt t<br>Bases are phosphorothioate | ODN 2007 (Class B, bovine/porcine) |
| 33 | tcg acg ttc gtc gtt cgt cgt tc<br>Bases are phosphorothioate | ODN BW006 (Class B, human & mouse) |
| 34 | tcg cga cgt tcg ccc gac gtt cgg ta<br>Bases are phosphorothioate | ODN D-SL01 (Class B, multispecies) |
| 35 | tcgtcgttttcggcgc:gcgccg<br>Bases are phosphorothioate | ODN 2395 (Class C, human/mouse) |
| 36 | tcgtcgtcgttc:gaacgacgttgat<br>Bases are phosphorothioate | ODN M362 (Class C, human/mouse) |
| 37 | tcg cga acg ttc gcc gcg ttc gaa cgc gg<br>Bases are phosphorothioate | ODN D-SL03 (Class C, multispecies) |
| 38 | MHGDTPTLHEYMLDLQPETTDLYCYEQLNDSSEEE | E7 |
| 39 | LYCYEQLNDSSEEEDEIDGPAGQAEPDRAHYNIVT | E7 |
| 40 | GQAEPDRAHYNIVTFCCKCDSTLRLCVQSTHVDIR | E7 |
| 41 | TLRLCVQSTHVDIRTLEDLLMGTLGIVCPICSQKP | E7 |
| 42 | MHQKRTAMFQDPQERPRKLPQLCTELQTTIHD | E6 |
| 43 | LPQLCTELQTTIHDIILECVYCKQQLLRREVY | E6 |
| 44 | KQQLLRREVYDFAFRDLCIVYRDGN | E6 |
| 45 | RDLCIVYRDGNPYAVCDKCLKFYSKI | E6 |
| 46 | DKCLKFYSKISEYRHYCYSLYGTTL | E6 |
| 47 | HYCYSLYGTTLEQQYNKPLCDLLIR | E6 |
| 48 | YGTTLEQQYNKPLCDLLIRCINCOKPLCPEEK | E6 |
| 49 | RCINCQKPLCPEEKQRHLDKKQRFHNIRGRWT | E6 |
| 50 | DKKQRFHNIRGRWTGRCMSCCRSSRTRRETQL | E6 |

What is claimed is:

1. A modified T cell comprising an antigen and an adjuvant, wherein the antigen is exogenous to the modified T cell and comprises an immunogenic epitope, wherein the antigen and the adjuvant are present in the cytosol and/or endosomes of the modified T cell, and wherein the antigen is capable of being processed into an MHC class I-restricted peptide and/or an MHC class II-restricted peptide, and wherein the immunogenic epitope is derived from a disease-associated antigen, a non-self antigen, a tumor antigen, a viral antigen, or an allergen-derived antigen, wherein the disease-associated antigen, the non-self antigen, the tumor antigen, or the viral antigen comprises an amino acid sequence of any one of SEQ ID Nos: 18, 21, 23 and 25, or wherein the allergen-derived antigen is presented by the modified T cell within 2-4 hours.

2. A modified T cell comprising an antigen and an adjuvant, wherein the antigen comprises an immunogenic epitope, prepared by a process comprising the steps of:

a) passing a cell suspension comprising an input T cell through a cell-deforming constriction, wherein a diameter of the constriction is a function of a diameter of the input T cell in the suspension, thereby causing perturbations of the input T cell large enough for the antigen and the adjuvant to pass through to form a perturbed input T cell; and b) incubating the perturbed input T cell with the antigen for a sufficient time ranging from 1 second to at least 30 minutes to allow the antigen to enter the perturbed input T cell, thereby generating the modified T cell comprising the antigen and the adjuvant, wherein the antigen is capable of being processed into an MHC class I-restricted peptide and/or an MHC class II-restricted peptide, and wherein the immunogenic epitope is derived from a disease-associated antigen, a non-self antigen, a tumor antigen, a viral antigen, or an allergen-derived antigen, wherein the disease-associated antigen, the non-self antigen, the tumor antigen, or the viral antigen comprises an amino acid sequence of any one of SEQ ID Nos: 18, 21, 23 and 25, or wherein the allergen-derived antigen is presented by the modified T cell within 2-4 hours.

3. A modified T cell comprising an antigen and an adjuvant, wherein the antigen comprises an immunogenic epitope, prepared by a process comprising the steps of:

a) passing a cell suspension comprising an input T cell comprising the adjuvant through a cell-deforming constriction, wherein a diameter of the constriction is a function of a diameter of the input T cell in the suspension, thereby causing perturbations of the input T cell large enough for the antigen to pass through to form a perturbed input T cell; and b) incubating the perturbed input T cell with the antigen for a sufficient time ranging from 1 second to at least 30 minutes to allow the antigen to enter the perturbed input T cell, thereby generating the modified T cell comprising the antigen and the adjuvant, wherein the antigen is capable of being processed into an MHC class I-restricted peptide and/or an MHC class II-restricted peptide, and wherein the immunogenic epitope is derived from a disease-associated antigen, a non-self antigen, a tumor antigen, a viral antigen, or an allergen-derived antigen, wherein the disease-associated antigen, the non-self antigen, the tumor antigen, or the viral antigen comprises an amino acid sequence of any one of SEQ ID Nos: 18, 21, 23 and 25, or wherein the allergen-derived antigen is presented by the modified T cell within 2-4 hours.

4. A modified T cell comprising an antigen and an adjuvant, wherein the antigen comprises an immunogenic epitope, prepared by a process comprising the steps of:

a) passing a cell suspension comprising an input T cell comprising the antigen through a cell-deforming constriction, wherein a diameter of the constriction is a function of a diameter of the input T cell in the suspension, thereby causing perturbations of the input T cell large enough for the adjuvant to pass through to form a perturbed input T cell; and incubating the perturbed input T cell with the antigen for a sufficient time ranging from 1 second to at least 30 minutes to allow the antigen to enter the perturbed input T cell, thereby generating the modified T cell comprising the antigen and the adjuvant, wherein the antigen is capable of being processed into an MHC class I-restricted peptide and/or an MHC class II-restricted peptide, and wherein the immunogenic epitope is derived from a disease-associated antigen, a non-self antigen, a tumor antigen, a viral antigen, or an allergen-derived antigen, wherein the disease-associated antigen, the non-self antigen, the tumor antigen, or the viral antigen comprises an amino acid sequence of any one of SEQ ID Nos: 18, 21, 23 and 25, or wherein the allergen-derived antigen is presented by the modified T cell within 2-4 hours.

5. A composition comprising the modified T cell of claim 1.

6. A pharmaceutical composition comprising the modified T cell of claim 1 and a pharmaceutically acceptable carrier.

7. A pharmaceutical composition comprising a modified T cell comprising an antigen and an adjuvant, wherein the antigen comprises an immunogenic epitope, prepared by a process comprising the steps of:

a) passing a cell suspension comprising an input T cell through a cell-deforming constriction, wherein a diameter of the constriction is a function of a diameter of the input T cell in the suspension, thereby causing perturbations of the input T cell large enough for the antigen to pass through to form a perturbed input T cell; and b) incubating the perturbed input T cell with the antigen and the adjuvant for a sufficient time ranging from 1 second to at least 30 minutes to allow the antigen to enter the perturbed input T cell;

thereby generating the pharmaceutical composition comprising the modified T cell comprising the antigen and the adjuvant, wherein the antigen is capable of being processed into an MHC class I-restricted peptide and/or an MHC class II-restricted peptide, and wherein the immunogenic epitope is derived from a disease-associated antigen, a non-self antigen, a tumor antigen, a viral antigen, or an allergen-derived antigen, wherein the disease-associated antigen, the non-self antigen, the tumor antigen, or the viral antigen comprises an amino acid sequence of any one of SEQ ID Nos: 18, 21, 23 and 25, or wherein the allergen-derived antigen is presented by the modified T cell within 2-4 hours.

* * * * *